United States Patent
Wang

(10) Patent No.: US 10,801,042 B1
(45) Date of Patent: Oct. 13, 2020

(54) USE OF ION CONCENTRATIONS TO INCREASE THE PACKAGING EFFICIENCY OF RECOMBINANT ADENO-ASSOCIATED VIRUS

(71) Applicant: Vigene Biosciences Inc., Rockville, MD (US)

(72) Inventor: Qizhao Wang, Rockville, MD (US)

(73) Assignee: Vigene Biosciences, Inc., Rockville, MD (US)

(*) Notice: Subject to any disclaimer, the term of this patent is extended or adjusted under 35 U.S.C. 154(b) by 0 days.

(21) Appl. No.: 16/511,612

(22) Filed: Jul. 15, 2019

(51) Int. Cl.
*C12N 15/86* (2006.01)
*C12N 7/00* (2006.01)
*C12N 5/16* (2006.01)

(52) U.S. Cl.
CPC ............ *C12N 15/86* (2013.01); *C12N 5/16* (2013.01); *C12N 7/00* (2013.01); *C12N 2500/14* (2013.01); *C12N 2500/16* (2013.01); *C12N 2710/10041* (2013.01)

(58) Field of Classification Search
CPC . C12N 15/86; C12N 5/16; C12N 7/00; C12N 2500/16; C12N 2710/10041; C12N 2500/14
See application file for complete search history.

(56) References Cited

U.S. PATENT DOCUMENTS

| | | |
|---|---|---|
| 6,566,118 B1 | 5/2003 | Atkinson et al. |
| 6,723,551 B2 | 4/2004 | Kotin et al. |
| 6,733,757 B2 | 5/2004 | Patel et al. |
| 6,753,419 B1 | 6/2004 | Toniatti et al. |
| 6,759,050 B1 | 7/2004 | Sista et al. |
| 6,764,845 B2 | 7/2004 | Sista et al. |
| 6,821,511 B2 | 11/2004 | Kotin et al. |
| 6,841,357 B1 | 1/2005 | Vaillancourt et al. |
| 6,846,665 B1 | 1/2005 | Borer et al. |
| 6,962,815 B2 | 11/2005 | Bartlett |
| 6,984,517 B1 | 1/2006 | Chiorini et al. |
| 6,989,264 B2 | 1/2006 | Atkinson et al. |
| 6,995,006 B2 | 2/2006 | Atkinson et al. |
| 7,105,345 B2 | 9/2006 | Wilson et al. |
| 7,115,391 B1 | 10/2006 | Chen et al. |
| 7,122,348 B2 | 10/2006 | Wong et al. |
| 7,186,552 B2 | 3/2007 | Wilson et al. |
| 7,208,315 B2 | 4/2007 | Miller et al. |
| 7,271,002 B2 | 9/2007 | Kotin et al. |
| 7,419,817 B2 | 9/2008 | Chiorini et al. |
| 7,439,065 B2 | 10/2008 | Ferrari et al. |
| 7,479,554 B2 | 1/2009 | Chiorini et al. |
| 7,598,070 B2 | 10/2009 | Sista et al. |
| 7,625,570 B1 | 12/2009 | Schaffer et al. |
| 7,906,111 B2 | 3/2011 | Wilson et al. |
| 8,163,543 B2 | 4/2012 | Urabe et al. |
| 8,192,975 B2 | 6/2012 | Sista et al. |
| 8,507,267 B2 | 8/2013 | Chiorini et al. |
| 8,697,359 B1 | 4/2014 | Zhang |
| 8,846,389 B2 | 9/2014 | Chiorini et al. |
| 8,852,607 B2 | 10/2014 | Sista et al. |
| 8,945,918 B2 | 2/2015 | Chen |
| 9,193,956 B2 | 11/2015 | Schaffer et al. |
| 9,441,206 B2 | 9/2016 | Grieger et al. |
| 9,441,244 B2 | 9/2016 | Schaffer et al. |
| 9,457,103 B2 | 10/2016 | Schaffer et al. |
| 9,458,517 B2 | 10/2016 | Schaffer et al. |
| 9,598,703 B2 | 3/2017 | Garcia et al. |
| 9,677,089 B2 | 6/2017 | Gao et al. |
| 9,737,618 B2 | 8/2017 | Wilson et al. |
| 9,856,539 B2 | 1/2018 | Schaffer et al. |
| 9,879,279 B2 | 1/2018 | Chen |
| 9,879,282 B2 | 1/2018 | Chen |
| 9,884,071 B2 | 2/2018 | Wilson et al. |
| 10,000,772 B2 | 6/2018 | Doudna et al. |
| 10,017,746 B2 | 7/2018 | Sheldon et al. |
| 10,046,016 B2 | 8/2018 | Schaffer et al. |
| 10,113,167 B2 | 10/2018 | Doudna et al. |
| 10,161,011 B2 | 12/2018 | Akashika et al. |
| 10,202,657 B2 | 2/2019 | Schaffer et al. |
| 10,214,566 B2 | 2/2019 | Schaffer et al. |
| 10,214,730 B2 | 2/2019 | Bahou et al. |
| 10,214,785 B2 | 2/2019 | Schaffer et al. |
| 10,227,611 B2 | 3/2019 | Doudna et al. |
| 10,265,417 B2 | 4/2019 | Wilson et al. |
| 10,266,846 B2 | 4/2019 | Gao et al. |
| 10,294,452 B2 | 5/2019 | He |

(Continued)

FOREIGN PATENT DOCUMENTS

WO    WO 2017/112948    6/2017

OTHER PUBLICATIONS

Adamson-Small, L et al. (2017) "*Sodium Chloride Enhances Recombinant Adeno-Associated Virus Production in a Serum-Free Suspension Manufacturing Platform Using the Herpes Simplex Virus System*," Hum. Gene Ther. Meth. 28(1):1-14.

Auricchio, A. et al. (2001) "*Isolation of Highly Infectious and Pure Adeno-Associated Virus Type 2 Vectors With a Single-Step Gravity-Flow Column*," Hum. Gene Ther. 12:71-76.

Ayuso, E. (2016) "*Manufacturing of Recombinant Adeno-Associated Viral Vectors: New Technologies Are Welcome*," Methods & Clinical Development 3: 15049 (pp. 1-3).

Balakrishnan, B. et al. (2014) "*Basic Biology of Adeno-Associated Virus (AAV) Vectors Used in Gene Therapy*," Curr. Gene Ther. 14(2):86-100.

Ben-Israel, H. et al. (2002) "*Adenovirus and Cell Cycle Control*," Front. Biosci. 7:d1369-d1395.

(Continued)

*Primary Examiner* — Titilayo Moloye
(74) *Attorney, Agent, or Firm* — Jeffrey I. Auerbach; AuerbachSchrot LLC

(57) ABSTRACT

The present invention is directed to methods for increasing the efficiencies with which recombinant adeno-associated virus (rAAV) are packaged, so as to increase their production titers. More specifically, the invention relates to a method for increasing the production titer of rAAV by transfected cells by increasing the ionic strength of the cell culture media through the administration of additional ions.

20 Claims, 13 Drawing Sheets

Specification includes a Sequence Listing.

(56) References Cited

U.S. PATENT DOCUMENTS

| | | | |
|---|---|---|---|
| 10,301,650 B2 | 5/2019 | Gao et al. | |
| 2005/0266567 A1 | 12/2005 | Atkinson et al. | |
| 2008/0076912 A1* | 3/2008 | Takkellapati | C12N 15/101 536/25.4 |

OTHER PUBLICATIONS

Berns, K. I. et al. (2017) "*AAV: An Overview of Unanswered Questions*," Human Gene Ther. 28(4):308-313.

Berry, G.E. et al. (2016) "*Cellular Transduction Mechanisms Of Adeno-Associated Viral Vectors*," Curr. Opin. Virol. 21:54-60.

Blessing, D. et al. (2016) "*Adeno-Associated Virus and Lentivirus Vectors: A Refined Toolkit for the Central Nervous System*," 21:61-66.

Brument, N. et al. (2002) "*A Versatile and Scalable Two-Step Ion-Exchange Chromatography Process for the Purification of Recombinant Adeno-Associated Virus Serotypes-2 and -5*," Mol. Ther. 6:678-686.

Büning, H. et al. (2019) "*Capsid Modifications for Targeting and Improving the Efficacy of AAV Vectors*," Mol. Ther. Meth. Clin. Devel. 12:p. 248-p. 265.

Cao, M. et al. (2014) "*The X Gene Of Adeno-Associated Virus 2 (AAV2) Is Involved in Viral DNA Replication*," PLoS One 9, e104596:1-10.

Chiorini, J.A. et al. (1997) "*Cloning of Adeno-Associated Virus Type 4 (AAV4) and Generation of Recombinant AAV4 Particles*," J. Virol. 71(9):6823-6833.

Chopra, A. (2007) "*Recombinant Adenovirus With Enhanced Green Fluorescent Protein*," In: Molecular Imaging and Contrast Agent Database (MICAD) [Internet]. Bethesda (MD): National Center for Biotechnology Information (pp. 1-5).

Cinelli, R.A. et al. (2000) "*The Enhanced Green Fluorescent Protein As a Tool for the Analysis of Protein Dynamics and Localization: Local Fluorescence Study At the Single-Molecule Level*," Photochem. Photobiol. 71(6):771-776.

Clément, N. et al. (2016) "*Manufacturing of Recombinant Adeno-Associated Viral Vectors for Clinical Trials*," Meth. Clin. Develop. 3:16002:1-7.

Colella, P. et al. (2018) "*Emerging Issues in AAV-Mediated In Vivo Gene Therapy*," Molec. Ther. Meth. Clin. Develop. 8:87-104.

Davidoff, A.M. et al. (2004) "*Purification of Recombinant Adeno-Associated Virus Type 8 Vectors by Ion Exchange Chromatography Generates Clinical Grade Vector Stock*," J. Virol. Methods 121:209-215.

Duan, D. (2016) "*Systemic Delivery Of Adeno-Associated Viral Vectors*," Curr. Opin. Virol. 21:16-25.

During, M.J. et al. (1998) "*In Vivo Expression of Therapeutic Human Genes for Dopamine Production in the Caudates Of MPTP-Treated Monkeys Using an AAV Vector*," Gene The. 5:820-827.

Durocher, Y. et al. (2007) "*Scalable Serum-Free Production of Recombinant Adeno-Associated Virus Type 2 by Transfection of 293 Suspension Cells*," J. Virol. Meth. 144:32-40.

Egelie, K.J. et al. (2016) "*The Emerging Patent Landscape of CRISPR—Cas Gene Editing Technology*," Nature Biotechnol. 34(10):1025-1031.

Ferreira, V. et al. (2014) "*Immune Responses to AAV-Vectors, The Glybera Example From Bench to Bedside*" Front. Immunol. 5(82):1-15.

François, A. et al. (2018) "*Accurate Titration of Infectious AAV Particles Requires Measurement of Biologically Active Vector Genomes and Suitable Controls*," Molec. Ther. Meth. Clin. Develop. 10:223-236.

Gambotto, A. et al. (2000) "*Immunogenicity of Enhanced Green Fluorescent Protein (EGFP) in BALB/C Mice: Identification Of An H2-Kd-Resfricted CTL Epitope*," Gene Ther. 7(23):2036-2040.

Gao, G.P. et al. (2002) "*Novel Adeno Associated Viruses From Rhesus Monkeys As Vectors for Human Gene Therapy*," Proc. Natl. Acad. Sci. (U.S.A.) 99(18):11854-11859.

Ghosh, A. et al. (2007) "*Expanding Adeno-Associated Viral Vector Capacity: A Tale of Two Vectors*," Biotechnol. Genet. Eng. Rev. 24:165-177.

Grieger, J.C. et al. (2012) "*Adeno-Associated Virus Vectorology, Manufacturing, and Clinical Applications*," Meth. Enzymol. 507:229-254.

Grimm, D. et al. (1998) "*Novel Tools for Production and Purification of Recombinant Adeno-Associated Virus Vectors*," Hum. Gene Ther. 9:2745-2760.

Hastie, E. et al. (2015) "*Adeno-Associated Virus at 50: A Golden Anniversary of Discovery, Research, and Gene Therapy Success—A Personal Perspective*," Human Gene Ther. 26:257-265.

Hauck, B. et al. (2003) "*Generation and Characterization of Chimeric Recombinant AAV Vectors*," Mol. Ther. 7:419-425.

Hocquemiller, M. et al. (2016) "*Adeno-Associated Virus-Based Gene Therapy for CNS Diseases*," Hum. Gene Ther. 27(7):478-496.

Hoeben, R.C. et al. (2013) "*Adenovirus DNA Replication*," Cold Spring Barb. Perspect. Biol. 5:a013003 (pp. 1-11).

Johnson, F.B. et al. (1972) "*Immunological Reactivity of Antisera Prepared Against the Sodium Dodecyl Sulfate-Treated Structural Polypeptides of Adenovirus-Associated Virus*," J. Virol. 9(6):1017-1026.

Kay, M. et al. (2017) "*Future of rAAV Gene Therapy: Platform for RNAi, Gene Editing and Beyond*," Human Gene Ther. 28:361-372.

Kotterman, M.A. et al. (2014) "*Engineering Adeno-Associated Viruses for Clinical Gene Therapy*," Nat. Rev. Genet. 15(7):445-451.

Kwon, I. et al. (2007) "*Designer Gene Delivery Vectors: Molecular Engineering and Evolution of Adeno-Associated Viral Vectors for Enhanced Gene Transfer*," Pharm. Res. 25(3):489-499.

Lackner, D.F. et al. (2002) "*Studies of the Mechanism of Transactivation of the Adeno-Associated Virus p19 Promoter by Rep Protein*," J. Virol. 76(16):8225-8235.

Le, H.T. et al. (2005) "*Utility of Pegylated Recombinant Adeno-Associated Viruses for Gene Transfer*," J. Control. Release 108:161-177.

Lee, G.K. et al. (2005) "*PEG Conjugation Moderately Protects Adeno-Associated Viral Vectors Against Antibody Neutralization*," Biotechnol. Bioeng. 92:24-34.

Lino, C.A. et al. (2018) "*Delivering CRISPR: A Review of the Challenges and Approaches*," Drug Deliv. 25(1):1234-1237.

Lisowski, L. et al. (2015) "*Adeno-Associated Virus Serotypes for Gene Therapeutics*," 24:59-67.

Liu, Q. et al. (2014) "*Neutralizing Antibodies Against AAV2, AAV5 and AAV8 in Healthy and HIV-1-Infected Subjects in China: Implications for Gene Therapy Using AAV Vectors*," Gene Ther. 21:732-738.

Lock, M. et al. (2010) "*Rapid, Simple, and Versatile Manufacturing of Recombinant Adeno-Associated Viral Vectors at Scale*," Hum. Gene Ther. 21:1259-1271.

Lykken, E.A. et al. (2018) "*Recent Progress and Considerations for AAV Gene Therapies Targeting the Central Nervous System*," J. Neurodevelop. Dis. 10:16:1-10.

Matsushita, T. et al. (1998) "*Adeno-Associated Virus Vectors Can Be Efficiently Produced Without Helper Virus*," Gene Ther. 5:938-945.

McClements, M.E. et a. (2017) "*Adeno-associated Virus (AAV) Dual Vector Strategies for Gene Therapy Encoding Large Transgenes*," Yale J. Biol. Med. 90:611-623.

Monahan, p. E et al. (2000) "*AAV Vectors: Is Clinical Success on the Horizon?*," Gene Ther. 7:24-30.

Naso, M.F. et al. (2017) "*Adeno-Associated Virus (AAV) as a Vector for Gene Therapy*," BioDrugs 31:317-334.

Ogasawara, Y. et al. (1998) "*The Use of Heterologous Promoters for Adeno-Associated Virus (AAV) Protein Expression in AAV Vector Production*," Microbiol. Immunol. 42(3):177-185.

Penaud-Budloo, M. et al. (2018) "*Pharmacology of Recombinant Adeno-associated Virus Production*," Molec. Ther. Meth. Clin. Develop. 8:166-180.

Rabinowitz, I.E. et al. (2004) "*Crossdressing the Virion: The Transcapsidation Of Adeno-Associated Virus Serotypes Functionally Defines Subgroups*," J. Virol. 78:4421-4432.

Rastall, D.P.W. (2017) "*Current and Future Treatments for Lysosomal Storage Disorders*," Curr. Treat Options Neurol. 19(12):45.

(56) References Cited

OTHER PUBLICATIONS

Salganik, M. et al. (2015) "*Adeno-Associated Virus As a Mammalian DNA Vector*," Microbiol. Spectr. 3(4):1-32.
Santiago-Ortiz, J.L. (2016) "*Adeno-Associated Virus (AAV) Vectors in Cancer Gene Therapy*," J. Control Release 240:287-301.
Smith, J.K. et al. (2018) "*Creating an Arsenal Of Adeno-Associated Virus (AAV) Gene Delivery Stealth Vehicles*," PLoS Pathog. 14(5):1-6.
Smith, R.H. et al. (2009) "*A Simplified Baculovirus-AAV Expression Vector System Coupled With One-Step Affinity Purification Yields High-Titer rAAV Stocks From Insect Cells*," Mol. Ther. 17:1888-1896.
Tsien, R.Y. (1998) "*The Green Fluorescent Protein*," Annu. Rev. Biochem. 67:509-544.
Van Vliet K.M. et al. (2008) *The Role of the Adeno-Associated Virus Capsid in Gene Transfer*. In: Drug Delivery Systems, Jain, K.K. (eds.), Meth. Molec. Biol. 437:51-91.
Vandamme, C. et al. (2017) "*Unraveling the Complex Story of Immune Responses to AAV Vectors Trial After Trial*," Hum. Gene. Ther. 28(11):1061-1074.
Weitzman, M.D. (2005) "*Functions of the Adenovirus E4 Proteins and Their Impact on Viral Vectors*," Front. Biosci. 10:1106-1117.
Weitzman, M.D. (2006) "*The Parvovirus Life Cycle: An Introduction to Molecular Interactions Important for Infection*," In: Kerr, J.R. et al. (Eds.) Parvoviruses, Hodder Arnold, London, UK (pp. 143-156).
Wu, Z. et al. (2010) "*Effect of Genome Size on AAV Vector Packaging*," Molec. Ther. 18:80-86.
Yao, T et al. (2017) "*Animal-Cell Culture Media: History, Characteristics, and Current Issues*," Reproduc. Med. Biol. 16(2): 99-117.
Zen, Z. et al. (2004) "*Infectious Titer Assay for Adeno-Associated Virus Vectors With Sensitivity Sufficient to Detect Single Infectious Events*," Hum. Gene Ther. 15:709-715.
Zinn, E. et al. (2014) "*Adeno-Associated Virus: Fit to Serve*," Curr. Opin. Virol. 0:90-97.
Zolotukhin, S. et al. (1999) "*Recombinant Adeno-Associated Virus Purification Using Novel Methods Improves Infectious Titer and Yield*," Gene Ther. 6:973-985.
Zolotukhin, S. et al. (2002) "*Production and Purification of Serotype 1, 2, and 5 Recombinant Adeno-Associated Viral Vectors*," Methods 28:158-167.
Rodrigues, G.A. et al. (2019) "*Pharmaceutical Development of AAV-Based Gene Therapy Products for the Eye*," Pharm. Res. 36: 29 (pp. 1-20).
Gagnon, P. (2019) "*Accelerating AAV to the Clinic with Purification Improvements*," Genetic Engineer. Biotechnol. News 39(12) pp. 1-10.

\* cited by examiner

SEQUENCE LISTING

```
<160> NUMBER OF SEQ ID NOS: 4

<210> SEQ ID NO 1
<211> LENGTH: 7415
<212> TYPE: DNA
<213> ORGANISM: Artificial Sequence
<220> FEATURE:
<223> OTHER INFORMATION: Coding Strand of Plasmid pAAV-RC2

<400> SEQUENCE: 1
ccgggccccc cctcgaggtc gacggtatcg ggggagctcg cagggtctcc attttgaagc      60
gggaggtttg aacgcgcagc cgccatgccg gggttttacg agattgtgat taaggtcccc     120
agcgaccttg acgagcatct gcccggcatt tctgacagct ttgtgaactg ggtggccgag     180
aaggaatggg agttgccgcc agattctgac atggatctga atctgattga gcaggcaccc     240
ctgaccgtgg ccgagaagct gcagcgcgac tttctgacgg aatggcgccg tgtgagtaag     300 gcccccggagg ctcttttctt tgtgcaattt gagaagggag agagctactt ccacatgcac     360
gtgctcgtgg aaaccaccgg ggtgaaatcc atggttttgg gacgtttcct gagtcagatt     420
cgcgaaaaac tgattcagag aatttaccgc gggatcgagc cgactttgcc aaactggttc     480
gcggtcacaa agaccagaaa tggcgccgga ggcgggaaca aggtggtgga tgagtgctac     540
atccccaatt acttgctccc caaaacccag cctgagctcc agtgggcgtg gactaatatg     600
gaacagtatt taagcgcctg tttgaatctc acggagcgta aacggttggt ggcgcagcat     660
ctgacgcacg tgtcgcagac gcaggagcag aacaaagaga atcagaatcc caattctgat     720
gcgccggtga tcagatcaaa aacttcagcc aggtacatgg agctggtcgg gtggctcgtg     780
gacaagggga ttacctcgga gaagcagtgg atccaggagg accaggcctc atacatctcc     840
ttcaatgcgg cctccaactc gcggtcccaa atcaaggctg ccttggacaa tgcgggaaag     900
attatgagcc tgactaaaac cgccccccgac tacctggtgg gccagcagcc cgtggaggac     960
atttccagca atcggattta taaattttg gaactaaacg ggtacgatcc caatatgcg     1020 gcttccgtct ttctgggatg ggccacgaaa aagttcggca agaggaacac catctggctg    1080
tttgggcctg caactaccgg gaagaccaac atcgcggagg ccatagccca cactgtgccc    1140
ttctacgggt gcgtaaactg gaccaatgag aactttccct tcaacgactg tgtcgacaag    1200
atggtgatct ggtgggagga ggggaagatg accgccaagg tcgtggagtc ggccaaagcc    1260
attctcggag gaagcaaggt gcgcgtggac cagaaatgca agtcctcggc ccagatagac    1320
ccgactcccg tgatcgtcac ctccaacacc aacatgtgcg ccgtgattga cgggaactca    1380
```

```
acgaccttcg aacaccagca gccgttgcaa gaccggatgt tcaaatttga actcacccgc    1440
cgtctggatc atgactttgg gaaggtcacc aagcaggaag tcaaagactt tttccggtgg    1500
gcaaaggatc acgtggttga ggtggagcat gaattctacg tcaaaaaggg tggagccaag    1560
aaaagacccg cccccagtga cgcagatata agtgagccca acgggtgcg cgagtcagtt    1620 gcgcagccat cgacgtcaga cgcggaagct tcgatcaact acgcagacag gtaccaaaac    1680
aaatgttctc gtcacgtggg catgaatctg atgctgtttc cctgcagaca atgcgagaga    1740
atgaatcaga attcaaatat ctgcttcact cacggacaga aagactgttt agagtgcttt    1800
cccgtgtcag aatctcaacc cgtttctgtc gtcaaaaagg cgtatcagaa actgtgctac    1860
attcatcata tcatgggaaa ggtgccagac gcttgcactg cctgcgatct ggtcaatgtg    1920
gatttggatg actgcatctt tgaacaataa atgatttaaa tcaggtatgg ctgccgatgg    1980
ttatcttcca gattggctcg aggacactct ctctgaagga ataagacagt ggtggaagct    2040
caaacctggc ccaccaccac caaagcccgc agagcggcat aaggacgaca gcagggggtct    2100 tgtgcttcct gggtacaagt acctcggacc cttcaacgga ctcgacaagg gagagccggt    2160
caacgaggca gacgccgcgg ccctcgagca cgacaaagcc tacgaccggc agctcgacag    2220
cggagacaac ccgtacctca gtacaacca cgccgacgcg gagtttcagg agcgccttaa    2280
agaagatacg tcttttgggg gcaacctcgg acgagcagtc ttccaggcga aaaagagggt    2340
tcttgaacct ctgggcctgg ttgaggaacc tgttaagacg gctccgggaa aaaagaggcc    2400
ggtagagcac tctcctgtgg agccagactc ctcctcggga accggaaagg cgggccagca    2460
gcctgcaaga aaaagattga attttggtca gactggagac gcagactcag tacctgaccc    2520
ccagcctctc ggacagccac cagcagcccc ctctggtctg gaactaata cgatggctac    2580 aggcagtggc gcaccaatgg cagacaataa cgagggcgcc gacggagtgg gtaattcctc    2640
gggaaattgg cattgcgatt ccacatggat gggcgacaga gtcatcacca ccagcacccg    2700
aacctgggcc ctgcccacct acaacaacca cctctacaaa caaatttcca gccaatcagg    2760
agcctcgaac gacaatcact actttggcta cagcaccct tgggggtatt ttgacttcaa    2820
cagattccac tgccactttt caccacgtga ctggcaaaga ctcatcaaca caactgggg    2880 attccgaccc aagagactca acttcaagct ctttaacatt caagtcaaag aggtcacgca    2940
gaatgacggt acgacgacga ttgccaataa ccttaccagc acggttcagg tgtttactga    3000
ctcggagtac cagctcccgt acgtcctcgg ctcggcgcat caaggatgcc tcccgccgtt    3060
cccagcagac gtcttcatgg tgccacagta tggataccctc accctgaaca acggagtca    3120 ggcagtagga cgctcttcat tttactgcct ggagtacttt ccttctcaga tgctgcgtac    3180
cggaaacaac tttaccttca gctacacttt tgaggacgtt cctttccaca gcagctacgc    3240
tcacagccag agtctggacc gtctcatgaa tcctctcatc gaccagtacc tgtattactt    3300
gagcagaaca aacactccaa gtggaaccac cacgcagtca aggcttcagt tttctcaggc    3360
cggagcgagt gacattcggg accagtctag gaactggctt cctggaccct gttaccgcca    3420
gcagcgagta tcaaagacat ctgcggataa caacaacagt gaatactcgt ggactggagc    3480
taccaagtac cacctcaatg gcagagactc tctggtgaat ccgggcccgg ccatggcaag    3540
ccacaaggac gatgaagaaa agttttttcc tcagagcggg gttctcatct ttgggaagca    3600
aggctcagag aaaacaaatg tggacattga aaaggtcatg attacagacg aagaggaaat    3660
caggacaacc aatcccgtgg ctacggagca gtatggttct gtatctacca acctccagag    3720
aggcaacaga caagcagcta ccgcagatgt caacacacaa ggcgttcttc aggcatggt    3780
```

```
ctggcaggac agagatgtgt accttcaggg gcccatctgg gcaaagattc cacacacgga    3840
cggacatttt caccccctctc ccctcatggg tggattcgga cttaaacacc ctcctccaca   3900
gattctcatc aagaacaccc cggtacctgc gaatccttcg accaccttca gtgcggcaaa   3960
gtttgcttcc ttcatcacac agtactccac gggacaggtc agcgtggaga tcgagtggga   4020
gctgcagaag gaaaacagca aacgctggaa tcccgaaatt cagtacactt ccaactacaa   4080
caagtctgtt aatgtggact ttactgtgga cactaatggc gtgtattcag agcctcgccc   4140
cattggcacc agatacctga ctcgtaatct gtaattgctt gttaatcaat aaaccgttta   4200
attcgtttca gttgaacttt ggtctctgcg tatttctttc ttatctagtt tccatgctct   4260
aggatccact agtaacggcc gccagtgtgc tggaattcgg cttttgtagtt aatgattaac   4320 ccgccatgct acttatctac gtagccatgc tctagaggtc ctgtattaga ggtcacgtga   4380
gtgttttgcg acattttgcg acaccatgtg gtcacgctgg gtatttaagc ccgagtgagc   4440
acgcagggtc tccattttga agcgggaggt ttgaacgcgc agccgccaag ccgaattctg   4500
cagatatcca aacactggcg gccgctcgac tagagcggcc gccaccgcgg tggagctcca   4560
gcttttgttc cctttagtga gggttaattg cgcgcttggc gtaatcatgg tcatagctgt   4620
ttcctgtgtg aaattgttat ccgctcacaa ttccacacaa catacgagcc ggaagcataa   4680
agtgtaaagc ctggggtgcc taatgagtga gctaactcac attaattgcg ttgcgctcac   4740
tgcccgcttt ccagtcggga aacctgtcgt gccagctgca ttaatgaatc ggccaacgcg   4800
cggggagagg cggtttgcgt attgggcgct cttccgcttc ctcgctcact gactcgctgc   4860
gctcggtcgt tcggctgcgg cgagcggtat cagctcactc aaaggcggta atacggttat   4920
ccacagaatc aggggataac gcaggaaaga acatgtgagc aaaaggccag caaaaggcca   4980
ggaaccgtaa aaaggccgcg ttgctggcgt ttttccatag gctccgcccc cctgacgagc   5040
atcacaaaaa tcgacgctca agtcagaggt ggcgaaaccc gacaggacta taaagatacc   5100
aggcgtttcc ccctggaagc tccctcgtgc gctctcctgt tccgaccctg ccgcttaccg   5160
gatacctgtc cgcctttctc ccttcgggaa gcgtggcgct ttctcatagc tcacgctgta   5220
ggtatctcag ttcggtgtag tcgttcgct ccaagctggg ctgtgtgcac gaaccccccg   5280
ttcagcccga ccgctgcgcc ttatccggta actatcgtct tgagtccaac ccggtaagac   5340
acgacttatc gccactggca gcagccactg gtaacaggat tagcagagcg aggtatgtag   5400
gcggtgctac agagttcttg aagtggtggc ctaactacgg ctacactaga agaacagtat   5460
ttggtatctg cgctctgctg aagccagtta ccttcggaaa aagagttggt agctcttgat   5520
ccggcaaaca aaccaccgct ggtagcggtg ttttttttgt ttgcaagcag cagattacgc   5580
gcagaaaaaa aggatctcaa gaagatcctt tgatctttc tacggggtct gacgctcagt   5640
ggaacgaaaa ctcacgttaa gggattttgg tcatgagatt atcaaaaagg atcttcacct   5700
agatcctttt aaattaaaaa tgaagtttta aatcaatcta agtatatat gagtaaactt   5760 ggtctgacag ttaccaatgc ttaatcagtg aggcacctat ctcagcgatc tgtctatttc   5820
gttcatccat agttgcctga ctccccgtcg tgtagataac tacgacacgg gagggcttac   5880
catctggccc cagtgctgca atgataccgc gagacccacg ctcaccggct ccagatttat   5940
cagcaataaa ccagccagcc ggaagggccg agcgcagaag tggtcctgca actttatccg   6000
cctccatcca gtctattaat tgttgccggg aagctagagt aagtagttcg ccagttaata   6060
gtttgcgcaa cgttgttgcc attgctacag gcatcgtggt gtcacgctcg tcgtttggta   6120
```

```
tggcttcatt cagctccggt tcccaacgat caaggcgagt tacatgatcc cccatgttgt    6180
gcaaaaaagc ggttagctcc ttcggtcctc cgatcgttgt cagaagtaag ttggccgcag    6240
tgttatcact catggttatg gcagcactgc ataattctct tactgtcatg ccatccgtaa    6300
gatgcttttc tgtgactggt gagtactcaa ccaagtcatt ctgagaatag tgtatgcggc    6360
gaccgagttg ctcttgcccg gcgtcaatac gggataatac cgcgccacat agcagaactt    6420
taaaagtgct catcattgga aaacgttctt cggggcgaaa actctcaagg atcttaccgc    6480
tgttgagatc cagttcgatg taacccactc gtgcacccaa ctgatcttca gcatctttta    6540
ctttcaccag cgtttctggg tgagcaaaaa caggaaggca aaatgccgca aaaaagggaa    6600
taagggcgac acggaaatgt tgaatactca tactcttcct ttttcaatat tattgaagca    6660
tttatcaggg ttattgtctc atgagcggat acatatttga atgtatttag aaaaataaac    6720
aaataggggt tccgcgcaca tttccccgaa aagtgccacc taaattgtaa gcgttaatat    6780
tttgttaaaa ttcgcgttaa attttttgtta aatcagctca ttttttaacc aataggccga    6840
aatcggcaaa atcccttata aatcaaaaga atagaccgag atagggttga gtgttgttcc    6900
agtttggaac aagagtccac tattaaagaa cgtggactcc aacgtcaaag ggcgaaaaac    6960
cgtctatcag ggcgatggcc cactacgtga accatcaccc taatcaagtt ttttggggtc    7020
gaggtgccgt aaagcactaa atcggaaccc taaagggagc ccccgattta gagcttgacg    7080
gggaaagccg gcgaacgtgg cgagaaagga agggaagaaa gcgaaaggag cgggcgctag    7140
ggcgctggca agtgtagcgg tcacgctgcg cgtaaccacc acccgccgcg cttaatgc     7200 gccgctacag ggcgcgtccc attcgccatt caggctgcgc aactgttggg aagggcgatc    7260
ggtgcgggcc tcttcgctat tacgccagct ggcgaaaggg ggatgtgctg caaggcgatt    7320
aagttgggta acgccagggt tttcccagtc acgacgttgt aaaacgacgg ccagtgagcg    7380
cgcgtaatac gactcactat agggcgaatt gggta                              7415
```

<210> SEQ ID NO 2
<211> LENGTH: 11569
<212> TYPE: DNA
<213> ORGANISM: Artificial Sequence
<220> FEATURE:
<223> OTHER INFORMATION: Coding Strand of Plasmid pHelper-Kan

<400> SEQUENCE: 2

```
ggtacccaac tccatgctta acagtcccca ggtacagccc accctgcgtc gcaaccagga     60
acagctctac agcttcctgg agcgccactc gccctacttc cgcagccaca gtgcgcagat    120
taggagcgcc acttcttttt gtcacttgaa aaacatgtaa aaataatgta ctaggagaca    180
ctttcaataa aggcaaatgt ttttatttgt acactctcgg gtgattattt accccccacc    240
cttgccgtct gcgccgttta aaaatcaaag gggttctgcc gcgcatcgct atgcgccact    300
ggcagggaca cgttgcgata ctggtgttta gtgctccact aaactcagg cacaaccatc    360 cgcggcagct cggtgaagtt ttcactccac aggctgcgca ccatcaccaa cgcgtttagc    420
aggtcgggcg ccgatatctt gaagtcgcag ttggggcctc cgccctgcgc gcgcgagttg    480
cgatacacag ggttgcagca ctggaacact atcagcgccg gtggtgcac gctgccagc     540 acgctcttgt cggagatcag atccgcgtcc aggtcctccg cgttgctcag ggcgaacgga    600
gtcaactttg gtagctgcct tcccaaaaag ggtgcatgcc caggctttga gttgcactcg    660
caccgtagtg gcatcagaag gtgaccgtgc ccggtctggg cgttaggata cagcgcctgc    720
atgaaagcct tgatctgctt aaaagccacc tgagcctttg cgccttcaga gaagaacatg    780
```

```
ccgcaagact tgccggaaaa ctgattggcc ggacaggccg cgtcatgcac gcagcacctt      840
gcgtcggtgt tggagatctg caccacattt cggccccacc ggttcttcac gatcttggcc      900
ttgctagact gctccttcag cgcgcgctgc ccgttttcgc tcgtcacatc catttcaatc      960
acgtgctcct tatttatcat aatgctcccg tgtagacact taagctcgcc ttcgatctca     1020
gcgcagcggt gcagccacaa cgcgcagccc gtgggctcgt ggtgcttgta ggttacctct     1080
gcaaacgact gcaggtacgc ctgcaggaat cgccccatca tcgtcacaaa ggtcttgttg     1140
ctggtgaagg tcagctgcaa cccgcggtgc tcctcgttta gccaggtctt gcatacggcc     1200
gccagagctt ccacttggtc aggcagtagc ttgaagtttg cctttagatc gttatccacg     1260
tggtacttgt ccatcaacgc gcgcgcagcc tccatgccct tctcccacgc agacacgatc     1320
ggcaggctca gcgggtttat caccgtgctt tcactttccg cttcactgga ctcttccttt     1380
tcctcttgcg tccgcatacc ccgcgccact gggtcgtctt cattcagccg ccgcaccgtg     1440
cgcttacctc ccttgccgtg cttgattagc accggtgggt tgctgaaacc caccatttgt     1500
agcgccacat cttctctttc ttcctcgctg tccacgatca cctctgggga tggcgggcgc     1560
tcgggcttgg gagaggggcg cttctttttc tttttggacg caatggccaa atccgccgtc     1620
gaggtcgatg gccgcgggct gggtgtgcgc ggcaccagcg catcttgtga cgagtcttct     1680
tcgtcctcgg actcgagacg ccgcctcagc cgctttttg ggggcgcgcg gggaggcggc     1740
ggcgacggcg acggggacga cacgtcctcc atggttggtg gacgtcgcgc cgcaccgcgt     1800
ccgcgctcgg gggtggtttc gcgctgctcc tcttcccgac tggccatttc cttctcctat     1860
aggcagaaaa agatcatgga gtcagtcgag aaggaggaca gcctaaccgc cccctttgag     1920
ttcgccacca ccgcctccac cgatgccgcc aacgcgccta ccaccttccc cgtcgaggca     1980
cccccgcttg aggaggagga agtgattatc gagcaggacc caggttttgt aagcgaagac     2040
gacgaggatc gctcagtacc aacagaggat aaaaagcaag accaggacga cgcagaggca     2100
aacgaggaac aagtcgggcg gggggaccaa aggcatggcg actacctaga tgtgggagac     2160
gacgtgctgt tgaagcatct gcagcgccag tgcgccatta tctgcgacgc gttgcaagag     2220
cgcagcgatg tgcccctcgc catagcggat gtcagccttg cctacgaacg ccacctgttc     2280
tcaccgcgcg tacccccccaa acgccaagaa aacggcacat gcgagcccaa cccgcgcctc     2340
aacttctacc ccgtatttgc cgtgccagag gtgcttgcca cctatcacat ctttttccaa     2400
aactgcaaga taccctatc ctgccgtgcc aaccgcagcc gagcggacaa gcagctggcc     2460
ttgcggcagg gcgctgtcat acctgatatc gcctcgctcg acgaagtgcc aaaaatcttt     2520
gagggtcttg gacgcgacga gaaacgcgcg gcaaacgctc tgcaacaaga aaacagcgaa     2580
aatgaaagtc actgtggagt gctggtggaa cttgagggtg acaacgcgcg cctagccgtg     2640
ctgaaacgca gcatcgaggt cacccacttt gcctacccgg cacttaaccct acccccccaag     2700 gttatgagca cagtcatgag cgagctgatc gtgcgccgtg cacgacccct ggagagggat     2760
gcaaacttgc aagaacaaac cgaggagggc ctacccgcag ttggcgatga gcagctggcg     2820
cgctggcttg agacgcgcga gcctgccgac ttggaggagc gacgcaagct aatgatggcc     2880
gcagtgcttg ttaccgtgga gcttgagtgc atgcagcggt tctttgctga cccggagatg     2940
cagcgcaagc tagaggaaac gttgcactac acctttcgcc agggctacgt gcgccaggcc     3000
tgcaaaattt ccaacgtgga gctctgcaac ctggtctcct accttggaat tttgcacgaa     3060
aaccgcctcg ggcaaaacgt gcttcattcc acgctcaagg gcgaggcgcg ccgcgactac     3120
```

```
gtccgcgact gcgtttactt atttctgtgc tacacctggc aaacggccat gggcgtgtgg    3180
cagcaatgcc tggaggagcg caacctaaag gagctgcaga agctgctaaa gcaaaacttg    3240
aaggacctat ggacggcctt caacgagcgc tccgtggccg cgcacctggc ggacattatc    3300
ttccccgaac gcctgcttaa aaccctgcaa cagggtctgc cagacttcac cagtcaaagc    3360
atgttgcaaa actttaggaa ctttatccta gagcgttcag gaattctgcc cgccacctgc    3420
tgtgcgcttc ctagcgactt tgtgcccatt aagtaccgtg aatgccctcc gccgctttgg    3480
ggtcactgct accttctgca gctagccaac taccttgcct accactccga catcatggaa    3540
gacgtgagcg gtgacggcct actggagtgt cactgtcgct gcaacctatg caccccgcac    3600
cgctccctgg tctgcaattc gcaactgctt agcgaaagtc aaattatcgg tacctttgag    3660
ctgcagggtc cctcgcctga cgaaaagtcc gcggctccgg ggttgaaact cactccgggg    3720
ctgtggacgt cggcttacct tcgcaaattt gtacctgagg actaccacgc ccacgagatt    3780
aggttctacg aagaccaatc ccgcccgcca aatgcggagc ttaccgcctg cgtcattacc    3840
cagggccaca tccttggcca attgcaagcc atcaacaaag cccgccaaga gtttctgcta    3900
cgaaagggac gggggttta cctggacccc cagtccggcg aggagctcaa cccaatcccc    3960
ccgccgccgc agcccatca gcagccgcgg gcccttgctt cccaggatgg cacccaaaaa    4020
gaagctgcag ctgccgccgc cgccaccac ggacgaggag gaatactggg acagtcaggc    4080
agaggaggtt ttggacgagg aggagagat gatggaagac tgggacagcc tagacgaagc    4140
ttccgaggcc gaagaggtgt cagacgaaac accgtcaccc tcggtcgcat tccctcgcc    4200 ggcgccccag aaattggcaa ccgttcccag catcgctaca acctccgctc ctcaggcgcc    4260
gccggcactg cctgttcgcc gacccaaccg tagatgggac accactggaa ccagggccgg    4320
taagtctaag cagccgccgc cgttagccca agagcaacaa cagcgccaag gctaccgctc    4380
gtggcgcggg cacaagaacg ccatagttgc ttgcttgcaa gactgtgggg gcaacatctc    4440
cttcgcccgc gctttcttc tctaccatca cggcgtggcc ttccccgta acatcctgca    4500 ttactaccgt catctctaca gcccctactg caccggcggc agcggcagcg gcagcaacag    4560
cagcggtcac acagaagcaa aggcgaccgg ataagcaagac tctgacaaag cccaagaaat    4620
ccacagcggc ggcagcagca ggaggaggag cgctgcgtct ggcgcccaac gaacccgtat    4680
cgacccgcga gcttagaaat aggatttttc ccactctgta tgctatattt caacaaagca    4740
ggggccaaga acaagagctg aaaataaaaa acaggtctct gcgctccctc acccgcagct    4800
gcctgtatca caaagcgaa gatcagcttc ggcgcacgct ggaagacgcg gaggctctct    4860
tcagcaaata ctgcgcgctg actcttaagg actagtttcg cgcccttttct caaatttaag    4920 cgcgaaaact acgtcatctc cagcggccac acccggcgcc agcacctgtc gtcagcgcca    4980
ttatgagcaa ggaaattccc acgccctaca tgtggagtta ccagccacaa atgggacttg    5040
cggctggagc tgcccaagac tactcaaccc gaataaacta catgagcgcg gaccccaca    5100 tgatatcccg ggtcaacgga atccgcgccc accgaaaccg aattctcctc gaacaggcgg    5160
ctattaccac cacacctcgt aataaccta atcccgtag ttggcccgct gccctggtgt    5220
accaggaaag tccgctccc accactgtgg tacttcccag agacgcccag gccgaagttc    5280
agatgactaa ctcaggggcg cagcttgcgg gcggctttcg tcacagggtg cggtcgcccg    5340
ggcgttttag gcggagtaa cttgcatgta ttgggaattg tagtttttt aaaatgggaa    5400 gtgacgtatc gtgggaaaac ggaagtgaag atttgaggaa gttgtgggtt ttttggcttt    5460
cgtttctggg cgtaggttcg cgtgcggttt tctgggtgtt ttttgtggac tttaaccgtt    5520
```

```
acgtcatttt ttagtcctat atatactcgc tctgtacttg gccctttta cactgtgact   5580 gattgagctg gtgccgtgtc gagtggtgtt ttttaatagg ttttttact ggtaaggctg   5640 actgttatgg ctgccgctgt ggaagcgctg tatgttgttc tggagcggga gggtgctatt   5700
ttgcctaggc aggagggttt ttcaggtgtt tatgtgtttt tctctcctat taattttgtt   5760
atacctccta tggggctgt aatgttgtct ctacgcctgc gggtatgtat tcccccgggc    5820
tatttcggtc gcttttagc actgaccgat gttaaccaac ctgatgtgtt taccgagtct   5880
tacattatga ctccggacat gaccgaggaa ctgtcggtgg tgcttttaa tcacggtgac    5940 cagttttttt acgtcacgc cggcatggcc gtagtccgtc ttatgcttat aagggttgtt    6000
tttcctgttg taagacaggc ttctaatgtt taaatgtttt ttttttttgtt attttatttt  6060 gtgtttaatg caggaacccg cagacatgtt tgagagaaaa atggtgtctt tttctgtggt   6120
ggttccggaa cttacctgcc tttatctgca tgagcatgac tacgatgtgc ttgcttttt    6180 gcgcgaggct ttgcctgatt ttttgagcag caccttgcat tttatatcgc cgcccatgca   6240
acaagcttac ataggggcta cgctggttag catagctccg agtatgcgtg tcataatcag   6300
tgtgggttct tttgtcatgg ttcctggcgg ggaagtggcc gcgctggtcc gtgcagacct   6360
gcacgattat gttcagctgg ccctgcgaag ggacctacgg gatcgcggta ttttgttaa    6420 tgttccgctt ttgaatctta tacaggtctg tgaggaacct gaatttttgc aatcatgatt   6480
cgctgcttga ggctgaaggt ggagggcgct ctggagcaga ttttttacaat ggccggactt  6540 aatattcggg atttgcttag agacatattg ataaggtggc gagatgaaaa ttatttgggc   6600
atggttgaag gtgctggaat gtttatagag gagattcacc ctgaagggtt tagcctttac   6660
gtccacttgg acgtgagggc agtttgcctt ttggaagcca ttgtgcaaca tcttacaaat   6720
gccattatct gttctttggc tgtagagttt gaccacgcca ccggagggga gcgcgttcac   6780
ttaatagatc ttcattttga ggttttggat aatcttttgg aataaaaaaa aaaaaacatg    6840
gttcttccag ctcttcccgc tcctcccgtg tgtgactcgc agaacgaatg tgtaggttgg    6900
ctgggtgtgg cttattctgc ggtggtggat gttatcaggg cagcggcgca tgaaggagtt   6960
tacatagaac ccgaagccag ggggcgcctg gatgctttga gagagtggat atactacaac   7020
tactacacag agcgagctaa gcgacgagac cggagacgca gatctgtttg tcacgcccgc   7080
acctggtttt gcttcaggaa atatgactac gtccggcgtt ccatttggca tgacactacg   7140
accaacacga tctcggttgt ctcggcgcac tccgtacagt agggatcgcc tacctccttt   7200
tgagacagag acccgcgcta ccatactgga ggatcatccg ctgctgcccg aatgtaacac   7260
tttgacaatg cacaacgtga gttacgtgcg aggtcttccc tgcagtgtgg gatttacgct   7320
gattcaggaa tgggttgttc cctgggatat ggttctgacg cggaggagc ttgtaatcct    7380 gaggaagtgt atgcacgtgt gcctgtgttg tgccaacatt gatatcatga cgagcatgat   7440
gatccatggt tacgagtcct gggctctcca ctgtcattgt tccagtcccg gttccctgca   7500
gtgcatagcc ggcgggcagg ttttggccag ctggtttagg atggtggtgg atggcgccat   7560
gtttaatcag aggtttatat ggtaccggga ggtggtgaat tacaacatgc caaaagaggt   7620
aatgtttatg tccagcgtgt ttatgagggg tcgccactta atctacctgc gcttgtggta   7680
tgatggccac gtgggttctg tggtccccgc catgagcttt ggatacagcg ccttgcactg   7740
tgggattttg aacaatattg tggtgctgtg ctgcagttac tgtgctgatt taagtgagat   7800
cagggtgcgc tgctgtgccc ggaggacaag gcgtctcatg ctgcgggcgg tgcgaatcat   7860
```

```
cgctgaggag accactgcca tgttgtattc ctgcaggacg gagcggcggc ggcagcagtt    7920
tattcgcgcg ctgctgcagc accaccgccc tatcctgatg cacgattatg actctacccc    7980
catgtaggcg tggacttccc cttcgccgcc cgttgagcaa ccgcaagttg gacagcagcc    8040
tgtggctcag cagctggaca cgacatgaa cttaagcgag ctgcccgggg agtttattaa    8100
tatcactgat gagcgtttgg ctcgacagga accgtgtgg aatataacac ctaagaatat    8160
gtctgttacc catgatatga tgcttttaa ggccagccgg ggagaaagga ctgtgtactc    8220
tgtgtgttgg gagggaggtg gcaggttgaa tactagggtt ctgtgagttt gattaaggta    8280
cggtgatcaa tataagctat gtggtggtgg ggctatacta ctgaatgaaa aatgacttga    8340
aattttctgc aattgaaaaa taaacacgtt gaaacataac atgcaacagg ttcacgattc    8400
tttattcctg ggcaatgtag gagaaggtgt aagagttggt agcaaaagtt tcagtggtgt    8460
attttccact ttcccaggac catgtaaaag acatagagta agtgcttacc tcgctagttt    8520
ctgtggattc actagaatcg atgtaggatg ttgcccctcc tgacgcggta ggagaagggg    8580
agggtgccct gcatgtctgc cgctgctctt gctcttgccg ctgctgagga gggggcgca    8640
tctgccgcag caccgatgc atctgggaaa agcaaaaaag gggctcgtcc ctgtttccgg    8700
aggaatttgc aagcggggtc ttgcatgacg gggaggcaaa cccccgttcg ccgcagtccg    8760
gccggcccga gactcgaacc gggggtcctg cgactcaacc cttggaaaat aaccctccgg    8820
ctacagggag cgagccactt aatgctttcg cttttccagcc taaccgctta cgccgcgcgc    8880
ggccagtggc caaaaagct agcgcagcag ccgccgcgcc tggaaggaag ccaaaaggag    8940
cgctcccccg ttgtctgacg tcgcacacct gggttcgaca cgcgggcggt aaccgcatgg    9000
atcacggcgg acggccggat ccggggttcg aaccccggtc gtccgccatg atacccttgc    9060
gaatttatcc accagaccac ggaagagtgc ccgcttacag gctctccttt tgcacggtct    9120
agagcgtcaa cgactgcgca cgcctcaccg gccagagcgt cccgaccatg gagcacttt    9180
tgccgctgcg caacatctgg aaccgcgtcc gcgactttcc gcgcgcctcc accaccgccg    9240
ccggcatcac ctggatgtcc aggtacatct acggattacg tcgacgttta aaccatatga    9300
tcagctcact caaaggcggt aatacggtta tccacagaat caggggataa cgcaggaaag    9360
aacatgtgag caaaaggcca gcaaaaggcc aggaaccgta aaaaggccgc gttgctggcg    9420
tttttccata ggctccgccc ccctgacgag catcacaaaa atcgacgctc aagtcagagg    9480
tggcgaaacc cgacaggact ataaagatac caggcgtttc ccctggaag ctccctcgtg    9540
cgctctcctg ttccgaccct gccgcttacc ggatacctgt ccgcctttct cccttcggga    9600
agcgtggcgc tttctcatag ctcacgctgt aggtatctca gttcggtgta ggtcgttcgc    9660
tccaagctgg gctgtgtgca cgaacccccc gttcagcccg accgctgcgc cttatccggt    9720
aactatcgtc ttgagtccaa cccggtaaga cacgacttat cgccactggc agcagccact    9780
ggtaacagga ttagcagagc gaggtatgta ggcggtgcta cagagttctt gaagtggtgg    9840
cctaactacg gctacactag aagaacagta tttggtatct gcgctctgct gaagccagtt    9900
accttcggaa aaagagttgg tagctcttga tccggcaaac aaaccaccgc tggtagcggt    9960
ggtttttttg tttgcaagca gcagattacg cgcagaaaaa aaggatctca agaagatcct   10020
ttgatctttt ctacggggtc tgacgctcag tggaacgaaa actcacgtta agggattttg   10080
gtcatgagat tatcaaaaag gatcttcacc tagatccttt taaattaaaa atgaagtttt   10140
aaatcaatct aaagtatata tgagtaaact tggtctgaca gtcagaagaa ctcgtcaaga   10200
aggcgataga aggcgatgcg ctgcgaatcg ggagcggcga taccgtaaag cacgaggaag   10260
```

```
cggtcagccc attcgccgcc aagctcttca gcaatatcac gggtagccaa cgctatgtcc    10320
tgatagcggt ccgccacacc cagccggcca cagtcgatga atccagaaaa gcggccattt    10380
tccaccatga tattcggcaa gcaggcatcg ccatgggtca cgacgagatc ctcgccgtcg    10440
ggcatgctcg ccttgagcct ggcgaacagt tcggctggcg cgagccctg atgctcttcg     10500 tccagatcat cctgatcgac aagaccggct tccatccgag tacgtgctcg ctcgatgcga    10560
tgtttcgctt ggtggtcgaa tgggcaggta gccggatcaa gcgtatgcag ccgccgcatt    10620
gcatcagcca tgatggatac tttctcggca ggagcaaggt gagatgacag gagatcctgc    10680
cccggcactt cgcccaatag cagccagtcc cttcccgctt cagtgacaac gtcgagtaca    10740
gctgcgcaag gaacgcccgt cgtggccagc cacgatagcc gcgctgcctc gtcttgcagt    10800
tcattcaggg caccggacag gtcggtcttg acaaaaagaa ccgggcgccc ctgcgctgac    10860
agccggaaca cggcggcatc agagcagccg attgtctgtt gtgcccagtc atagccgaat    10920
agcctctcca cccaagcggc cggagaacct gcgtgcaatc catcttgttc aatcatactc    10980 ttccttttc aatattattg aagcatttat cagggttatt gtctcatgag cggatacata    11040
tttgaatgta tttagaaaaa taaacaaata ggggttccgc gcacatttcc ccgaaaagtg    11100
ccacctaaat tgtaagcgtt aatattttgt taaaattcgc gttaaatttt tgttaaatca    11160 gctcatttt taaccaatag gccgaaatcg gcaaaatccc ttataaatca aagaataga     11220 ccgagatagg gttgagtgtt gttccagttt ggaacaagag tccactatta agaacgtgg    11280 actccaacgt caaagggcga aaaccgtct atcagggcga tggcccacta cgtgaaccat    11340
caccctaatc aagttttttg gggtcgaggt gccgtaaagc actaaatcgg aaccctaaag    11400 ggagccccg atttagagct tgacggggaa agccggcgaa cgtggcgaga aggaaggga    11460 agaaagcgaa aggagcgggc gctagggcgc tggcaagtgt agcggtcacg ctgcgcgtaa    11520
ccaccacacc cgccgcgctt aatgcgccgc tacagggcgc gatggatcc               11569
```

<210> SEQ ID NO 3
<211> LENGTH: 5030
<212> TYPE: DNA
<213> ORGANISM: Artificial Sequence
<220> FEATURE:
<223> OTHER INFORMATION: Coding Strand of Plasmid pAV-CMV-EGFP

<400> SEQUENCE: 3

```
cctgcaggca gctgcgcgct cgctcgctca ctgaggccgc ccgggcgtcg ggcgaccttt      60
ggtcgcccgg cctccagtg agcgagcgcg cagagaggga gtggccaact ccatcactag     120
gggttcctgc ggccgcacgc gtctagttat taatagtaat cgaattcgtg ttactcataa     180
ctagtaaggt cgggcaggaa gagggcctat tcccatgat tccttcatat ttgcatatac     240
gatacaaggc tgttagagag ataattagaa ttaatttgac tgtaaacaca aagatattag     300
tacaaaatac gtgacgtaga aagtaataat tccttgggta gtttgcagtt ttaaaattat     360
gttttaaaat ggactatcat atgcttaccg taacttgaaa gtatttcgat tcttgggtt     420 tatatatctt gtggaaagga cgcgggatcc actggaccag cagcagcgt cagaagactt     480 ttttggaaaa gcttgactag taatactgta atagtaatca attacggggt cattagttca     540
tagcccatat atggagttcc gcgttacata acttacggta aatggcccgc ctggctgacc     600
gcccaacgac ccccgcccat tgacgtcaat aatgacgtat gttcccatag taacgccaat     660
agggactttc cattgacgtc aatgggtgga gtatttacgg taaactgccc acttggcagt     720
```

```
acatcaagtg tatcatatgc caagtacgcc ccctattgac gtcaatgacg gtaaatggcc    780
cgcctggcat tatgcccagt acatgacctt atgggacttt cctacttggc agtacatcta    840
cgtattagtc atcgctatta ccatggtgat gcggttttgg cagtacatca atgggcgtgg    900
atagcggttt gactcacggg gatttccaag tctccacccc attgacgtca atgggagttt    960
gttttgcacc aaaatcaacg ggactttcca aaatgtcgta caactccgc cccattgacg   1020 caaatgggcg gtaggcgtgt acggtgggag gtctatataa gcagagctgg tttagtgaac   1080
cgtcagatcc gctagagatc cggtaccgag gagatctgcc gccgcgatcg ccggcgcgcc   1140
agatctcacg cttaactagc tagcggaccg acgcgtacgc ggccgctcga gatggtgagc   1200
aagggcgagg agctgttcac cggggtggtg cccatcctgg tcgagctgga cggcgacgta   1260 aacgccaca agttcagcgt gtccggcgag ggcgagggcg atgccaccta cggcaagctg   1320
accctgaagt tcatctgcac caccggcaag ctgcccgtgc cctggcccac cctcgtgacc   1380
accctgacct acggcgtgca gtgcttcagc cgctaccccg accacatgaa gcagcacgac   1440
ttcttcaagt ccgccatgcc cgaaggctac gtccaggagc gcaccatctt cttcaaggac   1500
gacggcaact acaagacccg cgccgaggtg aagttcgagg gcgacaccct ggtgaaccgc   1560
atcgagctga agggcatcga cttcaaggag gacggcaaca tcctggggca caagctggag   1620
tacaactaca acagccacaa cgtctatatc atggccgaca agcagaagaa cggcatcaag   1680
gtgaacttca agatccgcca caacatcgag gacggcagcg tgcagctcgc cgaccactac   1740
cagcagaaca cccccatcgg cgacggcccc gtgctgctgc ccgacaacca ctacctgagc   1800
acccagtccg ccctgagcaa agaccccaac gagaagcgcg atcacatggt cctgctggag   1860
ttcgtgaccg ccgccgggat cactctcggc atggacgagc tgtacaagta agtcgaggat   1920
tataaggatg acgacgataa attcgtcgag caccaccacc accaccacta ataaggttta   1980
tccgatccac cggatctaga taagatatcc gatccaccgg atctagataa ctgatcataa   2040
tcagccatac cacatttgta gaggttttac ttgctttaaa aaacctccca cacctccccc   2100
tgaacctgaa acataaaatg aatgcaattg ttgttgttaa cttgtttatt gcagcttata   2160
atggttacaa ataaagcaat agcatcacaa atttcacaaa taaagcattt ttttcactgc   2220
attctagttg tggtttgtcc aaactcatca atgtatctta acgcggtaac cacgtgcgga   2280
ccgagcggcc gcaggaaccc ctagtgatgg agttggccac tccctctctg cgcgctcgct   2340
cgctcactga ggccgggcga ccaaaggtcg cccgacgccc gggctttgcc cggcggcct   2400 cagtgagcga gcgagcgcgc agctgcctgc aggggcgcct gatgcggtat tttctcctta   2460
cgcatctgtg cggtatttca caccgcatac gtcaaagcaa ccatagtacg cgccctgtag   2520
cggcgcatta agcgcggcgg gtgtggtggt tacgcgcagc gtgaccgcta cacctgccag   2580
cgccttagcg cccgctcctt tcgctttctt cccttccttt ctcgccacgt tcgccggctt   2640
tccccgtcaa gctctaaatc gggggctccc tttagggttc cgatttagtg ctttacggca   2700
cctcgacccc aaaaaacttg atttgggtga tggttcacgt agtgggccat cgccctgata   2760
gacggttttt cgccctttga cgttggagtc cacgttcttt aatagtggac tcttgttcca   2820
aactggaaca cactcaacc ctatctcggg ctattctttt gatttataag ggattttgcc   2880
gatttcggcc tattggttaa aaaatgagct gatttaacaa aaatttaacg cgaattttaa   2940
caaaatatta acgtttacaa ttttatggtg cactctcagt acaatctgct ctgatgccgc   3000
atagttaagc cagccccgac acccgccaac acccgctgac gcgccctgac gggcttgtct   3060
gctcccggca tccgcttaca gacaagctgt gaccgtctcc gggagctgca tgtgtcagag   3120
```

```
gttttcaccg tcatcaccga aacgcgcgag acgaaagggc ctcgtgatac gcctattttt    3180
ataggttaat gtcatgataa taatggtttc ttagacgtca ggtggcactt ttcggggaaa    3240
tgtgcgcgga acccctattt gtttattttt ctaaatacat tcaaatatgt atccgctcat    3300
gagacaataa ccctgataaa tgcttcaata atattgaaaa aggaagagta tgagtattca    3360
acatttccgt gtcgccctta ttccctttt tgcggcattt tgccttcctg ttttgctca     3420
cccagaaacg ctggtgaaag taaaagatgc tgaagatcag ttgggtgcac gagtgggtta    3480
catcgaactg gatctcaaca gcggtaagat ccttgagagt tttcgccccg aagaacgttt    3540
tccaatgatg agcactttta aagttctgct atgtggcgcg gtattatccc gtattgacgc    3600
cgggcaagag caactcggtc gccgcataca ctattctcag aatgacttgg ttgagtactc    3660
accagtcaca gaaaagcatc ttacggatgg catgacagta agagaattat gcagtgctgc    3720
cataaccatg agtgataaca ctgcggccaa cttacttctg acaacgatcg gaggaccgaa    3780
ggagctaacc gcttttttgc acaacatggg ggatcatgta actcgccttg atcgttggga    3840
accggagctg aatgaagcca taccaaacga cgagcgtgac accacgatgc ctgtagcaat    3900
ggcaacaacg ttgcgcaaac tattaactgg cgaactactt actctagctt cccggcaaca    3960
attaatagac tggatggagg cggataaagt tgcaggacca cttctgcgct cggcccttcc    4020
ggctggctgg tttattgctg ataaatctgg agccggtgag cgtgggtctc gcggtatcat    4080
tgcagcactg gggccagatg gtaagccctc ccgtatcgta gttatctaca cgacggggag    4140
tcaggcaact atggatgaac gaaatagaca gatcgctgag ataggtgcct cactgattaa    4200
gcattggtaa ctgtcagacc aagtttactc atatatactt tagattgatt taaaacttca    4260
tttttaattt aaaaggatct aggtgaagat cctttttgat aatctcatga ccaaaatccc    4320
ttaacgtgag ttttcgttcc actgagcgtc agaccccgta gaaaagatca aggatcttc    4380
ttgagatcct ttttttctgc gcgtaatctg ctgcttgcaa acaaaaaaac caccgctacc    4440
agcggtggtt tgtttgccgg atcaagagct accaactctt tttccgaagg taactggctt    4500
cagcagagcg cagataccaa atactgtcct tctagtgtag ccgtagttag gccaccactt    4560
caagaactct gtagcaccgc ctacatacct cgctctgcta atcctgttac cagtggctgc    4620
tgccagtggc gataagtcgt gtcttaccgg gttggactca agacgatagt taccggataa    4680
ggcgcagcgg tcgggctgaa cggggggttc gtgcacacag cccagcttgg agcgaacgac    4740
ctacaccgaa ctgagatacc tacagcgtga gctatgagaa agcgccacgc ttcccgaagg    4800
gagaaaggcg gacaggtatc cggtaagcgg cagggtcgga acaggagagc gcacgaggga    4860
gcttccaggg ggaaacgcct ggtatcttta tagtcctgtc gggtttcgcc acctctgact    4920
tgagcgtcga ttttgtgat gctcgtcagg gggcggagc ctatggaaaa acgccagcaa     4980
cgcggccttt ttacggttcc tggccttttg ctggcctttt gctcacatgt               5030
```

<210> SEQ ID NO 4
<211> LENGTH: 4742
<212> TYPE: DNA
<213> ORGANISM: Artificial Sequence
<220> FEATURE:
<223> OTHER INFORMATION: Coding Strand of Plasmid pAV-TBG-EGFP

<400> SEQUENCE: 4

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
```

```
aggggttcct gcggccggtc gcgtctagta ctagtaggtt aattttttaaa aagcagtcaa    180 aagtccaagt ggcccttggc agcatttact ctctctgttt gctctggtta ataatctcag    240
gagcacaaac attccagatc caggttaatt tttaaaaagc agtcaaaagt ccaagtggcc    300
cttggcagca tttactctct ctgtttgctc tggttaataa tctcaggagc acaaacattc    360
cagatccggc gcgccagggc tggaagctac ctttgacatc atttcctctg cgaatgcatg    420
tataatttct acagaaccta ttagaaagga tcacccagcc tctgcttttg tacaactttc    480
ccttaaaaaa ctgccaattc cactgctgtt tggcccaata gtgagaactt tttcctgctg    540
cctcttggtg cttttgccta tggcccctat tctgcctgct gaagacactc ttgccagcat    600
ggacttaaac ccctccagct ctgacaatcc tcttttctctt ttgttttaca tgaagggtct    660
ggcagccaaa gcaatcactc aaagttcaaa ccttatcatt ttttgctttg ttcctcttgg    720
ccttggtttt gtacatcagc tttgaaaata ccatcccagg gttaatgctg gggttaattt    780
ataactaaga gtgctctagt tttgcaatac aggacatgct ataaaaatgg aaagatgttg    840 cttttctgaga gacaggtacc gaggagatct gccgccgcga tcgccaccat ggtgagcaag    900
ggcgaggagc tgttcaccgg ggtggtgccc atcctggtcg agctggacgg cgacgtaaac    960
ggccacaagt tcagcgtgtc cggcgagggc gagggcgatg ccacttacgg caagctgacc   1020
ctgaagttca tctgcaccac cggcaagctg cccgtgccct ggcccaccct cgtgaccacc   1080
ctgacctacg gcgtgcagtg cttcagccgc taccccgacc acatgaagca gcacgacttc   1140
ttcaagtccg ccatgcccga aggctacgtc caggagcgca ccatcttctt caaggacgac   1200
ggcaactaca agacccgcgc cgaggtgaag ttcgagggcg acaccctggt gaaccgcatc   1260
gagctgaagg gcatcgactt caaggaggac ggcaacatcc tggggcacaa gctggagtac   1320
aactacaaca gccacaacgt ctatatcatg gccgacaagc agaagaacgg catcaaggtg   1380
aacttcaaga tccgccacaa catcgaggac ggcagcgtgc agctcgccga ccactaccag   1440
cagaacaccc ccatcggcga cggccccgtg ctgctgcccg acaaccacta cctgagcacc   1500
cagtccgccc tgagcaaaga ccccaacgag aagcgcgatc acatggtcct gctggagttc   1560
gtgaccgccg ccgggatcac tctcggcatg gacgagctgt acaagtagac gcgtacgcgg   1620
ccgctcgagg attataagga tgacgacgat aaattcgtcg agcaccacca ccaccaccac   1680
taataaggtt tatccgatcc accggatcta gataagatat ccgatccacc ggatctagat   1740
aactgatcat aatcagccat accacatttg tagaggtttt acttgcttta aaaaacctcc   1800
cacacctccc cctgaacctg aaacataaaa tgaatgcaat tgttgttgtt aacttgttta   1860
ttgcagctta taatggttac aaataaagca atagcatcac aaatttcaca ataaagcat   1920 ttttttcact gcattctagt tgtggttttgt ccaaactcat caatgtatct taacgcggta   1980
accacgtgcg gacccaacgg ccgcaggaac ccctagtgat ggagttggcc actccctctc   2040
tgcgcgctcg ctcgctcact gaggccgggc gaccaaaggt cgcccgacgc ccgggctttg   2100
cccgggcggc ctcagtgagc gagcgagcgc gcagctgcct gcaggggcgc ctgatgcggt   2160
attttctcct tacgcatctg tgcggtattt cacaccgcat acgtcaaagc aaccatagta   2220
cgcgccctgt agcggcacat taagcgcggc gggtgtggtg gttacgcgca gcgtgaccgc   2280
tacacctgcc agcgccttag cgcccgctcc tttcgctttc ttcccttcct ttctcgccac   2340
gttcgccggc tttccccgtc aagctctaaa tcggggggctc cctttagggt tccgatttag   2400
tgctttacgg cacctcgacc ccaaaaaact tgatttgggt gatggttcac gtagtgggcc   2460
atcgccctga tagacggttt ttcgcccttt gacgttggag tccacgttct ttaatagtgg   2520
```

```
actcttgttc caaactggaa caacactcaa ctctatctcg ggctattctt ttgatttata  2580
agggattttg ccgatttcgg tctattggtt aaaaaatgag ctgatttaac aaaaatttaa  2640
cgcgaatttt aacaaaatat taacgtttac aattttatgg tgcactctca gtacaatctg  2700
ctctgatgcc gcatagttaa gccagccccg acacccgcca acacccgctg acgcgccctg  2760
acgggcttgt ctgctcccgg catccgctta cagacaagct gtgaccgtct ccgggagctg  2820
catgtgtcag aggttttcac cgtcatcacc gaaacgcgcg agacgaaagg cctcgtgat   2880
acgcctattt ttataggtta atgtcatgat aataatggtt tcttagacgt caggtggcac  2940
ttttcgggga atgtgcgcg gaaccctat ttgtttattt ttctaaatac attcaaatat    3000
gtatccgctc atgagacaat aaccctgata aatgcttcaa taatattgaa aaggaagag   3060
tatgagtatt caacatttcc gtgtcgccct tattccctt tttgcggcat tttgccttcc   3120
tgttttgct cacccagaaa cgctggtgaa agtaaaagat gctgaagatc agttgggtgc   3180
acgagtgggt tacatcgaac tggatctcaa cagcggtaag atccttgaga gttttcgccc  3240
cgaagaacgt tttccaatga tgagcacttt taaagttctg ctatgtggcg cggtattatc  3300
ccgtattgac gccgggcaag agcaactcgg tcgccgcata cactattctc agaatgactt  3360
ggttgagtac tcaccagtca cagaaaagca tcttacggat ggcatgacag taagagaatt  3420
atgcagtgct gccataacca tgagtgataa cactgcggcc aacttacttc tgacaacgat  3480
cggaggaccg aaggagctaa ccgcttttt gcacaacatg ggggatcatg taactcgcct   3540
tgatcgttgg gaaccggagc tgaatgaagc cataccaaac gacgagcgtg acaccacgat  3600
gcctgtagca atggcaacaa cgttgcgcaa actattaact ggcgaactac ttactctagc  3660
ttcccggcaa caattaatag actggatgga ggcggataaa gttgcaggac cacttctgcg  3720
ctcggccctt ccggctggct ggtttattgc tgataaatct ggagccggtg agcgtgggtc  3780
tcgcggtatc attgcagcac tggggccaga tggtaagccc tcccgtatcg tagttatcta  3840
cacgacgggg agtcaggcaa ctatggatga acgaaataga cagatcgctg agataggtgc  3900
ctcactgatt aagcattggt aactgtcaga ccaagtttac tcatatatac tttagattga  3960
tttaaaactt catttttaat ttaaaaggat ctaggtgaag atcctttttg ataatctcat  4020
gaccaaaatc ccttaacgtg agttttcgtt ccactgagcg tcagaccccg tagaaaagat  4080
caaaggatct tcttgagatc cttttttct gcgcgtaatc tgctgcttgc aaacaaaaaa   4140
accaccgcta ccagcggtgg tttgtttgcc ggatcaagag ctaccaactc tttttccgaa  4200
ggtaactggc ttcagcagag cgcagatacc aaatactgtt cttctagtgt agccgtagtt  4260
aggccaccac ttcaagaact ctgtagcacc gcctacatac ctcgctctgc taatcctgtt  4320
accagtggct gctgccagtg gcgataagtc gtgtcttacc gggttggact caagacgata  4380
gttaccggat aaggcgcagc ggtcgggctg aacggggggt tcgtgcacac agcccagctt  4440
ggagcgaacg acctacaccg aactgagata cctacagcgt gagctatgag aaagcgccac  4500
gcttcccgaa gggagaaagg cggacaggta tccggtaagc ggcagggtcg gaacaggaga  4560
gcgcacgagg gagcttccag ggggaaacgc ctggtatctt tatagtcctg tcgggtttcg  4620
ccacctctga cttgagcgtc gatttttgtg atgctcgtca gggggggcgga gcctatggaa  4680
aaacgccagc aacgcggcct ttttacggtt cctggccttt tgctggcctt tgctcacat   4740
gt                                                                 4742
```

USE OF ION CONCENTRATIONS TO INCREASE THE PACKAGING EFFICIENCY OF RECOMBINANT ADENO-ASSOCIATED VIRUS

FIELD OF THE INVENTION

The present invention is directed to methods for increasing the efficiencies with which recombinant adeno-associated virus (rAAV) are packaged, so as to increase their production titers. More specifically, the invention relates to a method for increasing the production titer of rAAV by transfected cells by increasing the ionic strength of the cell culture media through the administration of additional ions.

REFERENCE TO SEQUENCE LISTING

This application includes one or more Sequence Listings pursuant to 37 C.F.R. 1.821 et seq., which are disclosed in computer-readable media (file name: 2650-0002US_ST25.txt, created on Jul. 15, 2019, and having a size of 38,334 bytes), which file is herein incorporated by reference in its entirety.

BACKGROUND OF THE INVENTION

I. Adeno-Associated Virus (AAV)

Adeno-Associated Virus (AAV) is a small, naturally-occurring, non-pathogenic virus belonging to the *Dependovirus* genus of the Parvoviridae (Balakrishnan, B. et al. (2014) "*Basic Biology of Adeno Associated Virus (AAV) Vectors Used in Gene Therapy*," Curr. Gene Ther. 14(2):86-100; Zinn, E. et al. (2014) "*Adeno-Associated Virus: Fit To Serve*," Curr. Opin. Virol. 0:90-97). Despite not causing disease, AAV is known to be able to infect humans and other primates and is prevalent in human populations (Johnson, F. B. et al. (1972) "*Immunological Reactivity of Antisera Prepared Against the Sodium Dodecyl Sulfate-Treated Structural Polypeptides of Adenovirus-Associated Virus*," J. Virol. 9(6):1017-1026). AAV infect a broad range of different cell types (e.g., cells of the central nervous system, heart, kidney, liver, lung, pancreas, retinal pigment epithelium or photoreceptor cells, or skeletal muscle cells). Twelve serotypes of the virus (e.g., AAV2, AAV5, AAV6, etc.), exhibiting different tissue infection capabilities ("tropisms"), have been identified (Colella, P. et al. (2018) "*Emerging Issues in AAV-Mediated In Vivo Gene Therapy*," Molec. Ther. Meth. Clin. Develop. 8:87-104; Hocquemiller, M. et al. (2016) "*Adeno-Associated Virus-Based Gene Therapy for CNS Diseases*," Hum. Gene Ther. 27(7):478-496; Lisowski, L. et al. (2015) "*Adeno Associated Virus Serotypes For Gene Therapeutics,*" 24:59-67).

AAV is a single-stranded DNA virus that is composed of approximately 4,700 nucleotides. The viral genome may be described as having a 5' half and a 3' half which together comprise the genes that encode the virus' proteins (FIG. 1). The 5' half of the AAV genome comprises the AAV rep gene, which, through the use of multiple reading frames, staggered initiating promoters (p5, p19 and p40) and alternate splicing, encodes four non-structural Rep proteins (Rep40, Rep52, Rep68 and Rep78) that are required for viral transcription control and replication and for the packaging of viral genomes into the viral capsule (Lackner, D. F. et al. (2002) "*Studies of the Mechanism of Transactivation of the Adeno-Associated Virus p19 Promoter by Rep Protein*," J. Virol. 76(16):8225-8235). The 3' half the AAV genome comprises the AAV capsid gene (cap), which encodes three capsid proteins (VP): VP1, VP2 and VP3. The three capsid proteins are translated from a single mRNA transcript that is controlled by a single promoter (p40 in case of AAV2). The 3' half of the AAV genome also comprises the AAP gene, which encodes the AAV assembly-activating protein (AAP). Sixty VP monomers (comprising approximately 5 copies of VP1, 5 copies of VP2, and 50 copies of VP3) self-assemble around the AAV genome to form the icosahedral protein shell (capsid) of the mature viral particle (Büning, H. et al. (2019) "*Capsid Modifications for Targeting and Improving the Efficacy of AAV Vectors*," Mol. Ther. Meth. Clin. Devel. 12:P248-P265; Van Vliet K. M. et al. (2008) *The Role of the Adeno-Associated Virus Capsid in Gene Transfer*. In: DRUG DELIVERY SYSTEMS, Jain, K. K. (eds.), Meth. Molec. Biol. 437:51-91). The AAV AAP protein is believed to be required for stabilizing and transporting newly produced VP proteins from the cytoplasm into the cell nucleus. The 3' half of the AAV genome also comprises the AAV X gene, which is believed to encode a protein that supports genome replication (Colella, P. et al. (2018) "*Emerging Issues in AAV-Mediated In Vivo Gene Therapy*," Molec. Ther. Meth. Clin. Develop. 8:87-104; Büning, H. et al. (2019) "*Capsid Modifications for Targeting and Improving the Efficacy of AAV Vectors*," Mol. Ther. Meth. Clin. Devel. 12:P248-P265; Cao, M. et al. (2014) "*The X Gene Of Adeno-Associated Virus 2 (AAV2) Is Involved In Viral DNA Replication*," PLoS ONE 9, e104596:1-10).

The above-described AAV gene-coding sequences are flanked by two AAV-specific palindromic inverted terminal repeated sequences (ITR) of 145 nucleotides (Balakrishnan, B. et al. (2014) "*Basic Biology of Adeno-Associated Virus (AAV) Vectors Used in Gene Therapy*," Curr. Gene Ther. 14(2):86-100; Colella, P. et al. (2018) "*Emerging Issues in AAV-Mediated In Vivo Gene Therapy*," Molec. Ther. Meth. Clin. Develop. 8:87-104).

AAV is an inherently defective virus, lacking the capacity to perform at least two critical functions: the ability to initiate the synthesis of viral-specific products and the ability to assemble such products to form the icosahedral protein shell (capsid) of the mature infectious viral particle. It thus requires a co-infecting "helper" virus, such as adenovirus (Ad), herpes simplex virus (HSV), cytomegalovirus (CMV), vaccinia virus or human papillomavirus to provide the viral-associated (VA) RNA that is not encoded by the genes of the AAV genome. Such VA RNA is not translated, but plays a role in regulating the translation of other viral genes. Similarly, the AAV genome does not include genes that encode the viral proteins E1a, E1b, E2a, and E4 of Ad; thus, these proteins must also be provided by a co-infecting "helper" virus. The E1a protein greatly stimulate viral gene transcription during the productive infection. The E1b protein block apoptosis in adenovirus-infected cells, and thus allow productive infection to proceed. The E2a protein plays a role in the elongation phase of viral strand displacement replication by unwinding the template and enhancing the initiation of transcription. The E4 protein has been shown to affect transgene persistence, vector toxicity and immunogenicity (see, Grieger, J. C. et al. (2012) "*Adeno-Associated Virus Vectorology, Manufacturing, and Clinical Applications*," Meth. Enzymol. 507:229-254; Dyson, N. et al. (1992) "*Adenovirus E1A Targets Key Regulators Of Cell Proliferation*," Canc. Surv. 12:161-195; Jones N. C. (1990) "*Transformation By The Human Adenoviruses*," Semin. Cancer Biol. 1(6):425-435; Ben-Israel, H. et al. (2002) "*Adenovirus and Cell Cycle Control*," Front. Biosci. 7:d1369-d1395; Hoeben, R. C. et al. (2013) "*Adenovirus DNA Replication*," Cold Spring Harb. Perspect. Biol.

5:a013003 (pages 1-11); Berk, A. J. (2013) "*Adenoviridae: The Viruses And Their Replication*, In: FIELDS VIROLOGY, 6*th* Edition (Knipe, D. M. et al., Eds.), Vol. 2., Lippincott Williams & Wilkins, Philadelphia, pages 1704-1731; Weitzman, M. D. (2005) "*Functions Of The Adenovirus E4 Proteins And Their Impact On Viral Vectors*," Front. Biosci. 10:1106-1117).

AAV viruses infect both dividing and non-dividing cells, and persist as circular episomal molecules or can be integrated into the DNA of a host cell at specific chromosomic loci (Adeno-Associated Virus Integration Sites or AAVS) (Duan, D. (2016) "*Systemic Delivery Of Adeno Associated Viral Vectors*," Curr. Opin. Virol. 21:16-25; Grieger, J. C. et al. (2012) "*Adeno-Associated Virus Vectorology, Manufacturing, and Clinical Applications*," Meth. Enzymol. 507: 229-254). AAV remains latent in such infected cells unless a helper virus is present to provide the functions needed for AAV replication and maturation.

II. rAAV and their Use in Gene Therapy

In light of AAV's properties, recombinantly-modified versions of AAV (rAAV) have found substantial utility as vectors for gene therapy (see, Naso, M. F. et al. (2017) "*Adeno-Associated Virus (AAV) as a Vector for Gene Therapy*," BioDrugs 31:317-334; Berns, K. I. et al. (2017) "*AAV: An Overview of Unanswered Questions*," Human Gene Ther. 28(4):308-313; Berry, G. E. et al. (2016) "*Cellular Transduction Mechanisms Of Adeno-Associated Viral Vectors*," Curr. Opin. Virol. 21:54-60; Blessing, D. et al. (2016) "*Adeno-Associated Virus And Lentivirus Vectors: A Refined Toolkit For The Central Nervous System,"* 21:61-66; Santiago-Ortiz, J. L. (2016) "*Adeno-Associated Virus (AAV) Vectors in Cancer Gene Therapy*," J. Control Release 240: 287-301; Salganik, M. et al. (2015) "*Adeno-Associated Virus As A Mammalian DNA Vector*," Microbiol. Spectr. 3(4):1-32; Hocquemiller, M. et al. (2016) "*Adeno-Associated Virus-Based Gene Therapy for CNS Diseases*," Hum. Gene Ther. 27(7):478-496; Lykken, E. A. et al. (2018) "*Recent Progress And Considerations For AAV Gene Therapies Targeting The Central Nervous System*," J. Neurodevelop. Dis. 10:16:1-10; Büning, H. et al. (2019) "*Capsid Modifications for Targeting and Improving the Efficacy of AAV Vectors*," Mol. Ther. Meth. Clin. Devel. 12:P248-P265; During, M. J. et al. (1998) "*In Vivo Expression Of Therapeutic Human Genes For Dopamine Production In The Caudates Of MPTP-Treated Monkeys Using An AAV Vector*," Gene Ther. 5:820-827; Grieger, J. C. et al. (2012) "*Adeno Associated Virus Vectorology, Manufacturing, and Clinical Applications*," Meth. Enzymol. 507:229-254; Kotterman, M. A. et al. (2014) "*Engineering Adeno-Associated Viruses For Clinical Gene Therapy*," Nat. Rev. Genet. 15(7):445-451; Kwon, I. et al. (2007) "*Designer Gene Delivery Vectors: Molecular Engineering and Evolution of Adeno-Associated Viral Vectors for Enhanced Gene Transfer*," Pharm. Res. 25(3):489-499).

rAAV are typically produced using circular plasmids ("rAAV plasmid vector"). The AAV rep and cap genes are typically deleted from such constructs and replaced with a promoter, a β-globin intron, a cloning site into which a therapeutic gene of choice (transgene) has been inserted, and a poly-adenylation ("polyA") site. The inverted terminal repeated sequences (ITR) of the rAAV are, however, retained, so that the transgene expression cassette of the rAAV plasmid vector is flanked by AAV ITR sequences (Colella, P. et al. (2018) "*Emerging Issues in AAV-Mediated In Vivo Gene Therapy*," Molec. Ther. Meth. Clin. Develop. 8:87-104; Büning, H. et al. (2019) "*Capsid Modifications for Targeting and Improving the Efficacy of AAV Vectors*," Mol. Ther. Meth. Clin. Devel. 12:P248-P265). Thus, in the 5' to 3' direction, the rAAV comprises a 5' ITR, the transgene expression cassette of the rAAV, and a 3' ITR.

rAAV have been used to deliver a transgene to patients suffering from any of a multitude of genetic diseases (e.g., hereditary lipoprotein lipase deficiency (LPLD), Leber's congenital amaurosis (LCA), aromatic L-amino acid decarboxylase deficiency (AADC), choroideremia and hemophilia), and have utility in new clinical modalities, such as in interfering RNA (RNAi) therapy and gene-modifying strategies such as Crispr/Cas9 (U.S. Pat. Nos. 8,697,359, 10,000,772, 10,113,167, 10,227,611; Lino, C. A. et al. (2018) "*Delivering CRISPR: A Review Of The Challenges And Approaches*," Drug Deliv. 25(1):1234-1237; Ferreira, V. et al. (2014) "*Immune Responses To AAV-Vectors, The Glybera Example From Bench To Bedside*" Front. Immunol. 5(82):1-15), Büning, H. et al. (2019) "*Capsid Modifications for Targeting and Improving the Efficacy of AAV Vectors*," Mol. Ther. Meth. Clin. Devel. 12:P248-P265; Rastall, D. P. W. (2017) "*Current and Future Treatments for Lysosomal Storage Disorders*," Curr. Treat Options Neurol. 19(12):45; Kay, M. et al. (2017) "*Future Of rAAV Gene Therapy: Platform For RNAi, Gene Editing And Beyond*," Human Gene Ther. 28:361-372); Berns, K. I. et al. (2017) "*AAV: An Overview of Unanswered Questions*," Human Gene Ther. 28(4):308-313). More than 150 clinical trials involving rAAV have been instituted (Büning, H. et al. (2019) "*Capsid Modifications for Targeting and Improving the Efficacy of AAV Vectors*," Mol. Ther. Meth. Clin. Devel. 12:P248-P265; Clement, N. et al. (2016) "*Manufacturing Of Recombinant Adeno Associated Viral Vectors For Clinical Trials*," Meth. Clin. Develop. 3:16002:1-7). The most commonly used AAV serotype for such recombinantly-modified AAV is AAV2, which is capable of infecting cells of the central nervous system, kidney, retinal pigment epithelium and photoreceptor cells. Another AAV serotype is AAV9, which infects muscle cells, also has been widely used (Duan, D. (2016) "*Systemic Delivery Of Adeno-Associated Viral Vectors*," Curr. Opin. Virol. 21:16-25). AAV serotypes are described in U.S. Pat. Nos. 10,301,650; 10,266,846; 10,265, 417; 10,214,785; 10,214,566; 10,202,657; 10,046,016; 9,884,071; 9,856,539; 9,737,618; 9,677,089; 9,458,517; 9,457,103; 9,441,244; 9,193,956; 8,846,389; 8,507,267; 7,906,111; 7,479,554; 7,186,552; 7,105,345; 6,984,517; 6,962,815; and 6,733,757.

III. Methods of rAAV Production rAAV containing a desired transgene expression cassette are typically produced by human cells (such as HEK293) grown in either adhesion or suspension. Since, as described above, rAAV are defective viruses, additional functions must be provided in order to replicate and package rAAV.

Typically, rAAV are produced by transiently transfecting cells with an rAAV plasmid vector and a second plasmid vector that comprises an AAV helper function-providing polynucleotide that provides the Rep52 and Rep78 genes that are required for vector transcription control and replication, and for the packaging of viral genomes into the viral capsule (Rep40 and Rep68 are not required for rAAV production) and the cap genes that were excised from the AAV in order to produce the rAAV. The second plasmid vector may additionally comprise a non-AAV helper function-providing polynucleotide that encodes the viral transcription and translation factors (E1a, E1b, E2a, VA and E4) required for AAV proliferation, so as to comprise, in concert with the rAAV, a double plasmid transfection system (Grimm, D. et al. (1998) "*Novel Tools For Production And Purification Of Recombinant Adeno-Associated Virus Vec-* tors," Hum. Gene Ther. 9:2745-2760; Penaud-Budloo, M. et al. (2018) "*Pharmacology of Recombinant Adeno-associated Virus Production,*" Molec. Ther. Meth. Clin. Develop. 8:166-180).

However, it has become increasingly common to clone the AAV helper function-providing polynucleotide (which provides the required rep and cap genes) into an "AAV helper plasmid," and to clone the non-AAV helper function-providing polynucleotide (which provides the genes that encode the viral transcription and translation factors) on a different plasmid (i.e., an "Ad helper plasmid"), so that such plasmids, in concert with an rAAV plasmid vector, comprise a triple plasmid transfection system (FIG. 2). Use of the triple plasmid transfection system has the advantage of permitting one to easily switch one cap gene for another, thereby facilitating changes in the rAAV's serotype. The use of helper plasmids, rather than helper viruses, permits rAAV to be produced without additionally producing particles of the helper virus (Francois, A. et al. (2018) "*Accurate Titration of Infectious AAV Particles Requires Measurement of Biologically Active Vector Genomes and Suitable Controls,*" Molec. Ther. Meth. Clin. Develop. 10:223-236; Matsushita, T. et al. (1998) "*Adeno Associated Virus Vectors Can Be Efficiently Produced Without Helper Virus,*" Gene Ther. 5:938-945).

The transient transfection of plasmid DNAs comprising an rAAV plasmid vector, a plasmid vector providing AAV helper functions rep and cap genes, and a plasmid vector providing non-AAV helper functions into HEK293 cells by calcium phosphate coprecipitation has become the standard method to produce rAAV in the research laboratory (Grimm, D. et al. (1998) "*Novel Tools For Production And Purification Of Recombinant Adeno-Associated Virus Vectors,*" Hum. Gene Ther. 9:2745-2760). However, the use of such a calcium phosphate-mediated transfection process with suspension-cultured transfected mammalian cells requires media exchanges, and is thus not considered ideal for the large-scale rAAV production that is required in order to produce therapeutic doses of rAAV (Lock, M. et al. (2010) "*Rapid, Simple, and Versatile Manufacturing of Recombinant Adeno-Associated Viral Vectors at Scale,*" Hum. Gene Ther. 21:1259-1271). For this reason, polyethylenimine (PEI), has been used as a transfection reagent and has been found to provide yields of virus that are similar to those obtained using calcium phosphate-mediated transfection (Durocher, Y. et al. (2007) "*Scalable Serum-Free Production Of Recombinant Adeno-Associated Virus Type 2 By Transfection Of 293 Suspension Cells,*" J. Virol. Meth. 144:32-40).

rAAV may alternatively be produced in insect cells (e.g., sf9 cells) using baculoviral vectors (see. e.g., U.S. Pat. Nos. 9,879,282; 9,879,279; 8,945,918; 8,163,543; 7,271,002 and 6,723,551), or in HSV-infected baby hamster kidney (BHK) cells (e.g., BHK21) (Francois, A. et al. (2018) "*Accurate Titration of Infectious AAV Particles Requires Measurement of Biologically Active Vector Genomes and Suitable Controls,*" Molec. Ther. Meth. Clin. Develop. 10:223-236). Methods of rAAV production are reviewed in Grieger, J. C. et al. (2012) "*Adeno Associated Virus Vectorology, Manufacturing, and Clinical Applications,*" Meth. Enzymol. 507: 229-254, and in Penaud-Budloo, M. et al. (2018) "*Pharmacology of Recombinant Adeno-associated Virus Production,*" Molec. Ther. Meth. Clin. Develop. 8:166-180.

IV. Methods of rAAV Purification and Recovery

After production, rAAV are typically collected and purified by one or more overnight CsCl gradient centrifugations (Zolotukhin, S. et al. (1999) "*Recombinant Adeno-Associated Virus Purification Using Novel Methods Improves Infectious Titer And Yield,*" Gene Ther. 6:973-985), followed by desalting to form a purified rAAV production stock. Titers of $10^{12}$-$10^{13}$ infectious rAAV capsids/mL are obtainable.

Because rAAV infection does not cause a cytopathic effect, plaque assays cannot be used to determine the infectious titer of an rAAV preparation. Infectious titer is thus typically measured as the median tissue culture infective dose (TCID50). In this method, a HeLa-derived AAV2 rep- and cap-expressing cell line is grown in a 96-well plate and infected with replicate 10-fold serial dilutions of the rAAV preparation, in the presence of adenovirus of serotype 5. After infection, vector genome replication is determined by quantitative PCR (qPCR) (Zen, Z. et al. (2004) "*Infectious Titer Assay For Adeno-Associated Virus Vectors With Sensitivity Sufficient To Detect Single Infectious Events,*" Hum. Gene Ther. 15:709-715). Alternatively, the infectious titer of an rAAV preparation can be measured using the infectious center assay (ICA). This assay uses HeLa rep-cap cells and Ad, but, after incubation, involves transferring the cells to a membrane. A labeled probe that is complementary to a portion of the employed transgene is used to detect infectious centers (representing individual infected cells) via hybridization. Although more widely used, the TCID50 assay has been reported to lead to a higher background than the ICA and to overestimate vector infectivity relative to the ICA (Francois, A. et al. (2018) "*Accurate Titration of Infectious AAV Particles Requires Measurement of Biologically Active Vector Genomes and Suitable Controls,*" Molec. Ther. Meth. Clin. Develop. 10:223-236). Methods of producing and purifying rAAV are described inter alia in U.S. Pat. Nos. 10,294,452; 10,161,011; 10,017,746; 9,598,703; 7,625,570; 7,439,065; 7,419,817; 7,208,315; 6,995,006; 6,989,264; 6,846,665 and 6,841,357.

As discussed above, multiple rounds of overnight cesium chloride gradient centrifugation are typically employed in order to produce rAAV in the research laboratory. However, prolonged exposure to CsCl has been reported to compromise the potency of rAAV plasmid vectors (Zolotukhin, S. et al. (1999) "*Recombinant Adeno Associated Virus Purification Using Novel Methods Improves Infectious Titer And Yield,*" Gene Ther. 6:973-985). Additionally, such gradients have a limited loading capacity for cell lysate, and thus limit the amount of rAAV that may be purified. Although an isotonic alternative gradient medium, iodixanol, has been used to purify rAAV plasmid vectors, iodixanol shares the same loading capacity drawback as CsCl for rAAV production.

In order to overcome such gradient-specific constraints, researchers have developed ion-exchange chromatographic methods, affinity purification methods, and antibody-affinity based methods of rAAV purification (Auricchio, A. et al. (2001) "*Isolation Of Highly Infectious And Pure Adeno-Associated Virus Type 2 Vectors With A Single-Step Gravity-Flow Column,*" Hum. Gene Ther. 12:71-76; Brument, N. et al. (2002) "*A Versatile And Scalable Two-Step Ion-Exchange Chromatography Process For The Purification Of Recombinant Adeno-Associated Virus Serotypes-2 And-5,*" Mol. Ther. 6:678-686; Zolotukhin, S. et al. (2002) "*Production And Purification Of Serotype 1, 2, And 5 Recombinant Adeno-Associated Viral Vectors,*" Methods 28:158-167; Davidoff, A. M. et al. (2004) "*Purification Of Recombinant Adeno-Associated Virus Type 8 Vectors By Ion Exchange Chromatography Generates Clinical Grade Vector Stock,*" J. Virol. Methods 121:209-215; Smith, R. H. et al. (2009) "*A Simplified Baculovirus AAV Expression Vector System*

Coupled With One-Step Affinity Purification Yields High-Titer rAAV Stocks From Insect Cells," Mol. Ther. 17:1888-1896; Lock, M. et al. (2010) "Rapid, Simple, and Versatile Manufacturing of Recombinant Adeno Associated Viral Vectors at Scale," Hum. Gene Ther. 21:1259-1271). Unfortunately, however, such chromatography-based purification methods are generally unable to separate vector-related impurities, such as empty capsids from fully functional vector particles. Thus, despite its drawbacks, CsCl gradient centrifugation remains the best characterized method for removing empty particles from rAAV vector preparations.

It has been observed that rAAV of various serotypes is released to the supernatant in both calcium phosphate- and PEI-transfected cultures (Lock, M. et al. (2010) "Rapid, Simple, and Versatile Manufacturing of Recombinant Adeno-Associated Viral Vectors at Scale," Hum. Gene Ther. 21:1259-1271; U.S. Pat. Nos. 6,566,118 and 6,989,264, and US Patent Publication US 2005/0266567). U.S. Pat. Nos. 6,566,118 and 6,989,264, and US Patent Publication US 2005/0266567 disclose that high titers of recombinant AAV vectors are released into the supernatant of cell suspensions if the culture medium had been formulated to initially comprise an osmolarity of between about 100 mOsM to about 650 mOsM using NaCl (i.e., 50-325 mM NaCl) and other, but unspecified, salts, mannitol or glucose, or by manipulating the conductivity of the culture medium to be at least about 5 mS, using an ionic solute such as $Na^+$ or $K^+$. An initial osmolarity of 300 mOsM (150 mM) NaCl was found to be optimal. Adamson-Small, L. et al. (2017) similarly demonstrated that 60-90 mM sodium chloride in the production medium resulted in a significant increase in rAAV9 transducing units and capsid proteins under infection conditions in which increased sodium chloride was present 4-6 hr post-transduction (WO 2017/112948; Adamson-Small, L. et al. (2017) "Sodium Chloride Enhances Recombinant Adeno-Associated Virus Production in a Serum-Free Suspension Manufacturing Platform Using the Herpes Simplex Virus System," Hum. Gene Ther. Meth. 28(1):1-14).

Lock, M. et al. (2010) disclose a PEI transfection-based- and supernatant harvest-based-technique for facilitating the recovery of rAAV particles (Lock, M. et al. (2010) "Rapid, Simple, and Versatile Manufacturing of Recombinant Adeno-Associated Viral Vectors at Scale," Hum. Gene Ther. 21:1259-1271). The method is based on the observation that rAAV belonging to AAV serotypes other than AAV2 were released primarily into the culture medium of calcium phosphate-transfected cells and were not retained in the cell lysate. As such, Lock, M. et al. (2010) discloses that for such rAAV serotypes, the production culture medium represents a relatively pure source of rAAV plasmid vector that possesses a lower level of cellular contaminants and that these factors improve the loading capacity and resolution of purification gradients. In the disclosed method, rAAV, including rAAV belonging to AAV2 serotype, were transfected into HEK293 cells using calcium phosphate. Seventy-two hours (or 120 hours) post-transfection, serum-free media was added and the incubation was continued for an additional 28 hours. Benzonase®, a genetically engineered endonuclease that degrades all forms for DNA and RNA, was then added to the culture supernatant. After 2 hours, NaCl was added to 500 mM and the incubation was resumed for an additional 2 hr before harvesting the culture medium. The clarified medium was then concentrated 125-fold by tangential flow filtration (TFF), and the rAAV was purified using iodixanol step gradients. The method could be employed with AAV of serotypes AAV1, AAV6, AAV7, AAV8, and AAV9. Use of the high-salt incubation of Lock et al. (2010) is disclosed to lead to a further 20% release of rAAV6 and rAAV9 plasmid vectors to the culture medium (relative to the methods of U.S. Pat. Nos. 6,566,118 and 6,989,264 and US Patent Publication US 2005/0266567), but was seen to have elicited little change with respect to other serotypes. Although the average overall yields of rAAV8 and rAAV9 were high ($2.2 \times 10^{14}$ genome copies), yields of other rAAV serotypes were significantly lower (e.g., $6.7 \times 10^{13}$ genome copies for rAAV6). Although the estimated purity of the produced rAAV exceeded 90%, between 35% and 50% of the produced rAAV8 and rAAV9 were lost in the processing steps, and 80-85% of the produced rAAV6 were lost in processing, and rAAV2 were mostly retained within the cells and not released into the culture medium.

Provision of salt has also been used to permeabilize cells in order to more easily measure transgene-associated gene expression. Thus, for example, During, M. J. et al. (1998) used a "release buffer" containing 135 mm NaCl, 3 mm KCl, 1.2 mm $CaCl_2$, 1.0 mm $MgCl_2$, 10 mm glucose, 200 mm ascorbate and 2 mm sodium mono- and dibasic phosphate buffered to pH 7.4 to promote the release of dopamine from HEK 293 cells that had been transfected with an rAAV expressing human tyrosine hydroxylase (TH) and aromatic amino decarboxylase (AADC) (During, M. J. (1998) "In Vivo Expression Of Therapeutic Human Genes For Dopamine Production In The Caudates Of MPTP-Treated Monkeys Using An AAV Vector," Gene Ther. 5:820-827).

However, despite all such prior successes, a need remains to develop methods capable of addressing problems that presently limit the applicability of rAAV to gene therapy (Grieger, J. C. et al. (2012) "Adeno Associated Virus Vectorology, Manufacturing, and Clinical Applications," Meth. Enzymol. 507:229-254; Kotterman, M. A. et al. (2014) "Engineering Adeno-Associated Viruses For Clinical Gene Therapy," Nat. Rev. Genet. 15(7):445-451; Kwon, I. et al. (2007) "Designer Gene Delivery Vectors: Molecular Engineering and Evolution of Adeno-Associated Viral Vectors for Enhanced Gene Transfer," Pharm. Res. 25(3):489-499; Naso, M. F. et al. (2017) "Adeno-Associated Virus (AAV) as a Vector for Gene Therapy," BioDrugs 31:317-334). Such problems include:

(1) The Limited Tissue-Specific Tropism of rAAV: One such problem reflects the limited tissue-specific tropisms of AAV and rAAV. The use of multiple helper plasmids, encoding capsid proteins of differing serotypes (i.e., "mosaic" capsids) has been exploited as a way to increase the range of tissue types that can be infected by rAAV (Hauck, B. et al. (2003) "Generation And Characterization Of Chimeric Recombinant AAV Vectors," Mol. Ther. 7:419-425; Rabinowitz, J. E. et al. (2004) "Crossdressing The Virion: The Transcapsidation Of Adeno-Associated Virus Serotypes Functionally Defines Subgroups," J. Virol. 78:4421-4432; Lisowski, L. et al. (2015) "Adeno-Associated Virus Serotypes For Gene Therapeutics," 24:59-67).

(2) The Prevalence of anti-rAAV Immune Responses: A second such problem reflects the fact that 30-80% of humans have been naturally exposed to AAV infection (mainly AAV2) and 20-67% of humans harbor titers of neutralizing anti-AAV capsid antibodies in their blood and other bodily fluids (Liu, Q. et al. (2014) "Neutralizing Antibodies Against AAV2, AAV5 And AAV8 In Healthy And HIV-1-Infected Subjects In China: Implications For Gene Therapy Using AAV Vectors," Gene Ther. 21:732-738; Vandamme, C. et al. (2017) "Unraveling the Complex Story of Immune Responses to AAV Vectors Trial

*After Trial,*" Hum. Gene. Ther. 28(11):1061-1074). The presence of these antibodies attenuates the effectiveness of rAAV therapy by preventing transgene expression. Synthetic polymer conjugates (e.g., polyethylene glycol (PEG)) have been used as a means for shielding rAAV from neutralizing antibodies (Le, H. T. et al. (2005) "*Utility Of Pegylated Recombinant Adeno-Associated Viruses For Gene Transfer,*" J. Control. Release 108:161-177; Lee, G. K. et al. (2005) "*PEG Conjugation Moderately Protects Adeno Associated Viral Vectors Against Antibody Neutralization,*" Biotechnol. Bioeng. 92:24-34). The use of rAAV having alternative serotypes or mutated non-immunogenic capsids has also been pursued (Smith, J. K. et al. (2018) "*Creating An Arsenal Of Adeno-Associated Virus (AAV) Gene Delivery Stealth Vehicles,*" PLoS Pathog. 14(5):1-6).

(3) The Limitation of rAAV Packaging Capacity: The packaging efficiency of rAAV has been found to significantly decrease beyond 5 kb, with lager genomes being encapsidated with 5' truncations (Wu, Z. et al. (2010) "*Effect Of Genome Size On AAV Vector Packaging,*" Molec. Ther. 18:80-86; Ghosh, A. et al. (2007) "*Expanding Adeno-Associated Viral Vector Capacity: A Tale Of Two Vectors,*" Biotechnol. Genet. Eng. Rev. 24:165-177; McClements, M. E. et a. (2017) "*Adeno-associated Virus (AAV) Dual Vector Strategies for Gene Therapy Encoding Large Transgenes,*" Yale J. Biol. Med. 90:611-623).

(4) The Limitations of Large-Scale Manufacturing Technologies: The ability to manufacture rAAV in amounts sufficient for use in large-scale therapy has been a barrier to the successful application of the technology, with process yields ranging from below 5% to below 30% (Lock, M. et al. (2010) "*Rapid, Simple, and Versatile Manufacturing of Recombinant Adeno-Associated Viral Vectors at Scale,*" Hum. Gene Ther. 21:1259-1271).

These problems are, in some cases, inter-related. For example, the presence of empty particles in the final product exposes the recipient of the vector to a large source of AAV antigen that can lead to unwanted immune responses and toxicity. Thus, improved methods for increasing packaging efficiency and obtaining high production titers are of great importance.

The present invention is directed to improved methods for increasing the efficiency of rAAV packaging by altering the concentration of ions in a culturing medium during the production of rAAV.

SUMMARY OF THE INVENTION

The present invention is directed to methods for increasing the efficiency with which recombinant adeno-associated virus (rAAV) are packaged, so as to increase their production titers. More specifically, the invention relates to a method for increasing the production titer of rAAV by transfected cells by increasing the ionic strength of the cell culture media through the administration of additional ions.

In detail, the invention provides a method for increasing the production titer of recombinantly-modified adeno-associated virus (rAAV), wherein the method comprises the steps:
(A) culturing cells that have been transfected with the rAAV in an initial culture medium for an initial period under conditions sufficient to permit the production of rAAV, wherein the cells additionally contain an AAV helper function-providing polynucleotide and a non-AAV helper function-providing polynucleotide;
(B) changing the ionic strength of the culture medium after the initial period by adding one or more ions other than $Na^+$ to the culture medium; and
(C) continuing the culturing of the cells to thereby produce a production titer of with the rAAV that is greater than a titer obtained in the absence of step (B).

The invention additionally provides the embodiment of such method wherein each of the added ion(s) is provided in an amount sufficient to increase the concentration of such ion in the initial culture medium by from about 10 mM to about 80 mM.

The invention additionally provides the embodiment of such methods wherein the production titer is at least 50% greater than the titer obtained from a similarly conducted cell culturing in the absence of the step (B).

The invention additionally provides the embodiment of such methods wherein the rAAV comprises a transgene cassette that encodes a protein, or comprises a transcribed nucleic acid, that is therapeutic for a genetic or heritable disease or condition.

The invention additionally provides the embodiment of such methods wherein the rAAV belongs to the rAAV1, rAAV2, rAAV5, rAAV6, rAAV7, rAAV8, rAAV9 or rAAV10 serotype, or to a hybrid of such serotypes.

The invention additionally provides the embodiment of such methods wherein the rAAV belongs to the rAAV2, rAAV5, or rAAV9 serotype, or to a hybrid of the serotypes.

The invention additionally provides the embodiment of such methods wherein the added ions comprise one or more of $K^+$, $Ca^{++}$, or $Mg^{++}$.

The invention additionally provides the embodiment of such methods wherein the added ions comprise one or more of $CO_3^=$, $HCO_3^-$, $HPO_4^-$, $PO_4^=$, $SCN^-$, $SO_4^=$, $HSO_4^-$, and $Cl^-$.

The invention additionally provides the embodiment of such methods wherein the added ions comprise one or more of acetate, aspartate, biphthalate, bitartrate, butoxyethoxy acetate, caprylate, citrate, dehydroacetate, diacetate, dihydroxy glycinate, d-saccharate, gluconate, glutamate, glycinate, glycosulfate, hydroxymethane sulfonate, lactate, methionate, oxalate, phenate, phenosulfonate, propionate, propionate, saccharin, salicylate, sarcosinate, sorbate, thioglycolate, and toluene sulfonate.

The invention additionally provides the embodiment of such methods wherein the added ions comprise $K^+$ and $CO_3^=$.

The invention additionally provides the embodiment of such methods wherein the cells are human embryonic kidney cells, baby hamster kidney cells or sf9 insect cells.

The invention additionally provides the embodiment of such methods wherein the cells are HEK293 human embryonic kidney cells.

The invention additionally provides the embodiment of such methods wherein the cells are BHK21 baby hamster kidney cells.

The invention additionally provides the embodiment of such methods wherein the initial culture medium is Dulbecco's Modified Eagle's Medium or Dulbecco's Modified Eagle's Medium supplemented with serum.

The invention additionally provides a pharmaceutical composition that comprises:
(A) a preparation of recombinantly-modified adeno-associated virus (rAAV) produced by any of the above-described methods, wherein the rAAV comprises a transgene cassette that encodes a protein, or a transcribed nucleic acid, that is therapeutic for a genetic or heritable disease or condition, and wherein the pharmaceutical composition contains an effective amount of the rAAV preparation; and (B) a pharmaceutically acceptable carrier.

The invention additionally provides a preparation of recombinantly-modified adeno-associated virus (rAAV) produced by any of the above-described methods, wherein the rAAV comprises a transgene cassette that encodes a protein, or a transcribed nucleic acid, or the above-described pharmaceutical composition for use in the treatment of a genetic or heritable disease or condition.

BRIEF DESCRIPTION OF THE DRAWINGS

FIG. 7A shows the extent of expression of the enhanced green fluorescent protein (EGFP) in the transfected cells and the titering of the rAAV stocks using the infectious center assay. Stocks were produced by growing transfected HEK293 cells in Dulbecco's Modified Eagle's Medium in the presence of additionally added NaCl, KCl, $CaCl_2$ or $MgCl_2$. The additional concentration of such provided salt is 0, 20, 40, 60, 80 or 100 mM. FIG. 7A shows the infectious center assay. FIG. 7B is a graph of the fold-change in the titers of AAV vectors and salt concentration. FIG. 7C is a graph of the fold-change in Total Genomes (TG) of AAV as a function of cation and cation concentration. The concentration shown in the Figure is the concentration increase in the culturing medium provided by the addition of such salts.

FIG. 8A shows the extent of expression of the enhanced green fluorescent protein (EGFP) in the transfected cells and the titering of the rAAV stocks using the infectious center assay. Stocks were produced by growing transfected HEK293 cells in Dulbecco's Modified Eagle's Medium in the presence of additionally added 12 salts. The additional concentration of such provided salt is 40, 50, 60 or 70 mM. FIG. 8A shows the infectious center assay. FIG. 8B is a graph of the fold-change in the titers of AAV vectors and salt concentration. The Figure shows the fold-change in rAAV titer for rAAV that were produced in the presence of different anions and differing additionally provided concentrations of such anions. The concentration shown in the Figure is the concentration increase in the culturing medium provided by the addition of such anions.

FIG. 9B: fold-change in Total Genomes). The concentration shown in the Figure (40, 50, 60 or 70 mM) is the concentration increase in the culturing medium provided by the addition of such $KHCO_3$.

FIG. 11A: shows the fold-change of rAAV released into the medium after 24 hours; FIG. 11B shows the fold-change of total genomes of rAAV; $KHCO_3$-30 denotes that $KHCO_3$ was added to produce an additional concentration of 30 mM in the culturing medium; $KHCO_3$-55 denotes that $KHCO_3$ was added to produce an additional concentration of 55 mM in the culturing medium.

DETAILED DESCRIPTION OF THE INVENTION

I. The Methods of the Present Invention

The present invention is directed to methods for increasing the efficiencies with which recombinant adeno-associated virus (rAAV) are packaged, so as to increase their production titers. More specifically, the invention relates to a method for increasing the production titer of rAAV by transfected cells by increasing the ionic strength of the cell culture media through the administration of additional ions.

As used herein, the term "AAV" is intended to denote adeno-associated virus, and may be used to refer to the virus itself or derivatives thereof. The term covers all subtypes and both naturally-occurring and recombinant forms. As used herein, the term "rAAV" is intended to denote a recombinantly-modified version of AAV that comprises a polynucleotide sequence not of AAV origin (i.e., a polynucleotide heterologous to AAV). The rAAV may be single-stranded or double-stranded, and may be composed of deoxyribonucleotides or ribonucleotides.

Figure 1:
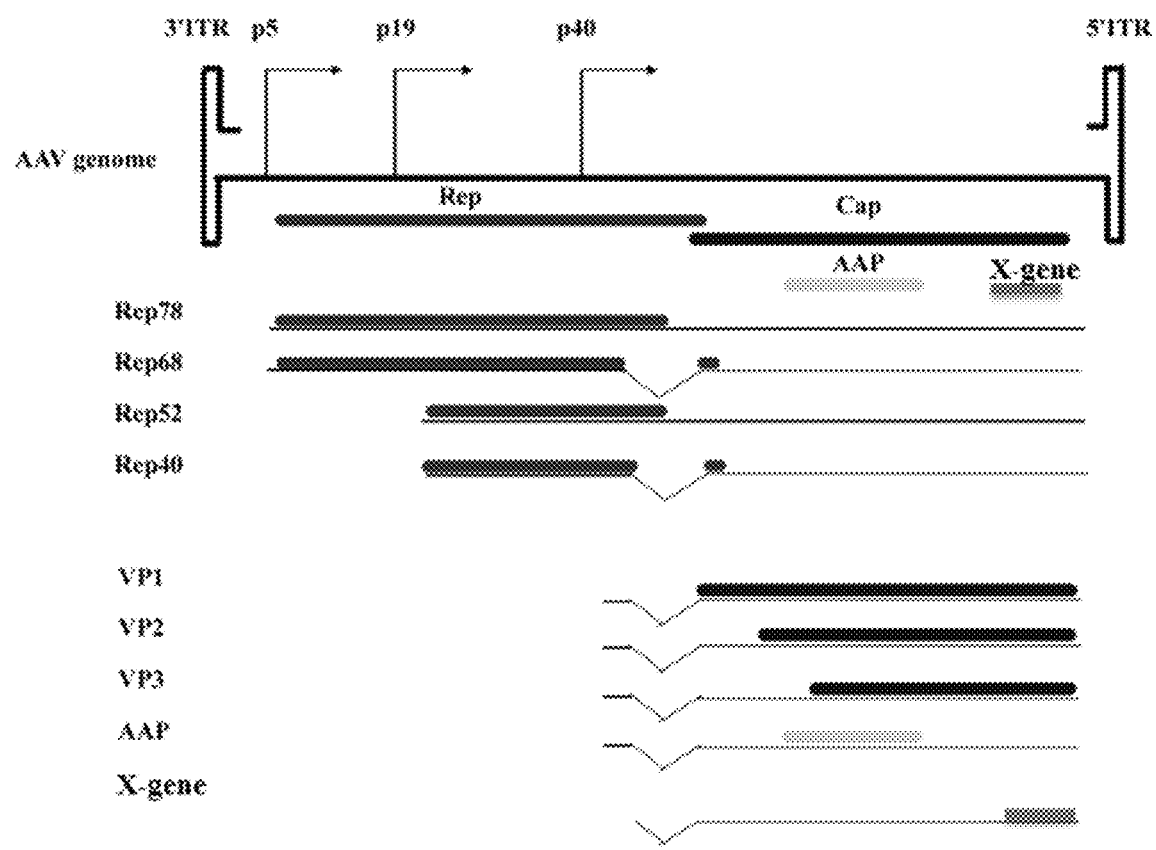
FIG. 1 provides a schematic genetic map of the wild-type (Wt) AAV genome.
Figure 2:
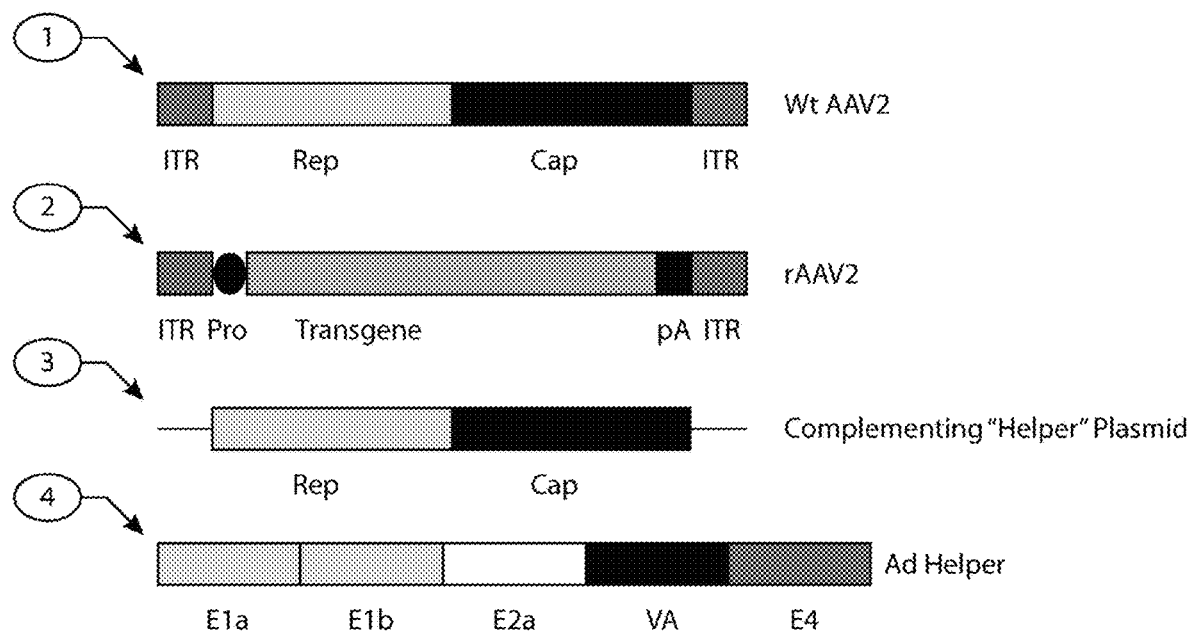
FIG. 2 provides a schematic of the structural domain of the wild-type AAV2 genome (1), a recombinant AAV (rAAV) (2), complementing "AAV helper plasmid" (3) and an adenovirus helper plasmid ("Ad helper plasmid") (4). The wild-type (Wt) AAV2 (1) is composed of AAV-specific palindromic inverted terminal repeated sequences (ITR), a 5' half containing genes that encode the Rep proteins and a 3' half containing genes that encode the Cap proteins. The rAAV (2) is formed by replacing the Rep- and Cap-encoding genes of the wild-type (Wt) AAV2 (1) with a transgene cassette that comprises a promoter (Pro), the exogenous transgene of interest, and a polyadenylation site (pA). In order to produce the rAAV (2), a complementing "AAV helper" plasmid vector (3) and an adenovirus helper plasmid vector (Ad helper plasmid) (4) are provided. The complementing AAV helper plasmid (3) provides Rep and Cap proteins. The Ad helper plasmid (4) provides adenovirus proteins E1a, E1b, E2a, VA and E4.
Figure 3:
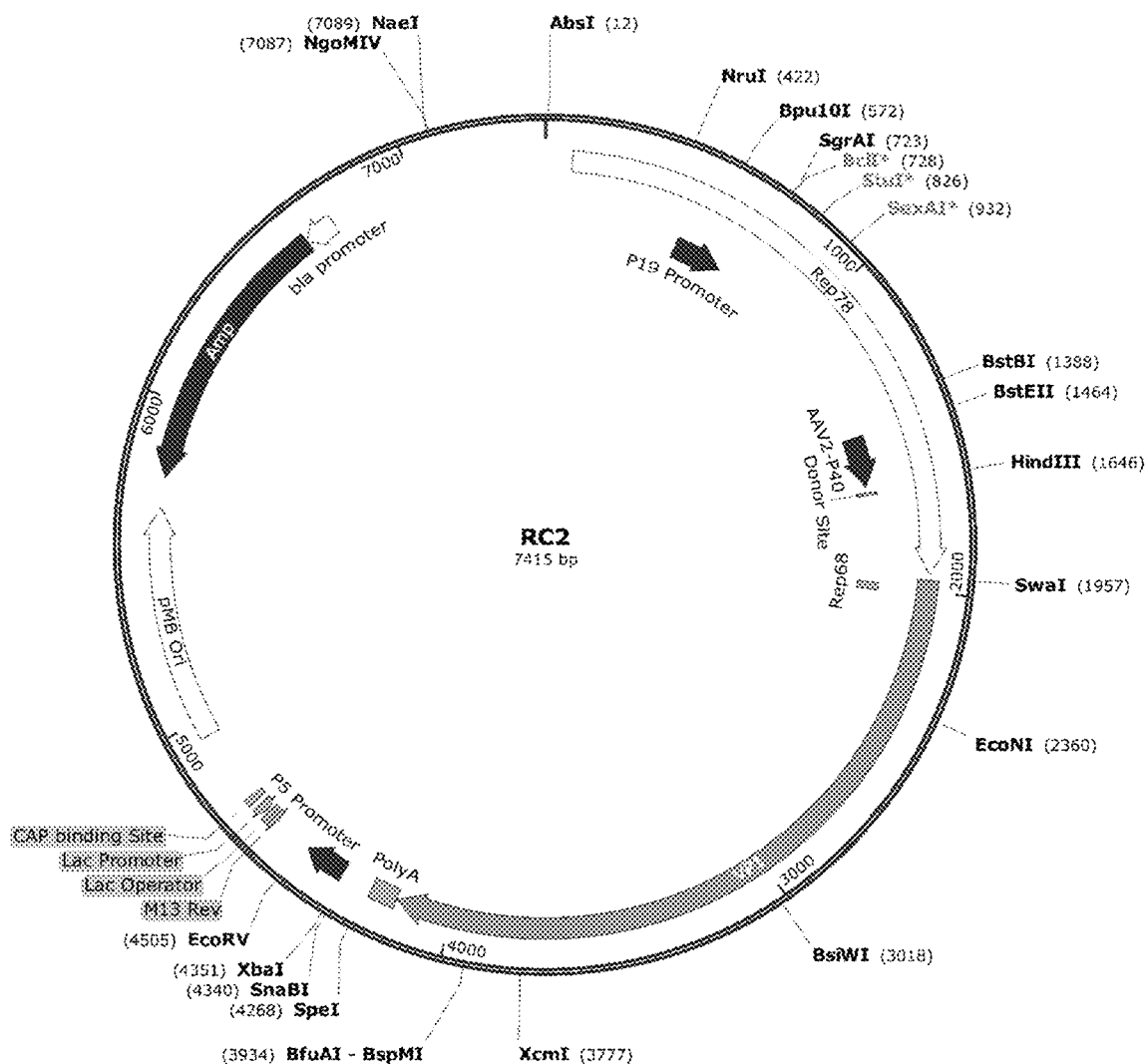
FIG. 3 shows a map of the AAV helper plasmid vector pAAV-RC2.

As used herein, the term "AAV helper functions" denotes AAV proteins (e.g., Rep and Cap) and/or polynucleotides of AAV that are required for the replication and packaging of an rAAV. Such AAV helper functions are provided by an "AAV helper function-providing polynucleotide," which as such term is used herein is a virus, plasmid vector, a non-plasmid vector, or a polynucleotide that has been integrated into a cellular chromosome, that provides AAV helper functions. AAV helper plasmids that may be used in accordance with the present invention to provide AAV helper functions, such as pAAV-RC (Agilent; Addgene; Cell Biolabs), pAAV-RC2 (Cell Biolabs), etc., are commercially available. Plasmid pAAV-RC2 (SEQ ID NO:1; FIG. 3) is an AAV helper plasmid that may be used in accordance with the present invention to provide AAV helper functions.

```
Coding Strand of Plasmid pAAV-RC2 (SEQ ID
NO: 1):
ccgggccccc cctcgaggtc gacggtatcg ggggagctcg
cagggtctcc attttgaagc gggaggtttg aacgcgcagc
cgccatgccg gggttttacg agattgtgat taaggtcccc
agcgaccttg acgagcatct gcccggcatt tctgacagct
ttgtgaactg ggtggccgag aaggaatggg agttgccgcc
agattctgac atggatctga atctgattga gcaggcaccc
ctgaccgtgg ccgagaagct gcagcgcgac tttctgacgg
aatggcgccg tgtgagtaag gccccgaggg ctctttttct
tgtgcaattt gagaagggag agagctactt ccacatgcac
gtgctcgtgg aaaccaccgg ggtgaaatcc atggttttgg
gacgtttcct gagtcagatt cgcgaaaaac tgattcagag
aatttaccgc gggatcgagc cgactttgcc aaactggttc
gcggtcacaa agaccagaaa tggcgccgga ggcgggaaca
aggtggtgga tgagtgctac atccccaatt acttgctccc
caaaacccag cctgagctcc agtgggcgtg gactaatatg
gaacagtatt taagcgcctg tttgaatctc acggagcgta
aacggttggt ggcgcagcat ctgacgcacg tgtcgcagac
gcaggagcag aacaaagaga atcagaatcc caattctgat
gcgccggtga tcagatcaaa aacttcagcc aggtacatgg
agctggtcgg gtggctcgtg gacaagggga ttacctcgga
gaagcagtgg atccaggagg accaggcctc atacatctcc
ttcaatgcgg cctccaactc gcggtcccaa atcaaggctg
ccttggacaa tgcggaaag attatgagcc tgactaaaac
cgcccccgac tacctggtgg ccagcagcc cgtggaggac
atttccagca tcggattta taaaattttg gaactaaacg
ggtacgatcc ccaatatgcg gcttccgtct ttctgggatg
ggcacgaaa aagttcggca agaggaacac catctggctg
tttgggcctg caactaccgg gaagaccaac atcgcggagg
ccatagccca cactgtgccc ttctacgggt gcgtaaactg
gaccaatgag aactttccct caacgactg tgtcgacaag
```

```
atggtgatct ggtgggagga ggggaagatg accgccaagg
tcgtggagtc ggccaaagcc attctcggag gaagcaaggt
gcgcgtggac cagaaatgca agtcctcggc ccagatagac
ccgactcccg tgatcgtcac ctccaacacc aacatgtgcg
ccgtgattga cgggaactca acgaccttcg aacaccagca
gccgttgcaa gaccggatgt tcaaatttga actcaccgc
cgtctggatc atgactttgg gaaggtcacc aagcaggaag
tcaaagactt tttccggtgg gcaaaggatc acgtggttga
ggtggagcat gaattctacg tcaaaaaggg tggagccaag
aaaagacccg cccccagtga cgcagatata agtgagccca
aacgggtgcg cgagtcagtt gcgcagccat cgacgtcaga
cgcggaagct tcgatcaact acgcagacag gtaccaaaac
aaatgttctc gtcacgtggg catgaatctg atgctgtttc
cctgcagaca atgcgagaga atgaatcaga attcaaatat
ctgcttcact cacggacaga aagactgttt agagtgcttt
cccgtgtcag aatctcaacc cgtttctgtc gtcaaaaagg
cgtatcagaa actgtgctac attcatcata tcatgggaaa
ggtgccagac gcttgcactg cctgcgatct ggtcaatgtg
gatttggatg actgcatctt gaacaataa atgatttaaa
tcaggtatgg ctgccgatgg ttatcttcca gattggctcg
aggacactct ctctgaagga ataagacagt ggtggaagct
caaacctggc ccaccaccac caaagcccgc agagcggcat
aaggacgaca gcaggggtct tgtgcttcct gggtacaagt
acctcggacc cttcaacgga ctcgacaagg gagagccggt
caacgaggca gacgccgcg ccctcgagca cgacaaagcc
tacgaccggc agctcgacag cggagacaac ccgtacctca
agtacaacca cgccgacgcg gagtttcagg agcgccttaa
agaagatacg tcttttgggg gcaacctcgg acgagcagtc
ttccaggcga aaaagagggt tcttgaacct ctgggcctgg
ttgaggaacc tgttaagacg gctccgggaa aaaagaggcc
ggtagagcac tctcctgtga gccagactc ctcctcggga
accggaaagg cgggccagca gcctgcaaga aaagattga
attttggtca gactggagac gcagactcag tacctgaccc
ccagcctctc ggacagccac cagcagcccc ctctggtctg
ggaactaata cgatggctac aggcagtggc gcaccaatgg
cagacaataa cgagggcgcc gacggagtgg gtaattcctc
gggaaattgg cattgcgatt ccacatggat gggcgacaga
gtcatcacca ccagcacccg aacctgggcc ctgcccacct
acaacaacca cctctacaaa caaatttcca gccaatcagg
agcctcgaac gacaatcact acttttggcta cagcaccccct
```

-continued

```
tgggggtatt ttgacttcaa cagattccac tgccactttt
caccacgtga ctggcaaaga ctcatcaaca caactgggg
attccgaccc aagagactca acttcaagct ctttaacatt
caagtcaaag aggtcacgca gaatgacggt acgacgacga
ttgccaataa ccttaccagc acggttcagg tgtttactga
ctcggagtac cagctcccgt acgtcctcgg ctcggcgcat
caaggatgcc tcccgccgtt cccagcagac gtcttcatgg
tgccacagta tggatacctc accctgaaca acgggagtca
ggcagtagga cgctcttcat tttactgcct ggagtacttt
ccttctcaga tgctgcgtac cggaaacaac tttaccttca
gctacacttt tgaggacgtt cctttccaca gcagctacgc
tcacagccag agtctggacc gtctcatgaa tcctctcatc
gaccagtacc tgtattactt gagcagaaca acactccaa
gtggaaccac cacgcagtca aggcttcagt tttctcaggc
cggagcgagt gacattcggg accagtctag gaactggctt
cctggaccct gttaccgcca gcagcgagta tcaaagacat
ctgcggataa caacaacagt gaatactcgt ggactggagc
taccaagtac caccctcaatg gcagagactc tctggtgaat
ccgggcccgg ccatggcaag ccacaaggac gatgaagaaa
agttttttcc tcagagcggg gttctcatct ttgggaagca
aggctcagag aaaacaaatg tggacattga aaaggtcatg
attacagacg aagaggaaat caggacaacc aatcccgtgg
ctacggagca gtatggttct gtatctacca acctccagag
aggcaacaga caagcagcta ccgcagatgt caacacacaa
ggcgttcttc caggcatggt ctggcaggac agagatgtgt
accttcaggg gcccatctgg gcaaagattc cacacacgga
cggacatttt caccctctc ccctcatggg tggattcgga
cttaaacacc ctcctccaca gattctcatc aagaacaccc
cggtacctgc gaatccttcg accaccttca gtgcggcaaa
gtttgcttcc ttcatcacac agtactccac gggacaggtc
agcgtggaga tcgagtggga gctgcagaag gaaaacagca
aacgctggaa tcccgaaatt cagtacactt ccaactacaa
caagtctgtt aatgtggact ttactgtgga cactaatggc
gtgtattcag agcctcgccc cattggcacc agatacctga
ctcgtaatct gtaattgctt gttaatcaat aaaccgttta
attcgtttca gttgaacttt ggtctctgcg tatttctttc
ttatctagtt tccatgctct aggatccact agtaacggcc
gccagtgtgc tggaattcgg ctttgtagtt aatgattaac
ccgccatgct acttatctac gtagccatgc tctagaggtc
ctgtattaga ggtcacgtga gtgttttgcg acattttgcg
acaccatgtg gtcacgctgg gtatttaagc ccgagtgagc
```

-continued

```
acgcagggtc tccattttga agcgggaggt ttgaacgcgc
agccgccaag ccgaattctg cagatatcca aacactggcg
gccgctcgac tagagcggcc gccaccgcgg tggagctcca
gcttttgttc cctttagtga gggttaattg cgcgcttggc
gtaatcatgg tcatagctgt ttcctgtgtg aaattgttat
ccgctcacaa ttccacacaa catacgagcc ggaagcataa
agtgtaaagc ctggggtgcc taatgagtga gctaactcac
attaattgcg ttgcgctcac tgcccgcttt ccagtcggga
aacctgtcgt gccagctgca ttaatgaatc ggccaacgcg
cggggagagg cggtttgcgt attgggcgct cttccgcttc
ctcgctcact gactcgctgc gctcggtcgt tcggctgcgg
cgagcggtat cagctcactc aaaggcggta atacggttat
ccacagaatc aggggataac gcaggaaaga acatgtgagc
aaaaggccag caaaaggcca ggaaccgtaa aaaggccgcg
ttgctggcgt ttttccatag gctccgcccc cctgacgagc
atcacaaaaa tcgacgctca agtcagaggt ggcgaaaccc
gacaggacta taaagatacc aggcgtttcc ccctggaagc
tccctcgtgc gctctcctgt tccgaccctg ccgcttaccg
gatacctgtc cgcctttctc ccttcgggaa gcgtggcgct
ttctcatagc tcacgctgta ggtatctcag ttcggtgtag
gtcgttcgct ccaagctggg ctgtgtgcac gaaccccccg
ttcagcccga ccgctgcgcc ttatccggta actatcgtct
tgagtccaac ccggtaagac acgacttatc gccactggca
gcagccactg gtaacaggat tagcagagcg aggtatgtag
gcggtgctac agagttcttg aagtggtggc ctaactacgg
ctacactaga agaacagtat ttggtatctg cgctctgctg
aagccagtta ccttcggaaa aagagttggt agctcttgat
ccggcaaaca aaccaccgct ggtagcggtg gtttttttgt
ttgcaagcag cagattacgc gcagaaaaaa aggatctcaa
gaagatcctt tgatctttc tacggggtct gacgctcagt
ggaacgaaaa ctcacgttaa gggattttgg tcatgagatt
atcaaaaagg atcttcacct agatcctttt aaattaaaaa
tgaagtttta atcaatcta agtatatat gagtaaactt
ggtctgacag ttaccaatgc ttaatcagtg aggcacctat
ctcagcgatc tgtctatttc gttcatccat agttgcctga
ctccccgtcg tgtagataac tacgatacgg gagggcttac
catctggccc cagtgctgca atgataccgc gagacccacg
ctcaccggct ccagatttat cagcaataaa ccagccagcc
ggaagggccg agcgcagaag tggtcctgca actttatccg
cctccatcca gtctattaat tgttgccggg aagctagagt
```

-continued

```
aagtagttcg ccagttaata gtttgcgcaa cgttgttgcc attgctacag gcatcgtggt gtcacgctcg tcgtttggta tggcttcatt cagctccggt tcccaacgat caaggcgagt tacatgatcc cccatgttgt gcaaaaaagc ggttagctcc ttcggtcctc cgatcgttgt cagaagtaag ttggccgcag tgttatcact catggttatg gcagcactgc ataattctct tactgtcatg ccatccgtaa gatgcttttc tgtgactggt gagtactcaa ccaagtcatt ctgagaatag tgtatgcggc gaccgagttg ctcttgcccg gcgtcaatac gggataatac cgcgccacat agcagaactt taaaagtgct catcattgga aaacgttctt cggggcgaaa actctcaagg atcttaccgc tgttgagatc cagttcgatg taacccactc gtgcacccaa ctgatcttca gcatcttttta ctttcaccag cgtttctggg tgagcaaaaa caggaaggca aaatgccgca aaaaagggaa taagggcgac acggaaatgt tgaatactca tactcttcct ttttcaatat tattgaagca tttatcaggg ttattgtctc atgagcggat acatatttga atgtatttag aaaaataaac aaatagggt tccgcgcaca tttccccgaa aagtgccacc taaattgtaa gcgttaatat tttgttaaaa ttcgcgttaa attttttgtta aatcagctca tttttttaacc aataggccga aatcggcaaa atcccttata aatcaaaaga atagaccgag atagggttga gtgttgttcc agtttggaac aagagtccac tattaaagaa cgtggactcc aacgtcaaag ggcgaaaaac cgtctatcag ggcgatggcc cactacgtga accatcaccc taatcaagtt ttttggggtc gaggtgccgt aaagcactaa atcggaaccc taaagggagc ccccgattta gagcttgacg gggaaagccg gcgaacgtgg cgagaaagga agggaagaaa gcgaaaggag cgggcgctag ggcgctggca agtgtagcgg tcacgctgcg cgtaaccacc acacccgccg cgcttaatgc gccgctacag ggcgcgtccc attcgccatt caggctgcgc aactgttggg aagggcgatc ggtgcgggcc tcttcgctat tacgccagct ggcgaaaggg ggatgtgctg caaggcgatt aagttgggta acgccagggt tttcccagtc acgacgttgt aaaacgacgg ccagtgagcg cgcgtaaatc gactcactat agggcgaatt gggta
```

In SEQ ID NO:1, residues 85-1950 of pAAV-RC2 encode the Rep protein, Rep78 (with residues 484-663 corresponding to the P19 promoter, residues 1464-1643 corresponding to the P40 promoter and residues 1668-1676 being a donor site); residues 1967-4174 encode the capsid protein, VP1; residues 1992-2016 encodes a portion of the Rep68 protein; residues 4175-4256 encode a polyA sequence; residues 4610-4626 are M13 Rev sequences; residues 4634-4650 are Lac operator sequences; 4658-4688 are Lac promoter sequences; residues 4951-5675 correspond to pMB ori sequences, residues 5771-6631 encode an ampicillin resistance determinant; and residues 6632-6730 are bla promoter sequences (FIG. 3).

Figure 4:
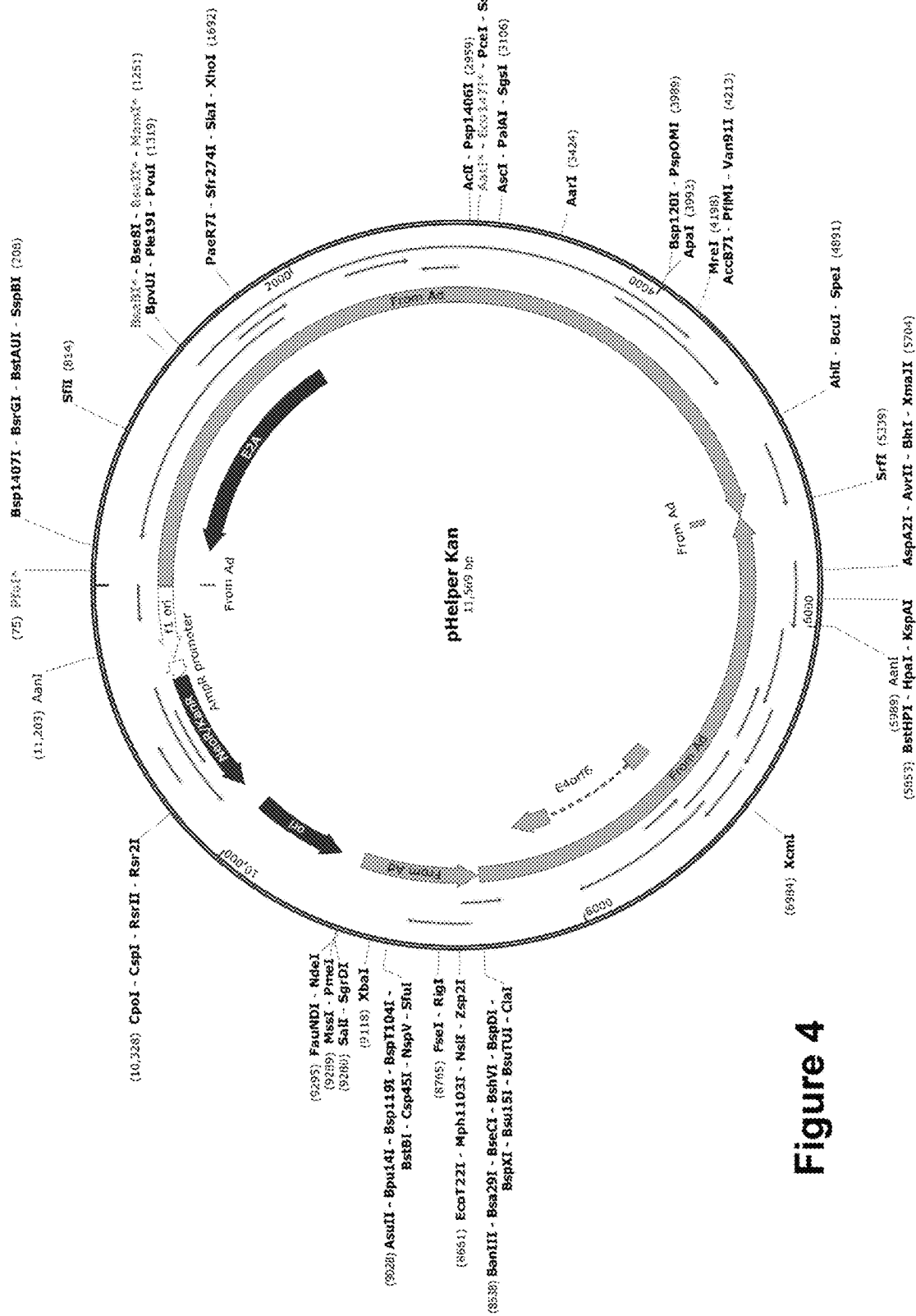
FIG. 4 shows a map of the non-AAV helper plasmid vector pHelper-Kan.

As used herein, the term "non-AAV helper functions" denotes proteins of Ad, CMV, HSV or other non-AAD viruses (e.g., E1a, E1b, E2a, VA and E4) and/or polynucleotides of Ad, CMV, HSV or other non-AAD viruses that are required for the replication and packaging of an rAAV. Such non-AAV helper functions are provided by a "non-AAV helper function-providing polynucleotide," which as such term is used herein is a virus, plasmid vector, a non-plasmid vector, or a polynucleotide that has been integrated into a cellular chromosome, that provides non-AAV helper functions. The vector, pHelper and derivatives thereof (commercially available from Cell Biolabs, Inc., Invitrogen and Stratagene) are suitable non-AAV helper function-providing polynucleotide (see, e.g., Matsushita, T. et al. (1998) "*Adeno Associated Virus Vectors Can Be Efficiently Produced Without Helper Virus,*" Gene Ther. 5:938-945; Sharma, A. et al. (2010) "*Transduction Efficiency Of AAV 2/6, 2/8 And 2/9 Vectors For Delivering Genes In Human Corneal Fibroblasts,*" Brain Res. Bull. 81(2-3):273-278). Plasmid pHelper-Kan (SEQ ID NO:2; FIG. 4) is a non-AAV helper function-providing polynucleotide that may be used in accordance with the present invention to provide non-AAV helper functions.

```
Coding Strand of Plasmid pHelper-Kan (SEQ ID
NO: 2):
ggtacccaac tccatgctta acagtcccca ggtacagccc accctgcgtc gcaaccagga acagctctac agcttcctgg agcgccactc gccctacttc cgcagccaca gtgcgcagat taggagcgcc acttcttttt gtcacttgaa aaacatgtaa aaataatgta ctaggagaca ctttcaataa aggcaaatgt ttttatttgt acactctcgg gtgattattt accccccacc cttgccgtct gcgccgttta aaaatcaaag gggttctgcc gcgcatcgct atgcgccact ggcagggaca cgttgcgata ctggtgttta gtgctccact taaactcagg cacaaccatc cgcggcagct cggtgaagtt ttcactccac aggctgcgca ccatcaccaa cgcgtttagc aggtcgggcg ccgatatctt gaagtcgcag ttggggcctc cgccctgcgc gcgcgagttg cgatacacag ggttgcagca ctggaacact atcagcgccg ggtggtgcac gctggccagc acgctcttgt cggagatcag atccgcgtcc aggtcctccg cgttgctcag ggcgaacgga gtcaacttgt gtagctgcct tccccaaaaag ggtgcatgcc caggctttga gttgcactcg caccgtagtg gcatcagaag gtgaccgtgc ccggtctggg cgttaggata cagcgcctgc atgaaagcct tgatctgctt aaaagccacc tgagcctttg cgccttcaga gaagaacatg ccgcaagact tgccggaaaa ctgattggcc ggacaggccg cgtcatgcac gcagcacctt gcgtcggtgt tggagatctg caccacattt cggccccacc ggttcttcac gatcttggcc ttgctagact gctccttcag
```

-continued

```
cgcgcgctgc cgttttcgc tcgtcacatc catttcaatc
acgtgctcct tatttatcat aatgctcccg tgtagacact
taagctcgcc ttcgatctca gcgcagcggt gcagccacaa
cgcgcagccc gtgggctcgt ggtgcttgta ggttacctct
gcaaacgact gcaggtacgc ctgcaggaat cgccccatca
tcgtcacaaa ggtcttgttg ctggtgaagt tcagctgcaa
cccgcggtgc tcctcgttta gccaggtctt gcatacggcc
gccagagctt ccacttggtc aggcagtagc ttgaagtttg
cctttagatc gttatccacg tggtacttgt ccatcaacgc
gcgcgcagcc tccatgccct ctcccacgc agacacgatc
ggcaggctca gcgggtttat caccgtgctt tcactttccg
cttcactgga ctcttccttt tcctcttgcg tccgcatacc
ccgcgccact gggtcgtctt cattcagccg ccgcaccgtg
cgcttacctc ccttgccgtg cttgattagc accggtgggt
tgctgaaacc caccatttgt agcgccacat cttctctttc
ttcctcgctg tccacgatca cctctgggga tggcgggcgc
tcgggcttgg gagaggggcg cttcttttc ttttggacg
caatggccaa atccgccgtc gaggtcgatg gccgcgggct
gggtgtgcgc ggcaccagcg catcttgtga cgagtcttct
tcgtcctcgg actcgagacg ccgcctcagc cgcttttttg
ggggcgcgcg gggaggcggc ggcgacggcg acggggacga
cacgtcctcc atggttggtg gacgtcgcgc cgcaccgcgt
ccgcgctcgg gggtggttc gcgctgctcc tcttcccgac
tggccatttc cttctcctat aggcagaaaa agatcatgga
gtcagtcgag aaggaggaca gcctaaccgc ccccttgag
ttcgccacca ccgcctccac cgatgccgcc aacgcgccta
ccaccttccc cgtcgaggca ccccgcttg aggaggagga
agtgattatc gagcaggacc caggttttgt aagcgaagac
gacgaggatc gctcagtacc aacagaggat aaaaagcaag
accaggacga cgcagaggca aacgaggaac aagtcgggcg
ggggggaccaa aggcatggcg actacctaga tgtgggagac
gacgtgctgt tgaagcatct gcagcgccag tgcgccatta
tctgcgacgc gttgcaagag cgcagcgatg tgccctcgc
catagcggat gtcagccttg cctacgaacg ccacctgttc
tcaccgcgcg taccccccaa acgcaagaa aacggcacat
gcgagcccaa cccgcgcctc aacttctacc ccgtatttgc
cgtgccagag gtgcttgcca cctatcacat ctttttccaa
aactgcaaga taccctatc ctgccgtgcc aaccgcagcc
gagcggacaa gcagctggcc ttgcggcagg gcgctgtcat
acctgatatc gcctcgctcg acgaagtgcc aaaaatcttt
```

-continued

```
gagggtcttg gacgcgacga gaaacgcgcg gcaaacgctc
tgcaacaaga aaacagcgaa aatgaaagtc actgtggagt
gctggtggaa cttgagggtg acaacgcgcg cctagccgtg
ctgaaacgca gcatcgaggt cacccacttt gcctaccgg
cacttaacct acccccaag gttatgagca cagtcatgag
cgagctgatc gtgcgccgtg cacgacccct ggagagggat
gcaaacttgc aagaacaaac cgaggagggc ctacccgcag
ttggcgatga gcagctggcg cgctggcttg agacgcgcga
gcctgccgac ttggaggagc gacgcaagct aatgatggcc
gcagtgcttg ttaccgtgga gcttgagtgc atgcagcggt
tctttgctga cccggagatg cagcgcaagc tagaggaaac
gttgcactac accttccgcc agggctacgt gcgccaggcc
tgcaaaattt ccaacgtgga gctctgcaac ctggtctcct
accttggaat tttgcacgaa aaccgcctcg ggcaaaacgt
gcttcattcc acgctcaagg gcgaggcgcg ccgcgactac
gtccgcgact gcgtttactt atttctgtgc tacacctggc
aaacggccat gggcgtgtgg cagcaatgcc tggaggagcg
caacctaaag gagctgcaga gctgctaaa gcaaaacttg
aaggacctat ggacggcctt caacgagcgc tccgtggccg
cgcacctggc ggacattatc ttccccgaac gcctgcttaa
aaccctgcaa cagggtctgc cagacttcac cagtcaaagc
atgttgcaaa actttaggaa ctttatccta gagcgttcag
gaattctgcc cgccacctgc tgtgcgcttc ctagcgactt
tgtgcccatt aagtaccgtg aatgccctcc gccgctttgg
ggtcactgct accttctgca gctagccaac taccttgcct
accactccga catcatggaa gacgtgagcg gtgacggcct
actggagtgt cactgtcgct gcaacctatg cacccccgcac
cgctccctgg tctgcaattc gcaactgctt agcgaaagtc
aaattatcgg taccttgag ctgcagggtc cctcgcctga
cgaaaagtcc gcggctccgg ggttgaaact cactccgggg
ctgtgacgt cggcttacct tcgcaaattt gtacctgagg
actaccacgc ccacgagatt aggttctacg aagaccaatc
ccgccccgcca aatgcggagc ttaccgcctg cgtcattacc
cagggccaca tccttggcca attgcaagcc atcaacaaag
cccgccaaga gtttctgcta cgaaagggac ggggggttta
cctggacccc cagtccggcg aggagctcaa cccaatcccc
ccgccgccgc agccctatca gcagccgcgg gcccttgctt
cccaggatgg cacccaaaaa gaagctgcag ctgccgccgc
cgccacccac ggacgaggag gaatactggg acagtcaggc
agaggaggtt ttggacgagg aggaggagat gatggaagac
tgggacagcc tagacgaagc ttccgaggcc gaagaggtgt
```

-continued

```
cagacgaaac accgtcaccc tcggtcgcat tccctcgcc
ggcgcccag aaattggcaa ccgttcccca catcgctaca
acctccgctc ctcaggcgcc gccggcactg cctgttcgcc
gacccaaccg tagatgggac accactggaa ccaggccgg
taagtctaag cagccgccgc cgttagccca agagcaacaa
cagcgccaag gctaccgctc gtggcgcggg cacaagaacg
ccatagttgc ttgcttgcaa gactgtgggg gcaacatctc
cttcgcccgc cgcttcttc tctaccatca cggcgtggcc
ttcccccgta acatcctgca ttactaccgt catctctaca
gccctactg caccggcggc agcggcagcg gcagcaacag
cagcggtcac acagaagcaa aggcgaccgg atagcaagac
tctgacaaag cccaagaaat ccacagcggc ggcagcagca
ggaggaggag cgctgcgtct ggcgcccaac gaacccgtat
cgacccgcga gcttagaaat aggatttttc ccactctgta
tgctatattt caacaaagca ggggccaaga acaagagctg
aaaataaaaa acaggtctct gcgctccctc accccgcagct
gcctgtatca caaaagcgaa gatcagcttc ggcgcacgct
ggaagacgcg gaggctctct tcagcaaata ctgcgcgctg
actcttaagg actagtttcg cgccctttct caaatttaag
cgcgaaaact acgtcatctc cagcggccac accggcgcc
agcacctgtc gtcagcgcca ttatgagcaa ggaaattccc
acgccctaca tgtggagtta ccagccacaa atgggacttg
cggctggagc tgcccaagac tactcaaccc gaataaacta
catgagcgcg gaccccaca tgatatcccg ggtcaacgga
atccgcgccc accgaaaccg aattctcctc gaacaggcgg
ctattaccac cacacctcgt aataaccta atccccgtag
ttggcccgct gccctggtgt accaggaaag tcccgctccc
accactgtgg tacttccag agacgcccag gccgaagttc
agatgactaa ctcaggggcg cagcttgcgg gcggctttcg
tcacagggtg cggtcgcccg ggcgttttag ggcggagtaa
cttgcatgta ttgggaattg tagtttttt aaaatgggaa
gtgacgtatc gtgggaaaac ggaagtgaag atttgaggaa
gttgtgggtt ttttggcttt cgttctggg cgtaggttcg
cgtgcggttt tctgggtgtt ttttgtggac tttaaccgtt
acgtcatttt ttagtcctat atatactcgc tctgtacttg
gccctttta cactgtgact gattgagctg gtgccgtgtc
gagtggtgtt ttttaatagg tttttttact ggtaaggctg
actgttatgg ctgccgctgt ggaagcgctg tatgttgttc
tggagcggga gggtgctatt ttgcctaggc aggagggttt
tcaggtgtt tatgtgttt tctctcctat taattttgtt
```

```
atacctccta tgggggctgt aatgttgtct ctacgcctgc
gggtatgtat tccccgggc tatttcggtc gcttttagc
actgaccgat gttaaccaac ctgatgtgtt taccgagtct
tacattatga ctccggacat gaccgaggaa ctgtcggtgg
tgcttttaa tcacggtgac cagttttttt acggtcacgc
cggcatggcc gtagtccgtc ttatgcttat aagggttgtt
tttcctgttg taagacaggc ttctaatgtt taaatgtttt
tttttttgtt attttatttt gtgtttaatg caggaacccg
cagacatgtt tgagagaaaa atggtgtctt tttctgtggt
ggttccgaa cttacctgcc tttatctgca tgagcatgac
tacgatgtgc ttgctttttt gcgcgaggct ttgcctgatt
ttttgagcag caccttgcat tttatatcgc cgcccatgca
acaagcttac ataggggcta cgctggttag catagctccg
agtatgcgtg tcataatcag tgtgggttct tttgtcatgg
ttcctggcgg ggaagtggcc gcgctggtcc gtgcagacct
gcacgattat gttcagctgg ccctgcgaag ggacctacgg
gatcgcgta ttttgttaa tgttccgctt tgaatctta
tacaggtctg tgaggaacct gaattttgc aatcatgatt
cgctgcttga ggctgaaggt ggagggcgct ctggagcaga
tttttacaat ggccggactt aatattcggg atttgcttag
agacatattg ataaggtggc gagatgaaaa ttatttgggc
atggttgaag gtgctggaat gtttatagag gagattcacc
ctgaagggtt tagcctttac gtccacttgg acgtgagggc
agtttgcctt ttggaagcca ttgtgcaaca tcttacaaat
gccattatct gttctttggc tgtagagttt gaccacgcca
ccggagggga gcgcgttcac ttaatagatc ttcattttga
ggttttggat aatcttttgg aataaaaaaa aaaaaacatg
gttcttccag ctcttcccgc tcctccgtg tgtgactcgc
agaacgaatg tgtaggttgg ctgggtgtgg cttattctgc
ggtggtggat gttatcaggg cagcggcgca tgaaggagtt
tacatagaac ccgaagccag ggggcgcctg gatgctttga
gagagtggat atactacaac tactacacag agcgagctaa
gcgacgagac cggagacgca gatctgtttg tcacgcccgc
acctggtttt gcttcaggaa atatgactac gtccggcgtt
ccatttggca tgacactacg accaacacga tctcggttgt
ctcggcgcac tccgtacagt agggatcgcc tacctccttt
tgagacagag acccgcgcta ccatactgga ggatcatccg
ctgctgcccg aatgtaacac tttgacaatg cacaacgtga
gttacgtgcg aggtcttccc tgcagtgtgg gatttacgct
gattcaggaa tgggttgttc cctgggatat ggttctgacg
cgggaggagc ttgtaatcct gaggaagtgt atgcacgtgt
```

-continued

```
gcctgtgttg tgccaacatt gatatcatga cgagcatgat
gatccatggt tacgagtcct gggctctcca ctgtcattgt
tccagtcccg gttccctgca gtgcatagcc ggcgggcagg
ttttggccag ctggtttagg atggtggtgg atggcgccat
gtttaatcag aggtttatat ggtaccggga ggtggtgaat
tacaacatgc caaaagaggt aatgtttatg tccagcgtgt
ttatgagggg tcgccactta atctacctgc gcttgtggta
tgatgccac gtgggttctg tggtccccgc catgagcttt
ggatacagcg ccttgcactg tgggattttg aacaatattg
tggtgctgtg ctgcagttac tgtgctgatt taagtgagat
cagggtgcgc tgctgtgccc ggaggacaag gcgtctcatg
ctgcgggcgg tgcgaatcat cgctgaggag accactgcca
tgttgtattc ctgcaggacg gagcggcggc ggcagcagtt
tattcgcgcg ctgctgcagc accaccgccc tatcctgatg
cacgattatg actctacccc catgtaggcg tggacttccc
cttcgccgcc cgttgagcaa ccgcaagttg gacagcagcc
tgtggctcag cagctggaca gcgacatgaa cttaagcgag
ctgcccgggg agtttattaa tatcactgat gagcgtttgg
ctcgacagga aaccgtgtgg aatataacac ctaagaatat
gtctgttacc catgatatga tgctttttaa ggccagccgg
ggagaaagga ctgtgtactc tgtgtgttgg gagggaggtg
gcaggttgaa actaggggtt ctgtgagttt gattaaggta
cggtgatcaa tataagctat gtggtggtgg ggctatacta
ctgaatgaaa aatgacttga aattttctgc aattgaaaaa
taaacacgtt gaaacataac atgcaacagg ttcacgattc
tttattcctg ggcaatgtag gagaaggtgt aagagttggt
agcaaaagtt tcagtggtgt attttccact ttcccaggac
catgtaaaag acatagagta agtgcttacc tcgctagttt
ctgtggattc actagaatcg atgtaggatg ttgcccctcc
tgacgcggta ggagaagggg agggtgccct gcatgtctgc
cgctgctctt gctcttgccg ctgctgagga ggggggcgca
tctgccgcag caccggatgc atctgggaaa agcaaaaaag
gggctcgtcc ctgtttccgg aggaatttgc aagcgggtc
ttgcatgacg gggaggcaaa ccccgttcg ccgcagtccg
gccggcccga gactcgaacc gggggtcctg cgactcaacc
cttggaaaat aaccctccgg ctacagggag cgagccactt
aatgctttcg cttttccagcc taaccgctta cgccgcgcgc
ggccagtggc caaaaagct agcgcagcag ccgccgcgcc
tggaaggaag ccaaaaggag cgctcccccg ttgtctgacg
tcgcacacct gggttcgaca cgcgggcggt aaccgcatgg
```

-continued

```
atcacggcgg acggccggat ccggggttcg aacccggtc
gtccgccatg ataccccttgc gaatttatcc accagaccac
ggaagagtgc ccgcttacag gctctccttt tgcacggtct
agagcgtcaa cgactgcgca cgcctcaccg gccagagcgt
cccgaccatg gagcactttt tgccgctgcg caacatctgg
aaccgcgtcc gcgactttcc gcgcgcctcc accaccgccg
ccggcatcac ctggatgtcc aggtacatct acggattacg
tcgacgttta aaccatatga tcagctcact caaaggcggt
aatacggtta tccacagaat caggggataa cgcaggaaag
aacatgtgag caaaaggcca gcaaaaggcc aggaaccgta
aaaaggccgc gttgctggcg ttttttccata ggctccgccc
ccctgacgag catcacaaaa atcgacgctc aagtcagagg
tggcgaaacc cgacaggact ataaagatac caggcgtttc
cccctggaag ctccctcgtg cgctctcctg ttccgaccct
gccgcttacc ggatacctgt ccgcctttct cccttcggga
agcgtggcgc tttctcatag ctcacgctgt aggtatctca
gttcggtgta ggtcgttcgc tccaagctgg gctgtgtgca
cgaaccccc gttcagcccg accgctgcgc cttatccggt
aactatcgtc ttgagtccaa cccggtaaga cacgacttat
cgccactggc agcagccact ggtaacagga ttagcagagc
gaggtatgta ggcggtgcta cagagttctt gaagtggtgg
cctaactacg gctacactag aagaacagta tttggtatct
gcgctctgct gaagccagtt accttcggaa aaagagttgg
tagctcttga tccggcaaac aaaccaccgc tggtagcggt
ggttttttg tttgcaagca gcagattacg cgcagaaaaa
aaggatctca agaagatcct ttgatctttt ctacggggtc
tgacgctcag tggaacgaaa actcacgtta agggattttg
gtcatgagat tatcaaaaag gatcttcacc tagatccttt
taaattaaaa atgaagtttt aaatcaatct aaagtatata
tgagtaaact tggtctgaca gtcagaagaa ctcgtcaaga
aggcgataga aggcgatgcg ctgcgaatcg ggagcggcga
taccgtaaag cacgaggaag cggtcagccc attcgccgcc
aagctcttca gcaatatcac gggtagccaa cgctatgtcc
tgatagcggt ccgccacacc cagccggcca cagtcgatga
atccagaaaa gcggccattt ccaccatga tattcggcaa
gcaggcatcg ccatgggtca cgacgagatc ctcgccgtcg
ggcatgctcg ccttgagcct ggcgaacagt tcggctggcg
cgagccctg atgtctcttg tccagatcat cctgatcgac
aagaccggct tccatccgag tacgtgctcg ctcgatgcga
tgtttcgctt ggtggtcgaa tgggcaggta gccggatcaa
gcgtatgcag ccgccgcatt gcatcagcca tgatggatac
```

-continued

```
tttctcggca ggagcaaggt gagatgacag gagatcctgc cccggcactt cgcccaatag cagccagtcc cttcccgctt cagtgacaac gtcgagtaca gctgcgcaag gaacgcccgt cgtggccagc cacgatagcc gcgctgcctc gtcttgcagt tcattcaggg caccggacag gtcggtcttg acaaaaagaa ccgggcgccc ctgcgctgac agccggaaca cggcggcatc agagcagccg attgtctgtt gtgcccagtc atagccgaat agcctctcca cccaagcggc cggagaacct gcgtgcaatc catcttgttc aatcatactc ttcctttttc aatattattg aagcatttat cagggttatt gtctcatgag cggatacata tttgaatgta tttagaaaaa taaacaaata ggggttccgc gcacatttcc ccgaaaagtg ccacctaaat tgtaagcgtt aatattttgt taaaattcgc gttaaatttt tgttaaatca gctcattttt taaccaatag gccgaaatcg gcaaaatccc ttataaatca aaagaataga ccgagatagg gttgagtgtt gttccagttt ggaacaagag tccactatta aagaacgtgg actccaacgt caaagggcga aaaaccgtct atcagggcga tggcccacta cgtgaaccat caccctaatc aagttttttg gggtcgaggt gccgtaaagc actaaatcgg aaccctaaag ggagccccg atttagagct tgacggggaa agccggcgaa cgtggcgaga aaggaaggga agaaagcgaa aggagcgggc gctagggcgc tggcaagtgt agcggtcacg ctgcgcgtaa ccaccacacc cgccgcgctt aatgcgccgc tacagggcgc gatggatcc
```

In SEQ ID NO:2, residues 1-5343 of pHelper-Kan are derived from adenovirus, and include a polynucleotide encoding the E2A protein (residues 258-1847); residues 5344-8535 are derived from adenovirus, and include a polynucleotide encoding the E4orf6 protein; residues 9423-10011 correspond to ori sequences; residues 10182-10976 encode a kanamycin resistance determinant expressed by a bla promoter sequence (residues 10977-11081); residues 11107-11561 correspond to f1 ori sequences (FIG. 4).

Figure 5:
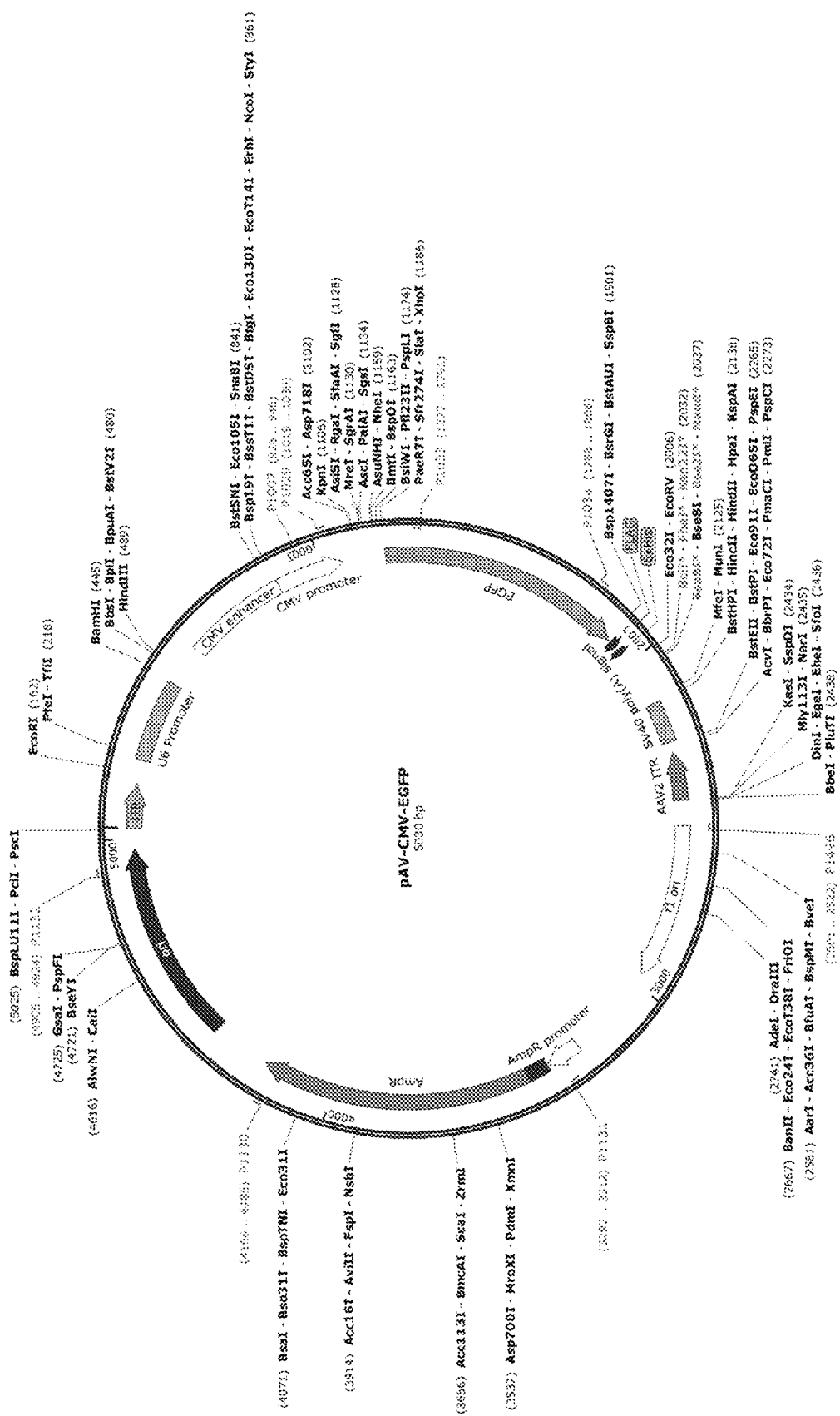
FIG. 5 shows a map of the rAAV plasmid vector pAV-CMV-EGFP.

As discussed above, AAV helper function-providing polynucleotides and non-AAV helper function-providing polynucleotides are typically employed in concert with an rAAV plasmid vector to comprise a triple plasmid transfection system. Multiple commercially available rAAV plasmid vectors (e.g., pAV-CMV-EGFP, pGOI, etc. (Cell Biolabs, Inc., Invitrogen and Stratagene)) may be used in accordance with the present invention. An illustrative rAAV plasmid vector that may be used in accordance with the present invention is pAV-CMV-EGFP (SEQ ID NO:3; FIG. 5) which comprises a 5' ITR, a U6 promoter, CMV enhancer and promoter sequences, a polynucleotide encoding the enhanced green fluorescent protein (EGFP) (Gambotto, A. et al. (2000) "*Immunogenicity Of Enhanced Green Fluorescent Protein (EGFP) In BALB/C Mice: Identification Of An H2-Kd-Restricted CTL Epitope*," Gene Ther. 7(23):2036-2040; Tsien, R. Y. (1998) "*The Green Fluorescent Protein*," Annu. Rev. Biochem. 67:509-544; Cinelli, R. A. et al. (2000) "*The Enhanced Green Fluorescent Protein As A Tool For The Analysis Of Protein Dynamics And Localization: Local Fluorescence Study At The Single-Molecule Level*," Photochem. Photobiol. 71(6):771-776; Chopra A. (2008) "*Recombinant Adenovirus With Enhanced Green Fluorescent Protein*," In: MOLECULAR IMAGING AND CONTRAST AGENT DATABASE (MICAD), National Center for Biotechnology Information, Bethesda Md.), FLAG-tag and 6×His-tag sites for facilitating recovery or localization of expressed proteins, an SV40 poly(A) site and a 3' ITR.

```
Coding Strand of Plasmid pAV-CMV-EGFP (SEQ ID
NO: 3):
cctgcaggca gctgcgcgct cgctcgctca ctgaggccgc ccgggcgtcg ggcgaccttt ggtcgcccgg ccctccagtg agcgagcgcg cagagaggga gtggccaact ccatcactag gggttcctgc ggccgcacgc gtctagttat taatagtaat cgaattcgtg ttactcataa ctagtaaggt cgggcaggaa gagggcctat ttcccatgat tccttcatat ttgcatatac gatacaaggc tgttagagag ataattagaa ttaatttgac tgtaaacaca aagatattag tacaaaatac gtgacgtaga aagtaataat ttcttgggta gtttgcagtt ttaaaattat gtttttaaaat ggactatcat atgcttaccg taacttgaaa gtatttcgat ttcttggggtt tatatatctt gtggaaagga cgcgggatcc actggaccag gcagcagcgt cagaagactt ttttgaaaaa gcttgactag taatactgta atagtaatca attacggggt cattagttca tagcccatat atggagttcc gcgttacata acttacggta aatggcccgc ctggctgacc gcccaacgac ccccgcccat tgacgtcaat aatgacgtat gttcccatag taacgccaat agggactttc cattgacgtc aatgggtgga gtatttacgg taaactgccc acttggcagt acatcaagtg tatcatatgc caagtacgcc ccctattgac gtcaatgacg gtaaatggcc cgcctggcat tatgcccagt acatgacctt atgggacttt cctacttggc agtacatcta cgtattagtc atcgctatta ccatggtgat gcggttttgg cagtacatca atgggcgtgg atagcggttt gactcacggg gatttccaag tctccacccc attgacgtca atgggagttt gttttgcacc aaaatcaacg ggactttcca aaatgtcgta acaactccgc cccattgacg caaatgggcg gtaggcgtgt acggtgggag gtctatataa gcagagctgg tttagtgaac cgtcagatcc gctagagatc cggtaccgag gagatctgcc gccgcgatcg ccggcgcgcc agatctcacg cttaactagc tagcggaccg acgcgtacgc ggccgctcga gatggtgagc aagggcgagg agctgttcac cggggtggtg cccatcctgg tcgagctgga cggcgacgta aacggccaca gttcagcgt
```

-continued

```
gtccggcgag ggcgagggcg atgccaccta cggcaagctg
accctgaagt tcatctgcac caccggcaag ctgcccgtgc
cctggcccac cctcgtgacc accctgacct acggcgtgca
gtgcttcagc cgctaccccg accacatgaa gcagcacgac
ttcttcaagt ccgccatgcc cgaaggctac gtccaggagc
gcaccatctt cttcaaggac gacggcaact acaagacccg
cgccgaggtg aagttcgagg gcgacaccct ggtgaaccgc
atcgagctga agggcatcga cttcaaggag gacggcaaca
tcctggggca caagctggag tacaactaca acagccacaa
cgtctatatc atggccgaca gcagaagaa cggcatcaag
gtgaacttca agatccgcca caacatcgag gacggcagcg
tgcagctcgc cgaccactac cagcagaaca cccccatcgg
cgacggcccc gtgctgctgc ccgacaacca ctacctgagc
acccagtccg ccctgagcaa agaccccaac gagaagcgcg
atcacatggt cctgctggag ttcgtgaccg ccgccgggat
cactctcggc atggacgagc tgtacaagta agtcgaggat
tataaggatg acgacgataa attcgtcgag caccaccacc
accaccacta ataaggttta tccgatccac cggatctaga
taagatatcc gatccaccgg atctagataa ctgatcataa
tcagccatac cacatttgta gaggttttac ttgctttaaa
aaacctccca cacctccccc tgaacctgaa acataaaatg
aatgcaattg ttgttgttaa cttgtttatt gcagcttata
atggttacaa ataaagcaat agcatcacaa atttcacaaa
taaagcattt ttttcactgc attctagttg tggtttgtcc
aaactcatca atgtatctta acgcggtaac cacgtgcgga
ccgagcggcc gcaggaaccc ctagtgatgg agttggccac
tccctctctg cgcgctcgct cgctcactga ggccgggcga
ccaaaggtcg cccgacgccc gggctttgcc cgggcggcct
cagtgagcga gcgagcgcgc agctgcctgc aggggcgcct
gatgcggtat tttctcctta cgcatctgtg cggtatttca
caccgcatac gtcaaagcaa ccatagtacg cgccctgtag
cggcgcatta gcgcggcgg gtgtggtggt tacgcgcagc
gtgaccgcta cacctgccag cgccttagcg cccgctcctt
tcgctttctt cccttccttt ctcgccacgt tcgccggctt
tccccgtcaa gctctaaatc ggggcatccc ttagggttc
cgatttagtg ctttacggca cctcgacccc aaaaaacttg
atttgggtga tggttcacgt agtgggccat cgccctgata
gacggttttt cgccctttga cgttggagtc cacgttcttt
aatagtggac tcttgttcca aactggaaca cactcaacc
ctatctcggg ctattctttt gatttataag gattttgcc
gatttcggcc tattggttaa aaaatgagct gatttaacaa
```

-continued

```
aaatttaacg cgaattttaa caaaatatta acgtttacaa
ttttatggtg cactctcagt acaatctgct ctgatgccgc
atagttaagc cagccccgac acccgccaac acccgctgac
gcgccctgac gggcttgtct gctcccggca tccgcttaca
gacaagctgt gaccgtctcc gggagctgca tgtgtcagag
gttttcaccg tcatcaccga aacgcgcgag acgaaagggc
ctcgtgatac gcctattttt ataggttaat gtcatgataa
taatggtttc ttagacgtca ggtggcactt ttcggggaaa
tgtgcgcgga acccctattt gtttattttt ctaaatacat
tcaaatatgt atccgctcat gagacaataa ccctgataaa
tgcttcaata atattgaaaa aggaagagta tgagtattca
acatttccgt gtcgccctta ttcccttttt tgcggcattt
tgccttcctg tttttgctca cccagaaacg ctggtgaaag
taaaagatgc tgaagatcag ttgggtgcac gagtgggtta
catcgaactg gatctcaaca gcggtaagat ccttgagagt
tttcgccccg aagaacgttt tccaatgatg agcactttta
aagttctgct atgtggcgcg gtattatccc gtattgacgc
cgggcaagag caactcggtc gccgcataca ctattctcag
aatgacttgg ttgagtactc accagtcaca gaaaagcatc
ttacggatgg catgacagta agagaattat gcagtgctgc
cataaccatg agtgataaca ctgcggccaa cttacttctg
acaacgatcg gaggaccgaa ggagctaacc gcttttttgc
acaacatggg ggatcatgta actcgccttg atcgttggga
accggagctg aatgaagcca taccaaacga cgagcgtgac
accacgatgc ctgtagcaat ggcaacaacg ttgcgcaaac
tattaactgg cgaactactt actctagctt cccggcaaca
attaatagac tggatggagg cggataaagt tgcaggacca
cttctgcgct cggcccttcc ggctggctgg tttattgctg
ataaatctgg agccggtgag cgtgggtctc gcggtatcat
tgcagcactg gggccagatg gtaagccctc ccgtatcgta
gttatctaca cgacggggag tcaggcaact atggatgaac
gaaatagaca gatcgctgag ataggtgcct cactgattaa
gcattggtaa ctgtcagacc aagtttactc atatatactt
tagattgatt taaaacttca ttttaatt aaaaggatct
aggtgaagat cctttttgat aatctcatga ccaaaatccc
ttaacgtgag ttttcgttcc actgagcgtc agaccccgta
gaaaagatca aaggatcttc ttgagatcct ttttttctgc
gcgtaatctg ctgcttgcaa acaaaaaaac caccgctacc
agcggtggtt tgtttgccgg atcaagagct accaactctt
tttccgaagg taactggctt cagcagagcg cagataccaa
```

```
atactgtcct tctagtgtag ccgtagttag gccaccactt caagaactct gtagcaccgc ctacatacct cgctctgcta atcctgttac cagtggctgc tgccagtggc gataagtcgt gtcttaccgg gttggactca agacgatagt taccggataa ggcgcagcgg tcgggctgaa cggggggttc gtgcacacag cccagcttgg agcgaacgac ctacaccgaa ctgagatacc tacagcgtga gctatgagaa agcgccacgc ttcccgaagg gagaaaggcg gacaggtatc cggtaagcgg cagggtcgga acaggagagc gcacgaggga gcttccaggg ggaaacgcct ggtatcttta tagtcctgtc gggtttcgcc acctctgact tgagcgtcga tttttgtgat gctcgtcagg ggggcggagc ctatggaaaa acgccagcaa cgcggccttt ttacggttcc tggccttttg ctggccttttt gctcacatgt
```

In SEQ ID NO:3, residues 1-128 of pAV-CMV-EGFP correspond to the 5' ITR; residues 201-441 are U6 promoter sequences; residues 562-865 are human cytomegalovirus (CMV) immediate early enhancer sequences; residues 866-1068 comprise the CMV immediate early promoter; residues 1192-1911 comprise a mammalian codon-optimized polynucleotide that encodes the EGFP; residues 1918-1941 encode the FLAG-tag; residues 1951-1968 encode the 6xHis-tag; residues 2139-2260 encode the SV40 poly(A) sequence; residues 2293-2433 correspond to the 3' ITR; residues 2508-22963 correspond to F1 ori sequences; residues 3350-4210 encode an ampicillin resistance determinant and its signal sequence (residues 3350-3418) expressed by a bla promoter sequence (residues 3245-3349); residues 4381-4969 correspond to an ori sequence (FIG. 5).

Figure 6:
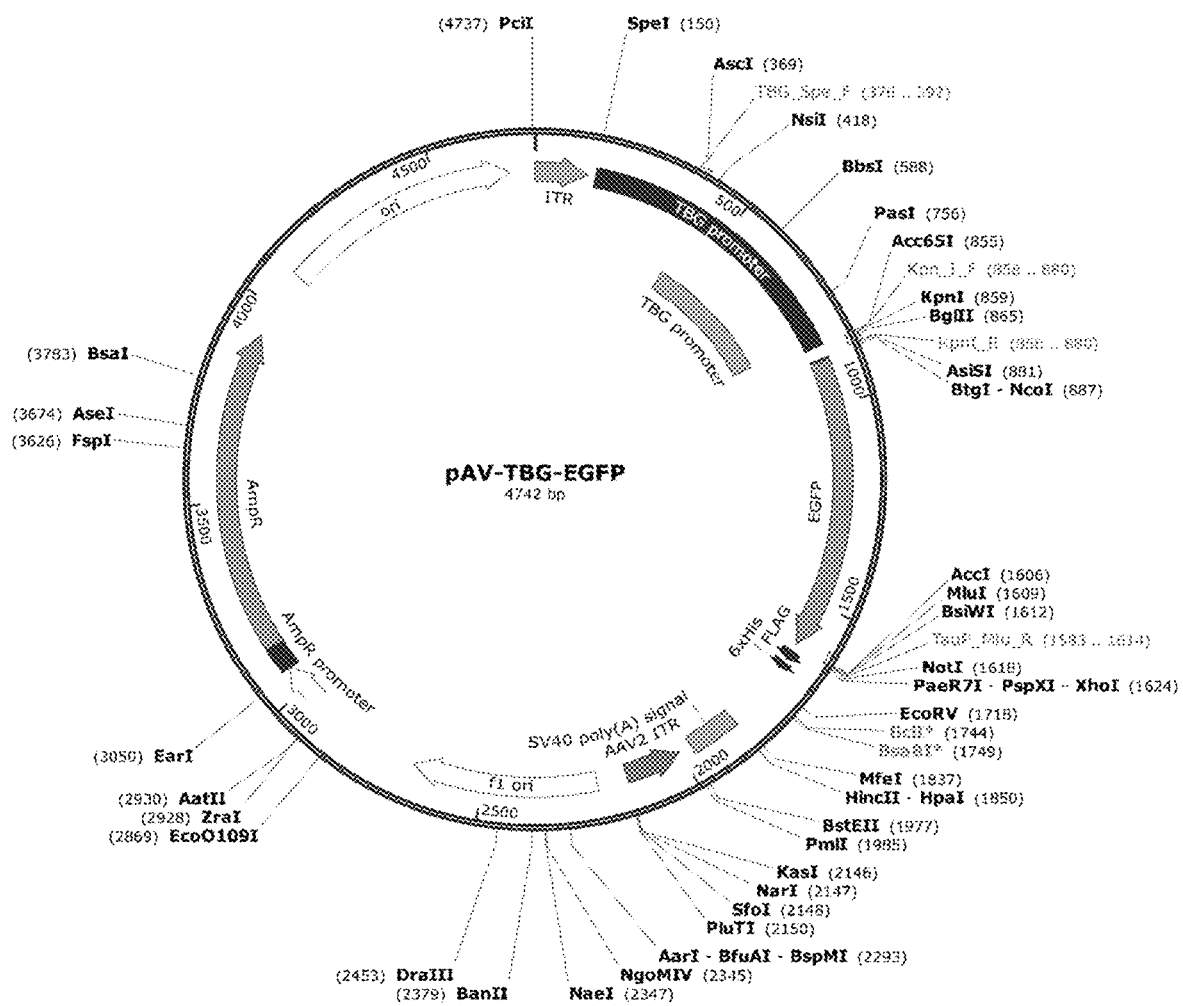
FIG. 6 shows a map of the rAAV plasmid vector pAV-TBG-EGFP.

A second illustrative rAAV plasmid vector that may be used in accordance with the present invention is pAV-TBG-EGFP (SEQ ID NO:4; FIG. 6) which comprises a 5' ITR, a thyroid hormone-binding globulin (TBG) promoter, a polynucleotide encoding the enhanced green fluorescent protein (EGFP), FLAG-tag and 6xHis-tag sites for facilitating recovery or localization of expressed proteins, an SV40 poly(A) site and a 3' ITR.

```
Coding Strand of Plasmid pAV-TBG-EGFP (SEQ ID
NO: 4):
cctgcaggca gctgcgcgct cgctcgctca ctgaggccgc ccgggcgtcg ggcgaccttt ggtcgcccgg cctcagtgag cgagcgagcg cgcagagagg gagtggccaa ctccatcact aggggttcct gcggccggtc gcgtctagta ctagtaggtt aattttttaaa aagcagtcaa aagtccaagt ggcccttggc agcatttact ctctctgttt gctctggtta ataatctcag gagcacaaac attccagatc caggttaatt tttaaaaagc agtcaaaagt ccaagtggcc cttggcagca tttactctct ctgtttgctc tggttaataa tctcaggagc acaaacattc cagatccggc gcgccagggc tggaagctac ctttgacatc atttcctctg cgaatgcatg tataatttct acagaaccta ttagaaagga tcacccagcc tctgcttttg tacaactttc ccttaaaaaa ctgccaattc cactgctgtt tggcccaata gtgagaactt tttcctgctg cctcttggtg cttttgccta tggcccctat tctgcctgct gaagacactc ttgccagcat ggacttaaac ccctccagct ctgacaatcc tctttctctt ttgttttaca tgaagggtct ggcagccaaa gcaatcactc aaagttcaaa ccttatcatt ttttgctttg ttcctcttgg ccttggtttt gtacatcagc tttgaaaata ccatcccagg gttaatgctg gggttaattt ataactaaga gtgctctagt tttgcaatac aggacatgct ataaaaatgg aaagatgttg cttttctgaga gacaggtacc gaggagatct gccgccgcga tcgccaccat ggtgagcaag ggcgaggagc tgttcaccgg ggtggtgccc atcctggtcg agctggacgg cgacgtaaac ggccacaagt tcagcgtgtc cggcgagggc gagggcgatg ccacttacgg caagctgacc ctgaagttca tctgcaccac cggcaagctg cccgtgccct ggcccaccct cgtgaccacc ctgacctacg gcgtgcagtg cttcagccgc tacccccacc acatgaagca gcacgacttc ttcaagtccg ccatgcccga aggctacgtc caggagcgca ccatcttctt caaggacgac ggcaactaca agacccgcgc cgaggtgaag ttcgagggcg acaccctggt gaaccgcatc gagctgaagg gcatcgactt caaggaggac ggcaacatcc tggggcacaa gctggagtac aactacaaca gccacaacgt ctatatcatg gccgacaagc agaagaacgg catcaaggtg aacttcaaga tccgccacaa catcgaggac ggcagcgtgc agctcgccga ccactaccag cagaacaccc ccatcggcga cggccccgtg ctgctgcccg acaaccacta cctgagcacc cagtccgccc tgagcaaaga ccccaacgag aagcgcgatc acatggtcct gctggagttc gtgaccgccg ccgggatcac tctcggcatg gacgagctgt acaagtagac gcgtacgcgg ccgctcgagg attataagga tgacgacgat aaattcgtcg agcaccacca ccaccaccac taataaggtt tatccgatcc accggatcta gataagatat ccgatccacc ggatctagat aactgatcat aatcagccat accacatttg tagaggtttt acttgcttta aaaaacctcc cacacctccc cctgaacctg aaacataaaa tgaatgcaat tgttgttgtt aacttgttta ttgcagctta taatggttac aaataaagca atagcatcac aaatttcaca aataaagcat ttttttcact gcattctagt tgtggtttgt ccaaactcat caatgtatct taacgcggta accacgtgcg gacccaacgg ccgcaggaac ccctagtgat ggagttggcc actccctctc tgcgcgctcg ctcgctcact gaggccgggc gaccaaaggt
```

```
cgcccgacgc cgggctttg ccgggcggc ctcagtgagc
gagcgagcgc gcagctgcct gcaggggcgc ctgatgcggt
attttctcct tacgcatctg tgcggtattt cacaccgcat
acgtcaaagc aaccatagta cgcgccctgt agcggcacat
taagcgcggc gggtgtggtg gttacgcgca gcgtgaccgc
tacacctgcc agcgccttag cgcccgctcc tttcgctttc
ttcccttcct ttctcgccac gttcgccggc tttccccgtc
aagctctaaa tcgggggctc cctttaggggt tccgatttag
tgctttacgg cacctcgacc ccaaaaaact tgatttgggt
gatggttcac gtagtgggcc atcgccctga tagacggttt
ttcgcccttt gacgttggag tccacgttct ttaatagtgg
actcttgttc caaactgaa caacactcaa ctctatctcg
ggctattctt ttgatttata agggattttg ccgatttcgg
tctattggtt aaaaaatgag ctgatttaac aaaaatttaa
cgcgaatttt aacaaaatat taacgtttac aattttatgg
tgcactctca gtacaatctg ctctgatgcc gcatagttaa
gccagccccg acacccgcca cacccgctg acgcgccctg
acgggcttgt ctgctcccgg catccgctta cagacaagct
gtgaccgtct ccgggagctg catgtgtcag aggttttcac
cgtcatcacc gaaacgcgcg agacgaaagg gcctcgtgat
acgcctattt ttataggtta atgtcatgat aataatggtt
tcttagacgt caggtggcac ttttcgggga aatgtgcgcg
gaaccctat ttgtttattt ttctaaatac attcaaatat
gtatccgctc atgagacaat aaccctgata aatgcttcaa
taatattgaa aaaggaagag tatgagtatt caacatttcc
gtgtcgccct tattcccttt tttgcggcat tttgccttcc
tgttttgct cacccagaaa cgctggtgaa agtaaaagat
gctgaagatc agttgggtgc acgagtgggt tacatcgaac
tggatctcaa cagcggtaag atccttgaga gttttcgccc
cgaagaacgt tttccaatga tgagcacttt taaagttctg
ctatgtggcg cggtattatc ccgtattgac gccgggcaag
agcaactcgg tcgccgcata cactattctc agaatgactt
ggttgagtac tcaccagtca cagaaaagca tcttacggat
ggcatgacag taagagaatt atgcagtgct gccataacca
tgagtgataa cactgcgcc aacttacttc tgacaacgat
cggaggaccg aaggagctaa ccgcttttt gcacaacatg
ggggatcatg taactcgcct tgatcgttgg gaaccggagc
tgaatgaagc cataccaaac gacgagcgtg acaccacgat
gcctgtagca atggcaacaa cgttgcgcaa actattaact
ggcgaactac ttactctagc ttcccggcaa caattaatag
```

```
actggatgga ggcggataaa gttgcaggac cacttctgcg
ctcggcccctt ccggctggct ggtttattgc tgataaatct
ggagccggtg agcgtgggtc tcgcggtatc attgcagcac
tggggccaga tggtaagccc tcccgtatcg tagttatcta
cacgacgggg agtcaggcaa ctatggatga acgaaataga
cagatcgctg agataggtgc ctcactgatt aagcattggt
aactgtcaga ccaagtttac tcatatatac tttagattga
tttaaaactt cattttttaat ttaaaaggat ctaggtgaag
atccttttg ataatctcat gaccaaaatc ccttaacgtg
agttttcgtt ccactgagcg tcagacccccg tagaaaagat
caaaggatct tcttgagatc ctttttttct gcgcgtaatc
tgctgcttgc aaacaaaaaa accaccgcta ccagcggtgg
tttgtttgcc ggatcaagag ctaccaactc ttttttccgaa
ggtaactggc ttcagcagag cgcagatacc aaatactgtt
cttctagtgt agccgtagtt aggccaccac ttcaagaact
ctgtagcacc gcctacatac ctcgctctgc taatcctgtt
accagtggct gctgccagtg gcgataagtc gtgtcttacc
gggttggact caagacgata gttaccggat aaggcgcagc
ggtcgggctg aacggggggt tcgtgcacac agcccagctt
ggagcgaacg acctacaccg aactgagata cctacagcgt
gagctatgag aaagcgccac gcttcccgaa gggagaaagg
cggacaggta tccggtaagc ggcagggtcg aacaggaga
gcgcacgagg gagcttccag ggggaaacgc ctggtatctt
tatagtcctg tcgggtttcg ccacctctga cttgagcgtc
gatttttgtg atgctcgtca ggggggcgga gcctatggaa
aaacgccagc aacgcggcct ttttacggtt cctggccttt
tgctggcctt ttgctcacat gt
```

In SEQ ID NO:4, residues 1-130 of pAV-TBG-EGFP correspond to the 5' ITR; residues 150-854 are TBG promoter sequences, with residues 415-824 comprising the TBG promoter; residues 886-1608 encode the EGFP; residues 1630-1653 encode the FLAG-tag; residues 1663-1680 encode the 6×His-tag; residues 1851-1972 encode the poly (A) sequence; residues 2005-2145 corresponds to the 3' ITR; residues 2220-2675 correspond to F1 ori sequences; residues 3062-3922 encode an ampicillin resistance determinant and its signal sequence (residues 3062-3130) expressed by a bla promoter sequence (residues 2957-3061); residues 4093-4681 correspond to an ori sequence (FIG. 6).

As used herein, the term "production titer" is intended to denote the amount of concentration of infectious rAAV in a preparation. Such amounts or concentrations are preferably determined by titering the AAV or rAAV in such preparation. The production titers of the rAAV preparations of the present invention are preferably titered after subjecting producing cells (e.g., HEK293 transformed with an rAAV plasmid vector, an AAV helper vector providing Rep and Cap proteins, and an Ad helper vector providing required adenovirus transcription and translation factors) to three rounds of freeze/thawing, followed by sonication to release the rAAV particles. The preparation is then centrifuged. The employed AAV vector is localized to the supernatant. An aliquot of the preparation is treated with proteinase K, and the number of AAV genomes is determined. An aliquot of the preparation is infected into HeLa-32C2 cells (which express AAV2 Rep and Cap proteins), and infectious titer is measured using the infectious center assay (ICA) (Francois, A. et al. (2018) "*Accurate Titration of Infectious AAV Particles Requires Measurement of Biologically Active Vector Genomes and Suitable Controls*," Molec. Ther. Meth. Clin. Develop. 10:223-236) or more preferably, as the median tissue culture infective dose (TCID50) (Zen, Z. et al. (2004) "*Infectious Titer Assay For Adeno Associated Virus Vectors With Sensitivity Sufficient To Detect Single Infectious Events*," Hum. Gene Ther. 15:709-715).

As used herein, an rAAV production titer is said to be "increased" by the methods of the present invention if the production titer obtained from the use of the methods of the present invention is at least 10% greater, more preferably at least 20% greater, still more preferably at least 30% greater, still more preferably at least 40% greater, still more preferably at least 50% greater, still more preferably at least 60% greater, still more preferably at least 70% greater, still more preferably at least 80% greater, still more preferably at least 90% greater, still more preferably at least 2-fold greater, still more preferably at least 110% greater, still more preferably at least 120% greater, still more preferably at least 130% greater, still more preferably at least 140% greater, still more preferably at least 2.5-fold greater, still more preferably at least 160% greater, still more preferably at least 170% greater, still more preferably at least 180% greater, still more preferably at least 190% greater, and still more preferably at least 3-fold greater than the titer obtained from a similarly conducted production in which the additionally provided ions were not provided.

The rAAV whose production titer may be increased using the methods of the present invention may comprise any transgene cassette that permits the rAAV to be packaged into an rAAV plasmid vector that may be encapsidated within an AAV capsid particle. Without limitation, such transgene cassette(s) may be of human, primate (including chimpanzee, gibbon, gorilla, orangutan, etc.), cercopithecine (including baboon, cynomolgus monkey, velvet monkey, etc.), canine, glirine (including rat, mouse, hamster, guinea pig, etc.), feline, ovine, caprine, or equine origin.

In preferred embodiments, such an rAAV or rAAV plasmid vector will encode a protein (e.g., an enzyme, hormone, antibody, receptor, ligand, etc.), or comprise a transcribed nucleic acid, that is relevant to a genetic or heritable disease or condition, such that it may be used in gene therapy to treat such disease or condition.

The methods of the present invention may be used to increase the production titer of rAAV and rAAV plasmid vectors in cells that have been transfected with a desired rAAV or rAAV plasmid vector, and with such one or more viruses and/or helper plasmids that can provide proteins or RNA molecules that are not provided by such rAAV or rAAV plasmid vectors, but are required for their production. As discussed above, such proteins or RNA molecules include the genes encoding the Rep52 and Rep78 proteins that are required for vector transcription control and replication, and for the packaging of viral genomes into the viral capsule, and, in the case of rAAV, cap genes that encode VP capsid proteins required to form infectious particles. Such proteins or RNA molecules also include the viral transcription and translation factors (E1a, E1b, E2a, VA and E4) required for AAV proliferation. In one embodiment for producing the rAAV of the present invention, all of these genes and RNA molecules are provided on the same helper virus (or more preferably, helper vector) so as to comprise, in concert with an rAAV, a double plasmid transfection system. More preferably, however, for producing the rAAV of the present invention, the required rep and cap genes are provided by one plasmid, and the genes that encode the viral transcription and translation factors are provided on a second plasmid, so that such plasmids, in concert with the rAAV, comprise a triple plasmid transfection system.

The methods of the present invention may be employed to increase the production titer of rAAV belonging to any serotype, including the AAV1, AAV2, AAV5, AAV6, AAV7, AAV8, AAV9 and AAV10 serotypes and the rAAV1, rAAV2, rAAV5, rAAV6, rAAV7, rAAV8, rAAV9, and rAAV10 serotypes, and including hybrid serotypes (e.g., AAV2/5 and rAAV2/5, which is a hybrid of serotypes 2 and 5 and thus has the trophism of both such serotypes).

The methods of the present invention may be employed to enhance the production titers of rAAV that are to be produced using "helper" RNA or proteins provided by an adenovirus, a herpes simplex virus, a cytomegalovirus, a vaccinia virus or a papillomavirus.

The methods of the present invention may be employed to enhance the production titers of rAAV produced by cells in adherent monolayer culture or in suspension culture, and may be used with any method capable of producing rAAV. Preferably, however, rAAV is produced by transfecting baby hamster kidney (BHK) cells, or more preferably, human embryonic kidney (HEK) cells grown in tissue culture with the plasmid vectors described above. The BHK cell line BHK-21 (ATCC CCL-10), which lacks endogenous retroviruses is a preferred BHK cell line. The HEK cell line HEK293 (ATCC CRL-1573) and its derivatives, such as HEK293T (ATCC CRL-3216, which is a highly transfectable derivative of the HEK293 cell line into which the temperature-sensitive gene for SV40 T-antigen was inserted) or HEK293T/17 (ATCC® CRL-11268, which was selected for its ease of transfection) are particularly preferred. The HEK293T/17 SF cell line (ATCC ACS-4500) is a derivative of the 293T/17 cell line (ATCC CRL-11268), adapted to serum-free medium and suspension, and may be employed if desired.

The preferred base medium of the present invention for culturing such cells is Eagle's Minimum Essential Medium (ATCC Catalog No. 30-2003) or Dulbecco's Modified Eagle's Medium (DMEM; Mediatech, Manassas, Va.). Fetal bovine serum (e.g., FBS; HyClone Laboratories, South Logan, Utah) is added to a final concentration of 10% in order to make the complete growth medium. Eagle's Minimum Essential Medium and Dulbecco's Modified Eagle's Medium are complex media that contain amino acids, vitamins, and optionally glucose, in addition to various inorganic salts. Although different sources differ slightly in the concentrations of such salts, Dulbecco's Modified Eagle's Medium (commercially available from, e.g., ThermoFisher Scientific) additionally contains approximately the inorganic salts shown in Table 1. The media differ in that Dulbecco's modified Eagle's medium contains approximately four times as much of the vitamins and amino acids present in the original formula of Eagle's Minimum Essential Medium, and two to four times as much glucose. Additionally, it contains iron in the form of ferric sulfate and phenol red for pH indication (Yao, T et al. (2017) "*Animal-Cell Culture Media: History, Characteristics, And Current Issues*," Reproduc. Med. Biol. 16(2): 99-117).

TABLE 1

| Inorganic Salt | Formula | Concentration | |
| --- | --- | --- | --- |
| | | mg/L | Molarity |
| Calcium Chloride | $CaCl_2$ | 200 | 1.80 mM |
| Ferric Nitrate | $Fe(NO_3)_3$—$9H_2O$ | 0.1 | 0.25 μM |
| Magnesium Sulfate (Anhyd.) | $MgSO_4$ | 97.67 | 0.81 mM |
| Potassium Chloride | KCl | 400 | 5.37 mM |
| Sodium Bicarbonate | $NaHCO_3$ | 3700 | 44.04 mM |
| Sodium Chloride | NaCl | 6400 | 109.5 mM |
| Sodium Phosphate Monobasic | $NaH_2PO_4$—$H_2O$ | 125 | 0.78 mM |
| Sodium Phosphate Dibasic | $Na_2HPO_4$—$H_2O$ | | |

Cells to be used for such transfection are preferably passaged twice weekly to maintain them in exponential growth phase. For small-scale transfections, an aliquot of, for example, $1 \times 10^6$ HEK293 or BHK cells per well on a multi-well plate, or $1.5 \times 10^7$ HEK293 cells per 15-cm dish, may be employed. For large-scale production HEK293 or BHK cells may be collected from multiple confluent 15-cm plates, and split into two 10-layer cell stacks (Corning, Corning, N.Y.) containing 1 liter of complete culturing medium. In one embodiment, such cells are grown for 4 days in such medium before transfection. The day before transfection, the two cell stacks may be trypsinized and the cells (e.g., approximately $6 \times 10^8$ cells) may be resuspended in 200 ml of medium. Preferably, the cells are allowed to attach for 24 hours before transfection. Confluency of the cell stacks may be monitored using a Diaphot inverted microscope (Nikon, Melville, N.Y.) from which the phase-contrast hardware had been removed in order to accommodate the cell stack on the microscope stage.

As used herein, the phrase "ionic strength" is intended to denote the concentration of ions in a solution. The present invention enhances rAAV production titers by increasing the ionic strength of the culture medium by providing additional ions to the medium used to culture rAAV transfected cells. In one embodiment, the provided ions are cations. Suitable cations include $Na^+$, $K^+$, $Ca^{++}$, and $Mg^{++}$. Such cations may be provided as an inorganic salt or as a salt of organic molecule. In another embodiment, the provided ions are anions. Suitable anions include inorganic anions such as: $CO_3^=$, $HCO_3^-$, $HPO_4^-$, $PO_4^=$, $SCN^-$ (thiocyanate), $SO_4^=$, $HSO_4^-$, and $Cl^-$, and organic ions, such as: acetate ($CH_3COO^-$), aspartate, biphthalate, bitartrate, butoxyethoxy acetate, caprylate, citrate ($C_6HSO_7^-$), dehydroacetate, diacetate, dihydroxy glycinate, d-saccharate, gluconate, glutamate, glycinate, glycosulfate, hydroxymethane sulfonate, lactate, methionate, oxalate, phenate, phenosulfonate, propionate, propionate, saccharin, salicylate, sarcosinate, sorbate, thioglycolate, and toluene sulfonate.

Such cations or anions may be provided at any concentration sufficient to enhance rAAV production titers over the titers produced in the same culture medium without any such additionally provided cations. Suitable concentrations of such cations or anions include concentrations sufficient to increase the initial concentration of such ion in a culturing medium by from about 30 mM to about 80 mM, by from about 40 mM to about 80 mM, by from about 50 mM to about 80 mM, by from about 60 mM to about 80 mM, by from about 70 mM to about 80 mM, or by about 80 mM, with such concentrations being in addition to any concentration of such ion present in such culture medium prior to such addition. If such culture medium did not initially contain the ions to be administered, then such added ions are preferably provided in an amount sufficient to provide concentrations of the provided ions in such culture medium of from about 30 mM to about 80 mM, by from about 40 mM to about 80 mM, by from about 50 mM to about 80 mM, by from about 60 mM to about 80 mM, by from about 70 mM to about 80 mM or to about 80 mM.

The ions or salts that are to be added to the initial culture medium may be added at any time prior to the harvesting of produced rAAV. Preferably, such ions or salts will have been added at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 12 hours, at least about 15 hours, at least about 18 hours, at least about 20 hours, at least about 22 hours, or at least about 24 hours after the initiation of the culturing.

As used herein, the term "about" when used with reference to a concentration, amount, or time, is intended to denote such concentration and also a range of concentrations that is within ±40% of such concentration, and more preferably within ±30% of such concentration, and still more preferably within ±20% of such concentration, and still more preferably within ±10% of such concentration, and still more preferably within ±5% of such concentration. Thus, for example, a recited concentration of 10.0 mM denotes a concentration of 10.0 mM, as well as a concentration between 6-14 mM, and more preferably a concentration between 7-13 mM and still more preferably a concentration between 8-12 mM, and still more preferably a concentration between 9-11 mM, and still more preferably a concentration between 9.5-10.5 mM.

Thus, for example, since Dulbecco's Modified Eagle's Medium has an initial $K^+$ concentration of about 5.37 mM, a provision of additional $K^+$ sufficient to increase the concentration of such cation by about 30 mM would cause the culture medium to have a resultant $Na^+$ concentration of about 35.4 mM. Likewise, since Dulbecco's Modified Eagle's Medium has an initial $HCO_3^-$ concentration of about 44.04 mM, a provision of additional $HCO_3^-$ sufficient to increase the concentration of such cation by about 30 mM would cause the culture medium to have a resultant $HCO_3^-$ concentration of about 74.04 mM.

In particular, the present invention thus provides a method for increasing the production titer of recombinantly-modified AAV (rAAV) that comprises the steps:
(A) culturing cells that have been transfected with such rAAV in a culture medium for an initial period under conditions sufficient to permit the production of rAAV;
(B) changing the ionic strength of the culture medium after the initial period by adding one or more ions, and preferably one or more ions other than $Na^r$, to the culture medium, in an amount sufficient to increase the concentration of such ion in the culture medium by from about 30 mM to about 80 mM;
(C) continuing the culturing of the cells to thereby produce a production titer of rAAV that is greater than a titer obtained in the absence of step (B).

The invention particularly contemplates the use of $KHCO_3$ to enhance rAAV production titer. Such $KHCO_3$ is preferably provided in an amount sufficient to increase the concentrations of $K^+$ and $HCO_3^-$ in the culture medium by about 20 mM, by about 30 mM, by about 40 mM, or by about 50 mM. Such addition would cause the $K^+$ concentration in Dulbecco's Modified Eagle's Medium to be about 25 mM, about 35 mM, about 45 mM, or about 55 mM, and would cause the $HCO_3^-$ concentration in such medium to be about 64 mM, about 74 mM, about 84 mM or about 94 mM. If such culture medium did not contain $K^+$ and $HCO_3^-$ ions, then such $KHCO_3$ is preferably provided in an amount sufficient to provide concentrations of K⁺ and HCO₃⁻ in such culture medium of about 20 mM, of about 30 mM, or of about 40 mM.

II. Pharmaceutical Compositions of the Present Invention

The invention additionally includes pharmaceutical compositions that comprise a pharmaceutically acceptable preparation of rAAV produced in accordance with the methods of the present invention, and a pharmaceutically acceptable carrier. The rAAV of such pharmaceutical compositions comprises a transgene cassette that encodes a protein, or comprises a transcribed nucleic acid, that is therapeutic for a genetic or heritable disease or condition, and is present in such pharmaceutical composition in an amount effective to ("effective amount")

The term "pharmaceutically acceptable" means approved by a regulatory agency of the Federal or a state government or listed in the US Pharmacopeia or other generally recognized pharmacopeia for use in animals, and more particularly in humans. The term "carrier" refers to a diluent, adjuvant (e.g., Freund's adjuvant complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Suitable pharmaceutical excipients are described in U.S. Pat. Nos. 8,852,607; 8,192,975; 6,764,845; 6,759,050; and 7,598,070.

Generally, the ingredients of compositions of the invention are supplied either separately or mixed together in unit dosage form, for example, as a dry lyophilized powder or water-free concentrate, or as an aqueous solution in a hermetically sealed container such as a vial, an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline, or other diluent can be provided so that the ingredients may be mixed prior to administration.

The invention also provides a pharmaceutical pack or kit comprising one or more containers such pharmaceutical composition. Optionally associated with such container(s) can be a notice in the form prescribed by a governmental agency regulating the manufacture, use or sale of pharmaceuticals or biological products, which notice reflects approval by the agency of manufacture, use or sale for human administration.

The rAAV of such pharmaceutical compositions is preferably packaged in a hermetically sealed container, such as a vial, an ampoule or sachette indicating the quantity of the molecule, and optionally including instructions for use. In one embodiment, the rAAV of such kit is supplied as a dry sterilized lyophilized powder or water-free concentrate in a hermetically sealed container and can be reconstituted, e.g., with water, saline, or other diluent to the appropriate concentration for administration to a subject. The lyophilized material should be stored at between 2° C. and 8° C. in their original container and the material should be administered within 12 hours, preferably within 6 hours, within 5 hours, within 3 hours, or within 1 hour after being reconstituted. In another embodiment, the rAAV of such kit is supplied as an aqueous solution in a hermetically sealed container and can be diluted, e.g., with water, saline, or other diluent, to the appropriate concentration for administration to a subject. The kit can further comprise one or more other prophylactic and/or therapeutic agents useful for the treatment of the disease or condition, in one or more containers; and/or the kit can further comprise one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

III. Uses of the Invention

The methods of the present invention may be used to facilitate the production of rAAV, and may particularly be used to facilitate the production of rAAV that comprise transgene cassettes that encode a protein (e.g., an enzyme, hormone, antibody, receptor, ligand, etc.), or of rAAV that comprise a transcribed nucleic acid, that is relevant to a genetic or heritable disease or condition, such that it may be used in gene therapy to treat such disease or condition. Examples of such diseases and conditions include: achromatopsia (ACHM); alpha-1 antitrypsin (AAT) deficiency; Alzheimer's Disease; aromatic L-amino acid decarboxylase (AADC) deficiency; choroideremia (CHM); cancer; Duchenne muscular dystrophy; dysferlin deficiency; follistatin gene deficiency (BMDSIBM); hemophilia A; hemophilia B; hepatitis A; hepatitis B; hepatitis C; Huntington's disease; idiopathic Parkinson's disease; late-infantile neuronal ceroid lipofuscinosis (LINCL, an infantile form of Batten disease); Leber congenital amaurosis (LCA); Leber's hereditary optic neuropathy (LHON); limb girdle muscular dystrophy 1B (LGMD1B); limb girdle muscular dystrophy 1C (LGMD1C); limb girdle muscular dystrophy 2A (LGMD2A); limb girdle muscular dystrophy 2B (LGMD2B); limb girdle muscular dystrophy 21 (LGMD2I); limb girdle muscular dystrophy 2L (LGMD2L); lipoprotein lipase (LPL) deficiency; metachromatic leukodystrophy; neurological disability; neuromotor deficit; neuroskeletal impairment; Parkinson's disease; rheumatoid arthritis; Sanfilippo A syndrome; spinal muscular atrophy (SMA); X-linked retinoschisis (XLRS); α-sarcoglycan deficiency (LGMD2D); β-sarcoglycan deficiency (LGMD2E); γ-sarcoglycan deficiency (LGMD2C) and δ-sarcoglycan deficiency (LGMD2F).

IV. Embodiments of the Invention

The invention concerns a method for increasing the production titer of recombinantly-modified adeno-associated virus (rAAV), the recombinantly-modified adeno-associated virus (AAV) helper vector produced from such method, and uses and compositions thereof. It is particularly directed to the following embodiments E1-E19:

E1. A method for increasing the production titer of recombinantly-modified adeno-associated virus (rAAV), wherein the method comprises the steps:
  (A) culturing cells that have been transfected with the rAAV in an initial culture medium for an initial period under conditions sufficient to permit the production of rAAV, wherein the cells additionally contain an AAV helper function-providing polynucleotide and a non-AAV helper function-providing polynucleotide;
  (B) changing the ionic strength of the culture medium after the initial period by adding one or more ions other than $Na^+$ to the culture medium; and
  (C) continuing the culturing of the cells to thereby produce a production titer of with the rAAV that is greater than a titer obtained in the absence of step (B).

E2. The method of E1, wherein each of the added ion(s) is provided in an amount sufficient to increase the concentration of such ion in the initial culture medium by from about 10 mM to about 80 mM.

E3. The method of any one of E1 or E2, wherein the production titer is at least 50% greater than the titer obtained from a similarly conducted cell culturing in the absence of the step (B).

E4. The method of any one of E1-E3, wherein the rAAV comprises a transgene cassette that encodes a protein, or comprises a transcribed nucleic acid, that is therapeutic for a genetic or heritable disease or condition.

E5. The method of any one of E1-E4, wherein the rAAV belongs to the rAAV1, rAAV2, rAAV5, rAAV6, rAAV7, rAAV8, rAAV9 or rAAV10 serotype, or to a hybrid of the serotypes.

E6. The method of E5, wherein the rAAV belongs to the rAAV2, rAAV5, or rAAV9 serotype, or to a hybrid of the serotypes.

E7. The method of any one of E1-E6, wherein the added ions comprise one or more of $K^+$, $Ca^{++}$, or $Mg^{++}$.

E8. The method of any one of E1-E7, wherein the added ions comprise one or more of $CO_3^=$, $HCO_3^-$, $HPO_4^-$, $PO_4^=$, $SCN^-$, $SO_4^=$, $HSO_4^-$, and $Cl^-$.

E9. The method of any one of E1-E7, wherein the added ions comprise one or more of acetate, aspartate, biphthalate, bitartrate, butoxyethoxy acetate, caprylate, citrate, dehydroacetate, diacetate, dihydroxy glycinate, d-saccharate, gluconate, glutamate, glycinate, glycosulfate, hydroxymethane sulfonate, lactate, methionate, oxalate, phenate, phenosulfonate, propionate, propionate, saccharin, salicylate, sarcosinate, sorbate, thioglycolate, and toluene sulfonate.

E10. The method of any one of E1-E8, wherein the added ions comprise $K^+$ and $CO_3^=$.

E10. The method of any one of E1-E10, wherein the cells are human embryonic kidney cells.

E12. The method of E11, wherein the cells are HEK293 cells.

E13. The method of any one of E1-E10, wherein the cells are baby hamster kidney cells.

E14. The method of E13, wherein the cells are BHK21 cells.

E15. The method of any one of E1-E10, wherein the cells are sf9 insect cells. E16. The method of any one of E1-E15, wherein the initial culture medium is Dulbecco's Modified Eagle's Medium.

E17. The method of E16, wherein the initial culture medium is supplemented with serum.

E18. A pharmaceutical composition that comprises:
  (A) a preparation of recombinantly-modified adeno-associated virus (rAAV) produced by the method of any one of E1-E17, wherein the rAAV comprises a transgene cassette that encodes a protein, or a transcribed nucleic acid, that is therapeutic for a genetic or heritable disease or condition, and wherein the pharmaceutical composition contains an effective amount of the rAAV preparation; and
  (B) a pharmaceutically acceptable carrier.

E19. The preparation of recombinantly-modified adeno-associated virus (rAAV) produced by the method of any one of E1-E17, wherein the rAAV comprises a transgene cassette that encodes a protein, or a transcribed nucleic acid, or the pharmaceutical composition of E18, for use in the treatment of a genetic or heritable disease or condition.

EXAMPLES

Having now generally described the invention, the same will be more readily understood through reference to the following examples, which are provided by way of illustration and are not intended to be limiting of the present invention unless specified.

Example 1

Effect of Cation and Cation Concentration on rAAV Production

The effect of cation and cation concentration on AAV production was demonstrated using cultured HEK293 cells. The culture medium was changed, and then, one hour later, the cells were transfected with:
(1) the plasmid vector pAAV-RC2, which is capable of expressing the AAV rep and cap gene functions that are required for the replication and packaging of an rAAV;
(2) the plasmid vector pHelper, which is capable of providing the viral transcription and translation factors (E1a, E1b, E2a, VA and E4) required for AAV proliferation; and
(3) the rAAV plasmid vector pAV-CMV-EGFP, which comprises the transgene cassette encoding the enhanced green fluorescent protein (EGFP) and the AAV ITRs.

Figure 7A:
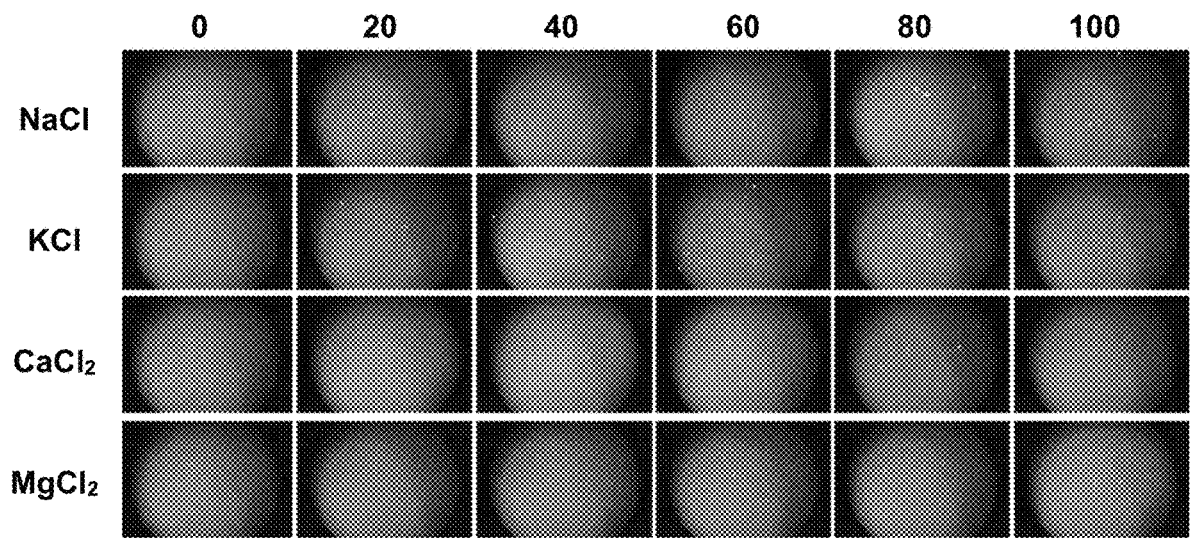
FIGS. 7A-7C show the effect of cation and cation concentration on the production of rAAV by transfected cells.
Figure 7B:
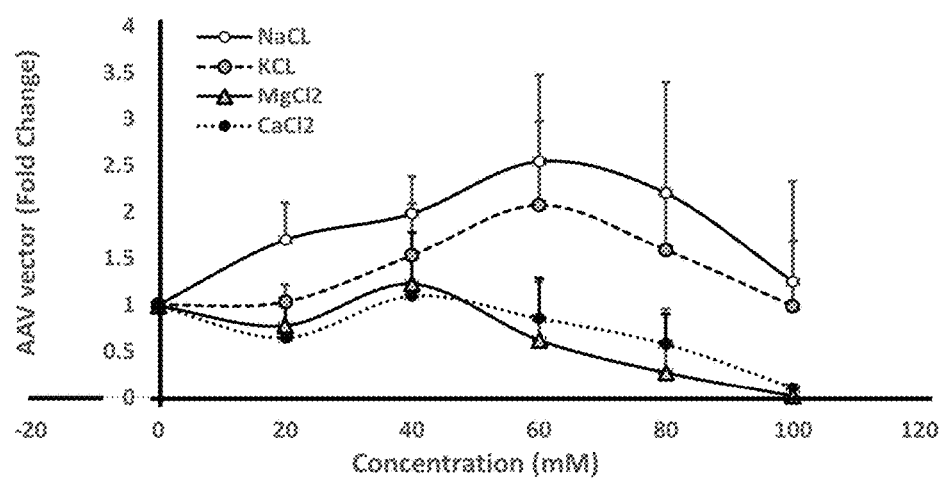
Figure 7C:
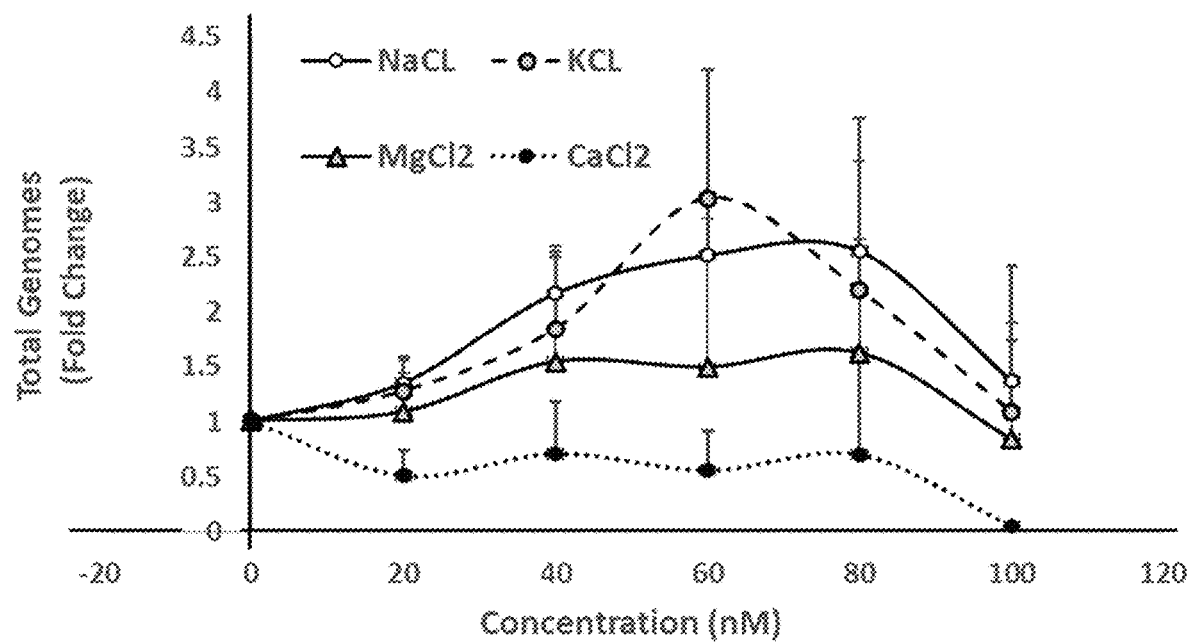

Five hours after such transfection, salt (either NaCl, KCl, $CaCl_2$ or $MgCl_2$) was provided to a final concentration of 0, 20, 40, 60 80 or 100 mM. FIG. 7A shows the extent of expression of EGFP in the transfected cells and the titering of the rAAV stocks using the infectious center assay. FIG. 7B is a graph of the fold-change in infectious centers as a function of such cation and cation concentrations. FIG. 7C is a graph of the fold-change in Total Genomes (TG) of AAV as a function of such cation and cation concentrations. The results show that the provision of cations affected the total genomes (TG) produced and that the provision of NaCl, KCl and $MgCl_2$ increased AAV genome replication and AAV production. Provision of NaCl and KCl was found to cause the highest titers of total genomes and the greatest increase in AAV production, with the greatest increase seen at NaCl and KCl concentrations that are sufficient to increase the concentrations of such ions in the culture medium by between about 40 mM to about 80 mM. The provision of higher concentrations of cations was found to inhibit EGFP expression (NaCl≥180 mM; KCl≥100 mM; $MgCl_2$≥60 mM).

Example 2

Effect of Anion and Anion Concentration on rAAV Production

Figure 8A:
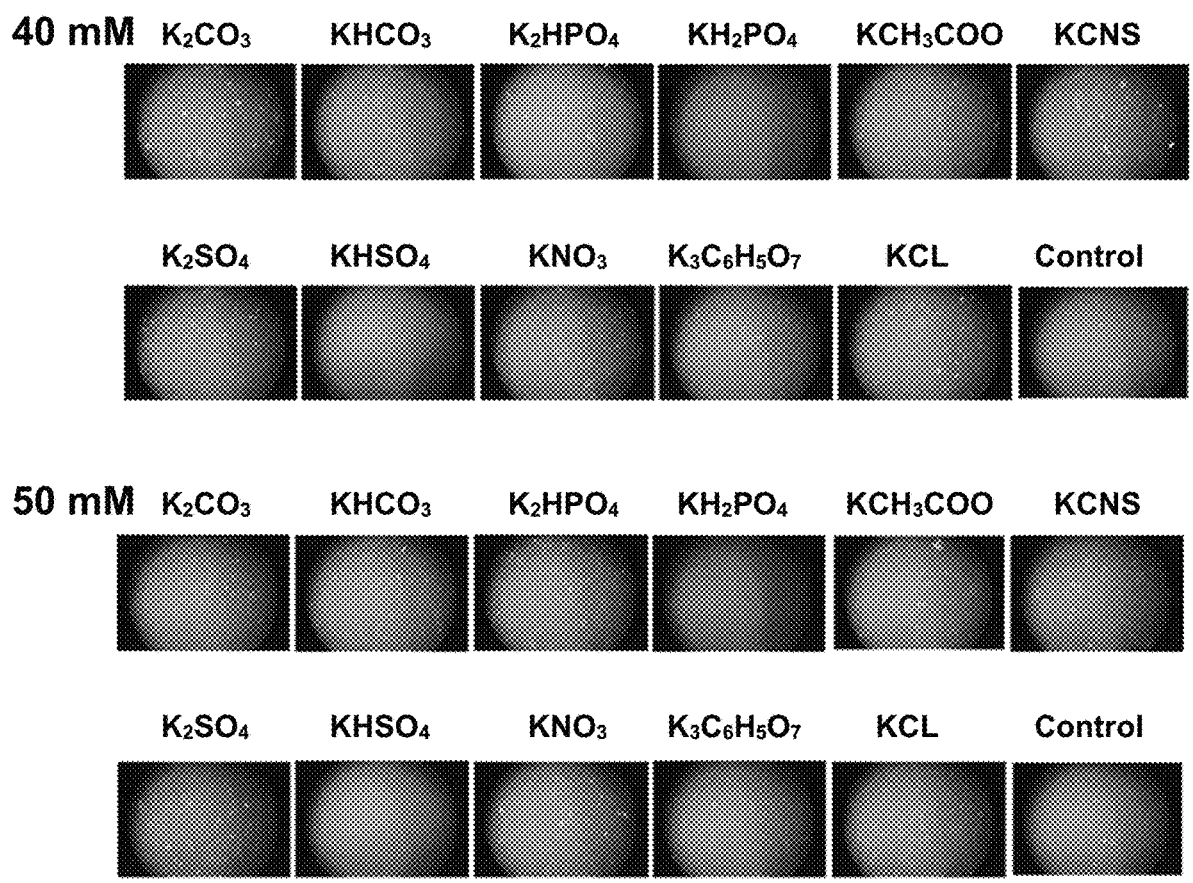
FIGS. 8A-8B show the effect of cation and cation concentration on the production of rAAV stocks.
Figure 8B:
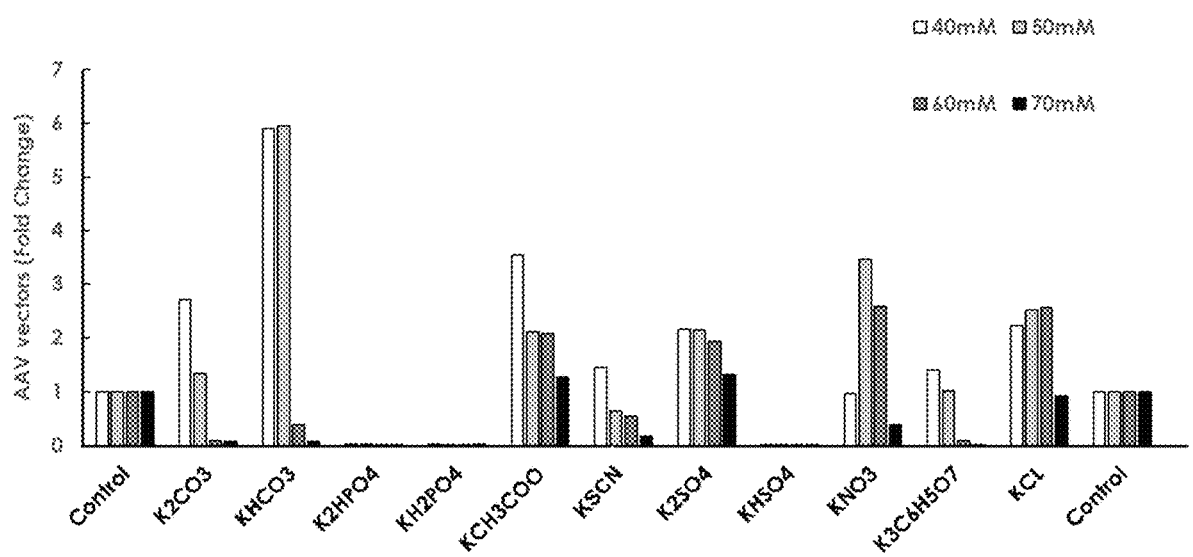
Figure 9A:
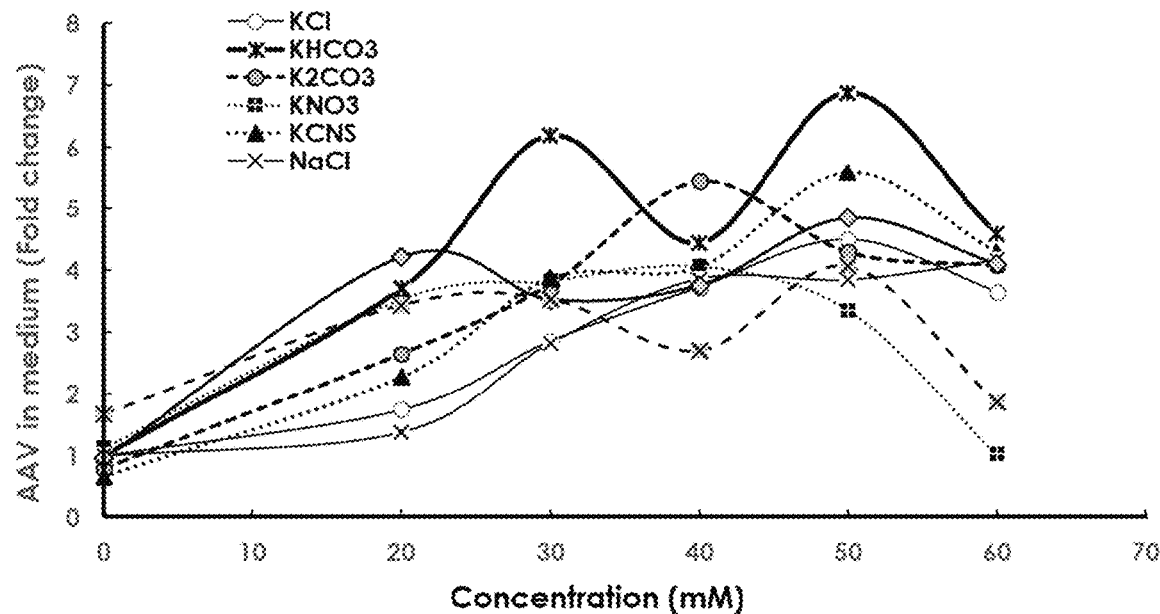
FIGS. 9A-9B demonstrate that the provision of $KHCO_3$ caused unexpectedly higher titers of rAAV, relative to other ions (FIG. 9A: fold-change in AAV titer in culture medium.
Figure 9B:
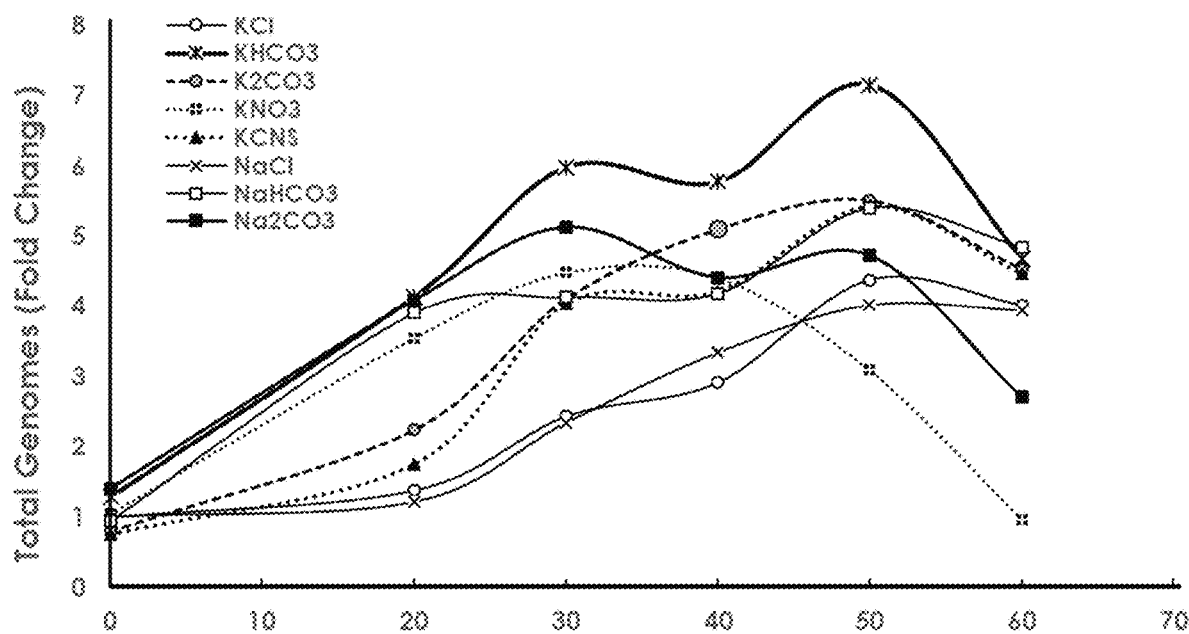

The effect of anion and anion concentration on AAV production was also demonstrated using cultured HEK293 cells. As in Example 1, the culture medium was changed, and one hour later, the cells were transfected with the Ad helper plasmid, the AAV helper plasmid, and the pAAV-ITR plasmid vector that provides the AAV ITRs and transgene cassette encoding the enhanced green fluorescent protein. Five hours after such transfection, salt (either $K_2CO_3$, $KHCO_3$, $KH_2PO_4$, $KCH_3COO$ (potassium acetate), KCNS, $K_2SO_4$, $KNO_3$, $K_3C_6HSO_7$ (potassium citrate) or KCL) was provided in an amount sufficient to increase the concentrations of such ions in the culture medium by 40, 50, 60, or 70 mM. The fold-change in rAAV infectious centers was determined after 72 hours. Provision of $KHCO_3$ was found to cause the greatest increase in rAAV production, with the greatest increase seen at concentrations sufficient to increase the concentrations of such ions by between about 40 mM to about 50 mM (FIG. 8A). FIG. 8B is a graph of the fold-change in the titer of rAAV vector as a function of such anion and anion concentrations. The results show that the provision of anions affected the total genomes (TG) produced. The provision of high concentrations of ions (>60 mM) was found to attenuate rAAV production. The results demonstrate that the provision of $KHCO_3$ in an amount sufficient to increase the concentrations of such ions in the culture medium by between about 30 mM and about 50 mM provided unexpectedly better results than those obtained with other salts (FIGS. 9A-9B). An increase in concentration by about 30 mM was considered optimum.

Example 3

Effect of Time of Provision of $KHCO_3$ on rAAV Production

Figure 10:
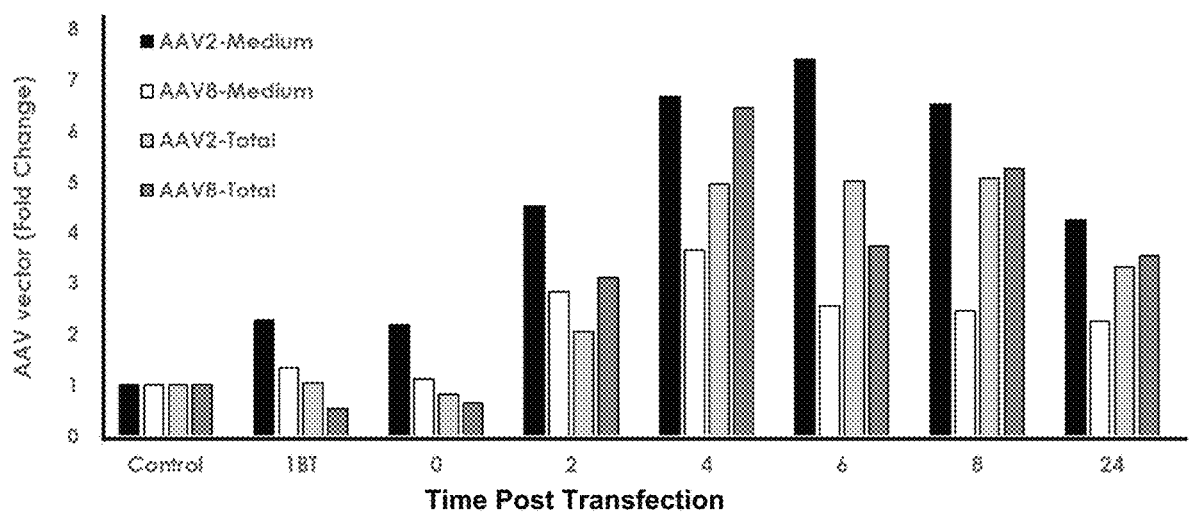
FIG. 10 shows the fold-change in the total amount of rAAV produced, and in the amount of rAAV released into the medium by cells that had been co-transfected with an Ad helper plasmid, a plasmid that provides the AAV ITRs, an enhanced green fluorescent protein-encoding transgene cassette and either an AAV2 helper plasmid or an AAV8 helper plasmid in order to provide the AAV rep and cap gene functions. At 2, 4, 6, 8, and 10 hours post-transfection, $KHCO_3$ was added to produce an additional concentration of 30 mM in the culturing medium and the fold-change of rAAV that had been released into the medium (AAV2-medium and AAV8-medium) and the total genomes in the cell lysis (AAV2-total and AAV8-total) were assessed at 72 hours post-transfection.

The effect caused by providing $KHCO_3$ at differing times post-transfection was also investigated. HEK293 cells were cultured and co-transfected with: (1) the above-described Ad helper plasmid, (2) the pAAV-ITR plasmid vector that provides the AAV ITRs and transgene cassette encoding the enhanced green fluorescent protein and (3) an AAV2 helper plasmid or an AAV8 helper plasmid in order to provide the AAV rep and cap gene functions. Culture medium had been changed one hour before the co-transfections. At 2, 4, 6, 8, and 10 hours post-transfection, $KHCO_3$ was added in an amount sufficient to increase the concentrations of such ions in the culture medium by a concentration of 30 mM and the fold-change of rAAV that had been released into the medium was assessed at 72 hours. The fold-change in the total amount of rAAV produced was also assessed (FIG. 10). The results indicate that the greatest enhancement was seen when salts were added 4-8 hours post-transfection.

Example 4

Effect of Serotype on rAAV Production

Figure 11A:
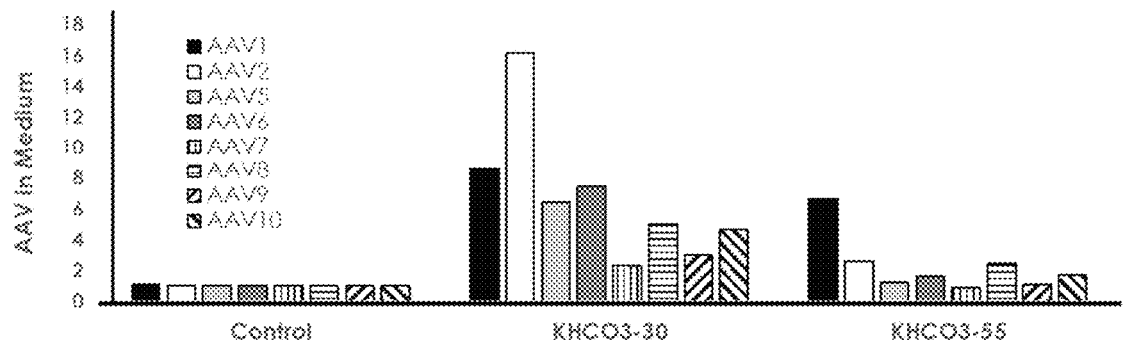
FIGS. 11A-11B show the effect of providing $KHCO_3$ on the enhancement of the production of rAAV of different serotypes.
Figure 11B:
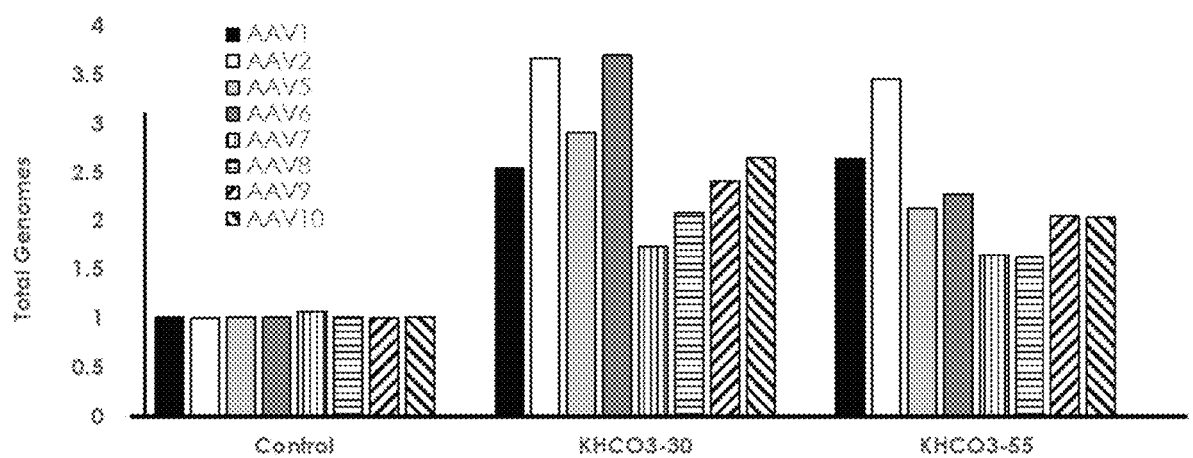

As discussed above, prior methods for enhancing the production of rAAV were not successful for rAAV having the AAV2 serotype (Lock, M. et al. (2010) "*Rapid, Simple, and Versatile Manufacturing of Recombinant Adeno Associated Viral Vectors at Scale*," Hum. Gene Ther. 21:1259-1271). In order to assess the ability of $KHCO_3$ addition to enhance the production of rAAV of different serotypes, AAV2 helper plasmid encoding Cap proteins of serotypes 1, 2, 5, 6, 7, 8, 9 or 10 were transfected into HEK293 cells along with the above-described Ad helper plasmid and a pAAV-ITR plasmid vector (pAV-TBG-EGFP) that provides the AAV ITRs and a transgene cassette encoding the enhanced green fluorescent protein. Four hours post-transfection, $KHCO_3$ was added to a final concentration of 30 mM and the fold-change of rAAV released into the medium was assessed at 72 hours. The results of this study are shown in FIGS. 11A-11B, and indicate that the addition of ions, and specifically the addition of $KHCO_3$, significantly increased the production titer of rAAV of all serotypes tested, including the rAAV2 serotype.

Example 5

Effect of Ion Provision on Large-Scale rAAV Production

In order to demonstrate that the provision of ions enhanced production of rAAV in large-scale preparations, rAAV of serotypes 1, 5, 6 and 9 with transgene cassettes encoding the green fluorescent protein or other exogenous molecules were produced in large-scale in the presence or absence of a total concentration of 30 mM $KHCO_3$ in five 15 cm dishes. AAV titers were obtained after purification. The results of this demonstration are shown in Table 2 (pDNA_001 donor construct, PiBFXNco3 and PiBFX-Nco11 are control vectors).

TABLE 2

Effect of $KHCO_3$ Provision on Large-Scale AAV Production

| AAV | Transgene | Yield (per mL) | Fold-Change | $KHCO_3$ Addition |
|---|---|---|---|---|
| AAV1 | | | | |
| A5514-1 | pAV-CMV-EGFP | $1.17 \times 10^{13}$ | — | None |
| A5514-2 | pAV-CMV-EGFP | $3.8 \times 10^{13}$ | 3.2 | 30 mM, 4 hours post-transfection |
| AAV5 | | | | |
| A5658 | pAV-CMV-EGFP | $1.14 \times 10^{13}$ | — | None |
| A5659 | pAV-CMV-GFP | $3.03 \times 10^{13}$ | 2.7 | 30 mM, 4 hours post-transfection |
| AAV6 | | | | |
| A5516-1 | pAV-CMV-EGFP | $1.25 \times 10^{13}$ | — | None |
| A5516-2 | pAV-CMV-EGFP | $2.69 \times 10^{13}$ | 2.2 | 30 mM, 4 hours post-transfection |
| A5555 | pDNA_001 donor construct | $8.99 \times 10^{12}$ | — | None |
| A5556 | pDNA_001 donor construct | $2.64 \times 10^{13}$ | 2.9 | 30 mM, 4 hours post-transfection |
| AAV9 | | | | |
| A5474-1 | PiBFXNco3 | $1.34 \times 10^{13}$ | — | None |
| A5474-2 | PiBFXNco3 | $1.61 \times 10^{13}$ | 1.2 | 30 mM, overnight post-transfection |
| A5475-1 | PiBFXNco11 | $3.14 \times 10^{12}$ | — | None |
| A5475-2 | PiBFXNco11 | $1.46 \times 10^{13}$ | 4.6 | 30 mM, overnight post-transfection |

As indicated in Table 2, the provision of ions, and particularly the provision of $KHCO_3$, resulted in an increase in rAAV production of 1.2 to 4.6 fold, with an average fold-increase of about 3-fold.

Example 6

Figure 12:
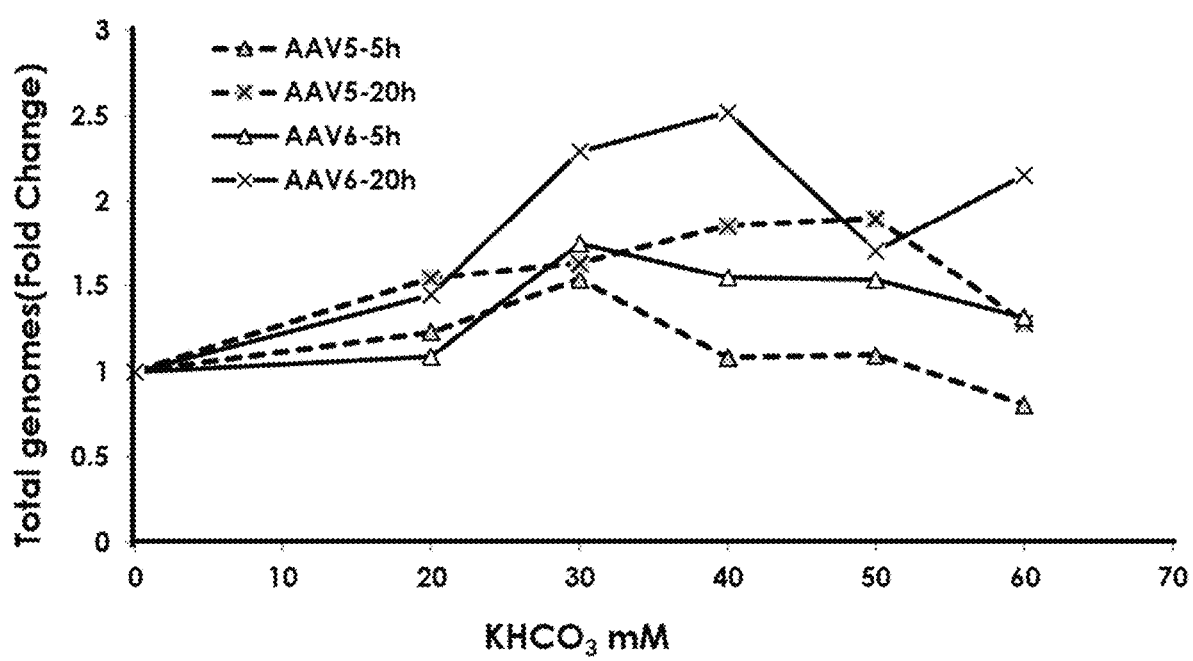
FIG. 12 shows the ability of cells cultured in suspension to produce enhanced levels of rAAV in response to the provision of $KHCO_3$. Provision of $KHCO_3$ sufficient to increase the concentration of $KHCO_3$ in the culturing medium by greater than about 20 mM enhanced production of rAAV5 and rAAV6 after 20 hours.

Effect of the Provision of Ions on the Production of rAAV by Cells Grown in Suspension In order to demonstrate that the provision of ions enhanced production of rAAV by cells that were grown in suspension, HEK293 cells were co-transfected with: (1) the above-described Ad helper plasmid, (2) the pAAV-ITR plasmid vector that provides the AAV ITRs and transgene cassette encoding the enhanced green fluorescent protein and (3) an AAV5 helper plasmid or an AAV6 helper plasmid in order to provide the AAV rep and cap gene functions. KHCO$_3$ was added in an amount sufficient to increase the concentrations of such ions in the culture medium by 10, 20, 30, 40, 50 or 60 mM at 5 hours or 20 hours post-transfection. Total Genomes of produced rAAV was determined at 72 hours post-transfection. Suspension cells were cultured at 37° C., 5% CO$_2$ with an agitation speed of 120 rpm. The ability of cells cultured in suspension to produce enhanced levels of rAAV in response to the provision of ions is shown in FIG. 8. As shown in FIG. 12, provision of ions at a final concentration of greater than about 20 mM enhanced production of rAAV5 and rAAV6.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for increasing the production titer of recombinantly-modified adeno-associated virus (rAAV), wherein said method comprises the steps:
   (A) culturing cells that have been transfected with said rAAV in an initial culture medium for an initial period under conditions sufficient to permit the production of rAAV, wherein said cells additionally contain an AAV helper function-providing polynucleotide and a non-AAV helper function-providing polynucleotide;
   (B) changing the ionic strength of said culture medium after said initial period by adding $K^+$ cations and one or more anions selected from the group consisting of $CO_3^=$, $HCO_3^-$, $CH_3COO^-$, $SO_4^=$, and $NO_3^-$ to said culture medium, wherein:
      (i) if the anion is $CO_3^=$, the added $K^+$ cations and $CO_3^=$ anions are added to the culture medium in an amount sufficient to increase the concentrations of $K^+$ and $CO_3^=$ in the culture medium by from about 40 mM to about 50 mM;
      (ii) if the anion is $HCO_3^-$, said added $K^+$ cations and $HCO_3^-$ anions are added to the culture medium in an amount sufficient to increase the concentrations of $K^+$ and $HCO_3^-$ in the culture medium by from about 30 mM to about 50 mM;
      (iii) if the anion is $CH_3COO^-$, the added $K^+$ cations and $CH_3COO^-$ anions are added to the culture medium in an amount sufficient to increase the concentrations of $K^+$ and $CH_3COO^-$ in the culture medium by from about 40 mM to about 70 mM;
      (iv) if the anion is $SO_4^=$, the added $K^+$ cations and $SO_4^=$ anions are added to the culture medium in an amount sufficient to increase the concentrations of $K^+$ and $SO_4^=$ in the culture medium by from about 40 mM to about 70 mM, and
      (v) if the anion is $NO_3^-$, the added $K^+$ cations and $NO_3^-$ anions are added to the culture medium in an amount sufficient to increase the concentrations of $K^+$ and $NO_3^-$ in the culture medium by from about 50 mM to about 60 mM; and
   (C) continuing said culturing of said cells to thereby produce a production titer of said rAAV that is greater than a titer obtained in the absence of step (B).

2. The method of claim 1, wherein the production titer is at least 50% greater than the titer obtained from a similarly conducted cell culturing in the absence of said step (B).

3. The method of claim 1, wherein said rAAV comprises a transgene cassette that encodes a protein, or comprises a transcribed nucleic acid, that is therapeutic for a genetic or heritable disease or condition.

4. The method of claim 1, wherein said rAAV belongs to the rAAV1, rAAV2, rAAV5, rAAV6, rAAV7, rAAV8, rAAV9 or rAAV10 serotype, or to a hybrid of said serotypes.

5. The method of claim 4, wherein said rAAV belongs to the rAAV2, rAAV5, or rAAV9 serotype, or to a hybrid of said serotypes.

6. The method of claim 1, wherein said cells are human embryonic kidney cells.

7. The method of claim 6, wherein said human embryonic kidney cells are HEK293 cells.

8. The method of claim 1, wherein said cells are baby hamster kidney cells.

9. The method of claim 8, wherein said baby hamster kidney cells are BHK21 cells.

10. The method of claim 1, wherein said cells are sf9 insect cells.

11. The method of claim 1, wherein said initial culture medium is Dulbecco's Modified Eagle's Medium.

12. The method of claim 11, wherein said Dulbecco's Modified Eagle's Medium initial culture medium is supplemented with serum.

13. A pharmaceutical composition that comprises:
    (A) a preparation of recombinantly-modified adeno-associated virus (rAAV) produced by the method of claim 1, wherein said rAAV comprises a transgene cassette that encodes a protein, or a transcribed nucleic acid, that is therapeutic for a genetic or heritable disease or condition, and wherein said pharmaceutical composition contains an effective amount of said rAAV preparation; and
    (B) a pharmaceutically acceptable carrier.

14. The method of claim 1, wherein the ionic strength of said culture medium is changed by the addition of $K^+$ cations and $HCO_3^-$ anions to said culture medium.

15. The method of claim 14, wherein the ionic strength of said culture medium is changed to increase the concentrations of $K^+$ cations and $HCO_3^-$ anions in said culture medium by a concentration of from about 40 mM to about 50 mM by addition of $KHCO_3$.

16. The method of claim 14, wherein the ionic strength of said culture medium is changed to increase the concentrations of $K^+$ cations and $HCO_3^-$ anions in said culture medium by a concentration of about 30 mM by addition of $KHCO_3$.

17. The method of claim 14, wherein the ionic strength of said culture medium is changed by the addition of $KHCO_3$ to said culture medium in an amount sufficient to increase the concentrations of $K^+$ cations and $HCO_3^-$ anions in said culture medium by a concentration of about 55 mM.

18. A pharmaceutical composition that comprises:
    (A) a preparation of recombinantly-modified adeno-associated virus (rAAV) produced by the method of claim 1, wherein said rAAV comprises a transgene cassette that encodes a protein, or a transcribed nucleic acid, that is therapeutic for a genetic or heritable disease or condition, and wherein said pharmaceutical composition contains an effective amount of said rAAV preparation; and
    (B) a pharmaceutically acceptable carrier.

19. The pharmaceutical composition of claim 18, wherein said culture medium is changed to increase the concentrations of $K^+$ cations and $HCO_3^-$ anions in said culture medium by a concentration of about 30 mM by addition of $KHCO_3$.

20. The pharmaceutical composition of claim 18, wherein said culture medium is changed to increase the concentrations of $K^+$ cations and $HCO_3^-$ anions in said culture medium by a concentration of about 55 mM by addition of $KHCO_3$.

* * * * *